US010995343B2

(12) United States Patent
Chandler et al.

(10) Patent No.: US 10,995,343 B2
(45) Date of Patent: May 4, 2021

(54) WHEAT WITH NEW ALLELES OF RHT-B1

(71) Applicants: Commonwealth Scientific and Industrial Research Organisation, Campbell, Australian Capital Territory (AU); Grains Research and Development Corporation, Barton, Australian Capital Territory (AU)

(72) Inventors: Peter Michael Chandler, Bywong (AU); Carol Anne Harding, Hackett (AU)

(73) Assignees: COMMONWEALTH SCIENTIFIC AND INDUSTRIAL RESEARCH ORGANISATION, Campbell (AU); GRAINS RESEARCH AND DEVELOPMENT CORPORATION, Barton (AU)

( * ) Notice: Subject to any disclaimer, the term of this patent is extended or adjusted under 35 U.S.C. 154(b) by 846 days.

(21) Appl. No.: 14/423,240

(22) PCT Filed: Aug. 22, 2013

(86) PCT No.: PCT/AU2013/000942
§ 371 (c)(1),
(2) Date: Feb. 23, 2015

(87) PCT Pub. No.: WO2014/028980
PCT Pub. Date: Feb. 27, 2014

(65) Prior Publication Data
US 2015/0257353 A1    Sep. 17, 2015

(30) Foreign Application Priority Data
Aug. 24, 2012   (AU) ............................... 2012903673

(51) Int. Cl.
*C12N 15/82* (2006.01)
*C07K 14/415* (2006.01)

(52) U.S. Cl.
CPC ........ *C12N 15/8297* (2013.01); *C07K 14/415* (2013.01); *C12N 15/8261* (2013.01)

(58) Field of Classification Search
None
See application file for complete search history.

(56) References Cited

U.S. PATENT DOCUMENTS

2012/0114770 A1* 5/2012 Regina .................. C12N 9/107
                                                      424/750

OTHER PUBLICATIONS

Wu, et al. Plant Physiology 157.4 (2011): 2120-2130.*
GenBank Accession JN857971, submittedOct. 13, 2011.*
Ikeda et al. (The Plant Cell, vol. 13, 999-1010, May 2001). (Year: 2001).*
Hirano, et al. (The Plant Cell 22.8 (2010): 2680-2696). (Year: 2010).*
Thomas (Journal of experimental botany 68.3 (2017):354-358). (Year: 2017).*
Wu, et al. (Plant Physiology 157.4 (2011): 2120-2130). (Year: 2011).*
Addisu, et al. (Euphytica 172.2 (2010): 169-181). (Year: 2010).*
GenBank Accession JN857971, dated Dec. 19, 2011. (Year: 2011).*
GenBank Accession Q7G7J6, 2000. (Year: 2000).*
Guo et al. (2004, Proc. Natl. Acad. Sci. USA 101:9205-9210). (Year: 2004).*
Pearce et al., Molecular Characterization of Rht-1 Dwarfing Genes in Hexaploid Wheat, 157 Plant Physiology 1820-1831 (Dec. 2011).
Wu et al., Dominant and Pleiotropic Effects of a GAI Gene in Wheat Results from a Lack of Interaction between DELLA and GID1, 157 Plant Physiology 2120-2130 (Dec. 2011).
International Preliminary Report on Patentability dated Feb. 24, 2015, in corresponding PCT Application PCT/AU2013/000942.
International Search Report dated Sep. 23, 2013, in corresponding PCT Application PCT/AU2013/000942.
Chandler et al., 'Overgrowth' mutants in barely and wheat: new alleles and phenotypes of the "Green Revolution" DELLA gene, 64(6) Journal of Experimental Botany 1603-1613 (2013).
Achard et al., Releasing the brakes of plant growth: how GAs shutdown DELLA proteins, (2009) *J. Exptl Bot.* 60, 1085-1092.
Arana et al., Circadian oscillation of gibberellin signaling in *Arabidopsis*, (2011) *Proc. Natl. Acad. Sci. USA.* 108, 9292-9297.
Asano et al., Isolation and characterization of dominant dwarf mutants, Slr1-d, in rice, (2009) 281, 223-231.
Carol et al., Isolation and preliminary characterization of gass1-1, a mutation causing partial suppression of the phenotype conferred by the gibberellin-insensitive (gai) mutation in *Arabidopsis thaliana* (L.) Heyhn, (1995) *Mol. Genet Genomics* (1995*Planta* 197, 414-417.
Chandler et al., Gibberellin Dose-Response Curves and the Characterization of Dwarf Mutants of Barley, (1999) *Plant Physiol.* 120, 623-632.
Chandler et al., Mutants of the Slender1 Locus of Barley cv Himalaya. Molecular and Physiological Characterization (2002) *Plant Physiol* 129, 181-190.
Chandler et al., Characterization of Gibberellin Receptor Mutants of Barley (*Hordeum vulgare* L.), (2008) *Mol. Plant.* 1, 285-294.
Chandler et al., Overgrowth Mutants of Barley and Wheat; Many New Alleles in the 'Green Revolution' Dwarfing Gene, SYM 15-04, OzBio2010 Combined Conference, Melbourne, Sep. 26-Oct. 1, 2010.

(Continued)

*Primary Examiner* — Charles Logsdon
(74) *Attorney, Agent, or Firm* — Buchanan Ingersoll & Rooney PC

(57) ABSTRACT

The present invention provides a wheat plant comprising an Rht-B1 allele which encodes an Rht-B1 (DELLA) polypeptide. Grain from a near-isogenic wheat line comprising the dwarfing Rht-B1c allele was subjected to sodium azide mutagenesis. Plants exhibiting early leaf elongation rates or mature plant height greater than the dwarf parent were selected and the Rht-B1 gene sequenced. This identified 35 mutated alleles of Rht-B1c. Similar methods were also used to identify mutant alleles of the dwarfing sln1d allele in barley, where DELLA is encoded by the sln1 gene.

71 Claims, 11 Drawing Sheets

Specification includes a Sequence Listing.

(56) References Cited

OTHER PUBLICATIONS

De Lucas et al., A molecular framework for light and gibberellin control of cell elongation, (2008) *Nature* 451, 480-484.
Dill et al., The *Arabidopsis* F-Box Protein gSLEEPY1 Targets Gibberellin Signaling Repressors for Gibberellin-Induced Degradation, (2004) *Plant Cell* 16, 1392-1405.
Ellis et al., Molecular mapping of gibberellin-responsive dwarfing genes in bread wheat, (2005) *Theor Appl Genet* 111, 423-430.
Feng et al., Coordinated regulation of *Arabidopsis thaliana* development by light and gibberellins, (2008) *Nature* 451, 475-479.
Flintham et al., Optimizing wheat grain yield: effects of Rht (gibberellin-insensitive) dwarfing genes, (1997) *J. Agric. Sci.* 128, 11-25.
Fu et al., Gibberellin-Mediated Proteasome-Dependent Degradation of the Barley DELLA Protein SLN1 Repressor, (2002) *Plant Cell* 14, 3191-3200.
Griffiths et al., Genetic Characterization and functional Analysis of the GID1Gibberellin Receptors in *Arabidopsis*, (2006) *Plant Cell* 18, 3399-3414.
Gooding et al., Reduced height alleles (Rht) and Hagberg falling number of wheat, (2012) *Journal of Cereal Science* 305-311.
Hartweck, Gibberellin signaling, (2008) *Planta* 229, 1-13.
Kuppusamy et al., Cross-regulatory mechanisms in hormone signaling, (2009) *Plant Mol. Biol.* 69, 375-381.
Li et al., Isolation of gibberellin-insensitive dwarfing gene, Rht-B1e, and development of an allele-specific PCR marker, (2012) 30 1443-1451.
Monna et al., Positional Cloning of rice Semidwarfing Gene, sd-/:Rice "Green Revolution Gene" Encodes a Mutant Enzyme Involved in Gibberellin Synthesis, (2002) Dna Res. 9, 11-17.
Murase et al., Gibberellin-induced DELLA recognition by the gibberellin receptor GID1 (2008) Nature 456, 459-463.
Pearce et al., Molecular Characterization of Rht-1 Dwarfing Genes in Hexaploid Wheat (2011) *Plant Physiol.* DOI:10.1104/pp. 111. 183657.
Peng et al., 'Green revolution' genes encode mutant gibberellin response modulators, (1999) *Nature* 400, 256-261.
Robertson et al., Identification of a Negative Regulator of Gibberellin Action, HvSPY, in Barley (1998) *Plant Cell* 10, 995-1007.
Sasaki et al., A mutant gibberellin-synthesis gene in rice, (2002) *Nature* 416, 701-702.
Sasaki et al., Accumulation of Phosphorylated Repressor for Gibberellin Signaling in an F-box Mutant, (2003) *Science* 299, 1896-1898.
Shimada et al., The rice SPINDLY gene functions as functions as a negative regulator of gibberellin signaling by controlling the suppressive function of the DELLA protein, SLR1, and modulating brassinosteroid synthesis, (2006) *Plant J.* 48, 390-402.
Shimada et al., Structural basis for gibberellin recognition by its receptor GID1, (2008) *Nature* 456, 520-544.
Silverstone et al., The New RGA Locus Encodes a native Regulator of Gibberellin Response in *Arabidopsis thaliana* (1997) *Genetics* 146, 1087-1099.
Silverstone et al., Functional Analysis of SPINDLY in Gibberellin Signaling in Arabidopsis, (2007) *Plant Physiol.* 143, 987-1000.
Spielmeyer et al., Semidwarf (sd-1), "green revolution" rice, contains a defective gibberellin 20-oxidase gene, (2002) *Proc Natl Acad Sci (USA)* 99, 9043-9048.
Sun, Givverellin-GID1-DELLA: A Pivotal Regulatory Module for Plant Growth and Development, (2010) *Plant Physiol* 154, 567-570.
Ueguchi-Tanaka et al., Gibberellin Insensitive DWARF1 encodes a soluble receptor for gibberellin, (2005) *Nature* 437, 693-698.
Willige et al., The DELLA Domain of GA Insensitive Mediates the Interaction with the GA Insensitive DWARF1A Gibberellin Receptor or *Arabidopsis*, (2007) *Plant Cell* 19, 1209-1220.
Wilson et al., Phenotypic Suppression of the Gibberellin-Insensitive Mutant (gai) of *Arabidopsis*, (1995) *Plant Physiol* 108: 495-502.
Wolbang et al., Auxin from the Developing Inflorescence Is Required for the Biosynthesis of Active Gibberellins in Barley Stems, (2004) *Plant Physiol* 134, 769-776.
Yamaguchi, Gibberellin Metabolism and its Regulation, (2008) *Annu. Rev. Plant Biol.* 59, 225-251.
Yamamoto et al., A Rice gid1 Suppressor Mutant Reveals That Reveals That Gibberellin Is Not Always Required for Interaction between Its Receptor, GID1, and DELLA Proteins, (2010) *Plant Cell* 22, 3589-3602.
Zwar et al., α-Amylase production and leaf protein synthesis in a gibberellin-responsive dwarf mutant of 'Himalaya' barley (*Hordeum vulgare* L.), (1995) *Planta* 197, 39-48.
Extended European Search Report dated Apr. 15, 2016, in corresponding EP Patent Application No. 13830254.2-1401.
Addisu et al., *Reduced height (Rht) and photoperiod insensitivity (Ppd) allele associations with establishment and early growth of wheat in contrasting production systems*, 166 Euphytica 249-267 (2009).
Office Action in corresponding Mexican Application No. MX/a/ 2015/002075, dated Oct. 25, 2019 (with translation).

\* cited by examiner

```
consensus    MKREYQDAGGSGGGGGMGSSEDKMMVS--AAAGEGEEVDELLAALGYKV
JF930277_R   ................-...............................
JF930278_R   ........................GS......................
JF930281_R   .................................................

51        61        71        81        91
consensus    RASDMADVAQKLEQLEMAMGMGGVGAGAAPDDSFATHLATDTVHYNPTDL
JF930277_R   ..................................................
JF930278_R   ..................................................
JF930281_R   ..................................................

101       111       121       131       141
consensus    SSWVESMLSELNAPPPPLPPAP-QLNASTSSTVTG-GGYFDLPPSVDSSC
JF930277_R   .....................Q............................
JF930278_R   ..................................................
JF930281_R   ...............................S............S 151       161       171       181       191
consensus    STYALRPIPSPAGAVAPADLSADS-VRDPKRMRTGGSSTSSSSSSSSSLG
JF930277_R   .............G....................................
JF930278_R   ..............--......V......................LG.
JF930281_R   .I.............T..................................

201       211       221       231       241
consensus    GGARSSVVEAAPPVAAAANA-PALPVVVVDTQEAGIRLVHALLACAEAVQ
JF930277_R   ................G.................................
JF930278_R   ................G.................................
JF930281_R   ................T.................................

251       261       271       281       291
consensus    QENFSAAEALVKQIPLLAASQGGAMRKVAAYFGEALARRVFRFRPQPDSS
JF930277_R   ..................................................
JF930278_R   ..................................................
JF930281_R   ...L..............................................

301       311       321       331       341
consensus    LLDAAFADLLHAHFYESCPYLKFAHFTANQAILEAFAGCRRVHVVDFGIK
JF930277_R   ..................................................
JF930278_R   ..................................................
JF930281_R   ..................................................

351       361       371       381       391
consensus    QGMQWPALLQALALRPGGPPSFRLTGVGPPQPDETDALQQVGWKLAQFAH
JF930277_R   ..................................................
JF930278_R   ..................................................
JF930281_R   ..................................................

401       411       421       431       441
consensus    TIRVDFQYRGLVAATLADLEPFMLQPEGEEDPNEEPEVIAVNSVFEMHRL
JF930277_R   ..................................................
JF930278_R   ..................................................
JF930281_R   ..................................................
```

Figure 7a

```
              451       461       471       481       491
consensus     LAQPGALEKVLGTVRAVRPRIVTVVEQEANHNSGTFLDRFTESLHYYSTM
JF930277_R    ..................................................
JF930278_R    ..................................................
JF930281_R    ..................................................

501       511       521       531       541
consensus     FDSLEGGSSGG-PSEVSSGAAAAPAAAGTDQVMSEVYLGRQICNVVACEG
JF930277_R    ..................................................
JF930278_R    ..................................................
JF930281_R    ............G.....................................

551       561       571       581       591
consensus     AERTERHETLGQWRNRLGNAGFETVHLGSNAYKQASTLLALFAGGDGYKV
JF930277_R    ..................................................
JF930278_R    ..................................................
JF930281_R    ..................................................

601       611       621
consensus     EEKEGCLTLGWHTRPLIATSAWRLAAP
JF930277_R    ...........................
JF930278_R    ...........................
JF930281_R    .........................G.
```

Figure 7b

```
Wheat Rht-B1a    22   EDKMVSGSAAAGEGEEVDELLAALGYKVRASDMADVAQKLEQLEMAMGMGGVGAGAAPD    81
                      + * ** + *  *  +****** +++++++++++++++++ *     +
CAA75492         11   DRKKTMMNEEDDGNG--MDELLAVLGYKVRSSEMADVAQKLEQLEVMM------SNVQED    62

Wheat Rht-B1a    82   DSFATHLATDTVHYNPTDLSSWVESMLSELNAPPPPLPPAPQLNASTSSTVTGGGYFDLP   141
                      D  + ****+******* ** ++++++++ *
CAA75492         63   D--LSQLATETVHYNPAELYTWLDSMLTDLNPP---------------------------   93

Wheat Rht-B1a   142   PSVDSSCSTYALRPIPSPAVAPADLSADSVVRDPKRMRTGGSSTSSSSSSSLGGGG----   198
                      ** + * ** +  ++                                 ++++++ ****
CAA75492         94   ----SSNAEYDLKAIPGDAIL-----------------------NQFAIDSASSNQGGGDTY  130

Wheat Rht-B1a   199   ---ARSSVVEAAPPVAAAGAPALPVVVVDTQEAGIRLVHALLACAEAVQQENFSAAEAL    255
                            *       *+++++++  *+++++++++++++++++++++++ + ****
CAA75492        131   TTNKRLKCSNGVVETTTATAESTRHVVLVDSQENGVRLVHALLACAEAVQKENLTVAEAL   190

Wheat Rht-B1a   256   VKQIPLLAASQGGAMRKVAAYFGEALARRVFRFRPQPDSSLLDAAFADLLHAHFYESCPY   315
                      **** ** ** ********* ** ********+   *  + +* *  ***** ++++
CAA75492        191   VKQIGFLAVSQIGAMRKVATYFAEALARRIYRL--SPSQSPIDHSLSDTLQMHFYETCPY   248

Wheat Rht-B1a   316   LKFAHFTANQAILEAFAGCRRVHVVDFGIKQGMQWPALLQALALRPGGPPSFRLTGVGPP   375
                      ****************** * +******** + +++++*********** ***+++++
CAA75492        249   LKFAHFTANQAILEAFQGKKRVHVIDFSMSQGLQWPALMQALALRPGGPPVFRLTGIGPP   308

Wheat Rht-B1a   376   QPDETDALQQVGWKLAQFAHTIRVDFQYRGLVAATLADLEPFMLQPEGEEDPNEEPEVIA   435
                      ** * +*** *  *   * +++**** ** *******  **     * ++ * * ++
CAA75492        309   APDNFDYLHEVGCKLAHLAEAIHVEFEYRGFVANTLADLDASML----ELRPS-EIESVA   363
```

Figure 8a

```
Wheat Rht-B1a  436  VNSVFEMHRLLAQPGALEKVLGTVRAVRPRIVTVVEQEANHNSGTFLDRFTESLHYYSTM  495
                    ********+*+* +******+****** *  ++* *  ****************+****
CAA75492       364  VNSVFELHKLLGRPGAIDKVLGVVNQIKPEIFTVVEQESNHNSPIFLDRFTESLHYYSTL  423

Wheat Rht-B1a  496  FDSLEGGSSGGPSEVSSGAAAAPAAAGTDQVMSEVYLGRQICNVVACEGAERTERHETLG  555
                    ****** *       *+++************+*************+ +* *******
CAA75492       424  FDSLEGVPS------------GQDKVMSEVYLGKQICNVVACDGPDRVERHETLS       466

Wheat Rht-B1a  556  QWRNRLGNAGFETVHLGSNAYKQASTLLALFAGGDGYKVEEKEGCLTLGWHTRPLIATSA  615
                    ***** *+****    +++******+***** ****** +**** ***************
CAA75492       467  QWRNRFGSAGFAAAHIGSNAFKQASMLLALFNGGEGYRVEESDGCLMLGWHTRPLIATSA  526

Wheat Rht-B1a  616  WRLA  619
                    * +++
CAA75492       527  WKLS  530
```

Figure 8b

WHEAT WITH NEW ALLELES OF RHT-B1

CROSS-REFERENCE TO RELATED APPLICATIONS

This application is a U.S. National Stage patent application pursuant to 35 U.S.C. § 371 of International Patent Application PCT/AU2013/000942, filed on Aug. 22, 2013, and published as WO 2014/028980 on Feb. 27, 2014, which claims priority to Australian Patent Application 2012903673 filed on Aug. 24, 2012, the content of each is hereby expressly incorporated by reference in their entireties for all purposes.

FIELD OF THE INVENTION

The present invention relates to overgrowth mutants of wheat which comprise an altered Rht-B1c allele. The present invention further relates to grain from such plants and to products derived from the grain.

BACKGROUND OF THE INVENTION

Plants respond to developmental, physiological, and environmental cues by adjustments in growth rate, either of parts or of the whole. Many mechanisms have been described that involve changes in either the content of the class of plant hormones gibberellins (GAs) (reviewed by Yamaguchi, 2008), or in signalling components that involve GAs such as the proteins GID1 and DELLA (reviewed by Sun, 2010). These result in dynamic regulation of GA signalling so that growth is coordinated with signalling from other hormonal regulatory pathways, and with environmental factors such as light, temperature and water availability (Hartweck, 2008; Achard and Genschik, 2009; Kuppusamy et al., 2009). Gating of GA signalling by the circadian clock has been proposed to account for diurnal differences in growth rate (Arana et al., 2011).

A variety of gibberellin (GA) mutants, either spontaneous in origin or identified after mutagenesis, have been characterized in plants. These include distinct dwarf and elongated ('slender') phenotypes that typically result from changes in either GA content or in GA signalling. The identification of the genes involved and the analysis of the proteins they encode has aided in developing an understanding of growth regulation by GA, particularly in the model species rice and Arabidopsis. Bioactive GAs bind to a GA receptor protein ('GID1', Ueguchi-Tanaka et al., 2005; Murase et al., 2008; Shimada et al., 2008) and form a complex that is then bound by DELLA proteins, which were identified as a sub-family of the GRAS transcription factor family (Griffiths et al., 2006; Willige et al., 2007; Hirano et al., 2010) that function as inhibitors of growth. In one case the evidence suggests that binding of DELLA to PIF transcription factors prevents them from promoting the expression of genes required for enhanced growth (de Lucas et al., 2008; Feng et al., 2008).

Della mutants in barley and rice are of particular interest because they include two markedly different phenotypes: highly elongated 'slender' types and 'GA insensitive' dwarfs. The former trait is recessive and characterised by an extreme GA response, whereas the latter is dominant or semi-dominant. Different single nucleotide substitutions in the Slender1 gene that encodes DELLA result in these radically different phenotypes ('elongated slender' or 'dwarf slender', Ikeda et al., 2001; Chandler et al., 2002; Asano et al., 2009). The former involves mutation that abolishes the capacity of DELLA to repress growth, and the latter is due DELLA accumulation because of failure to bind to the GA-GID1 complex.

Common wheat is hexaploid, and DELLA is encoded by three homoeologous genes (Rht-A1, Rht-B1, Rht-D1) on chromosomes 4AL, 4BS and 4DS of the wheat A, B and D genomes, respectively, where "L" indicates the long arm of the chromosome and "S" indicates the short arm of the chromosome. This has made study of mutants more difficult in wheat, and consequently less is known in wheat compared to rice and barley. 'GA-insensitive' semidwarfing alleles have been described for the B- and D-genomes (Peng et al., 1999; Pearce et al., 2011). One example of an extreme dwarfing allele is the Rht-B1c allele in the B genome which resulted from insertion of a DNA element. Most of this insertion was predicted to be spliced from the transcript of the gene, but 90 nucleotides remained and resulted in a predicted 30 amino acid in-frame insertion in DELLA (Pearce et al., 2011; Wu et al., 2011).

Semidwarfing genes have been prominent in wheat and rice breeding since the Green Revolution because of their beneficial effects on crop yield. The modest (10-20%) reduction in height of semidwarfs was due to a deficiency in growth promotion by endogenous GA. In rice this resulted from mutation in a GA biosynthetic gene, so that less active GA was present (Monna et al., 2002; Sasaki et al., 2002; Spielmeyer et al., 2002). In contrast, in wheat dwarfing mutations in the Della gene resulting in growth that was relatively 'insensitive' to GA (Peng et al., 1999). The original semidwarfing mutations were spontaneous in origin, and their agronomic importance is evident from their continuing widespread use in current varieties some 50 years after their first introduction. However, the existing Rht alleles have some disadvantages.

There remains, therefore, a need for improved semi-dwarf wheat varieties.

SUMMARY OF THE INVENTION

In a first aspect the present invention provides a wheat plant comprising an Rht-B1 allele which encodes an Rht-B1 polypeptide, the polypeptide comprising an N-terminal domain and a C-terminal domain, wherein the amino acid sequence of the C-terminal domain is at least 98% identical to amino acids 50-621 of SEQ ID NO:5, and wherein the amino acid sequence of the Rht-B1 polypeptide differs from the sequence set forth as SEQ ID NO:5 by at least (i) an insertion of one or more amino acids between amino acids 49 and 50 of SEQ ID NO:5, and (ii) one or more amino acid substitutions in the C-terminal domain relative to amino acids 50-621 of SEQ ID NO:5.

In a second aspect the present invention provides a wheat plant comprising an Rht-B1 allele which encodes an Rht-B1 polypeptide, the polypeptide comprising an N-terminal domain and a C-terminal domain, wherein the amino acid sequence of the C-terminal domain is at least 98% identical to amino acids 50-621 of SEQ ID NO:5, wherein the amino acid sequence of the Rht-B1 polypeptide differs from the sequence set forth as SEQ ID NO:5 by at least an insertion of one or more amino acids between amino acids 49 and 50 of SEQ ID NO:5, and wherein the nucleotide sequence of the Rht-B1 allele differs from the nucleotide sequence set forth as SEQ ID NO:1 at least by the presence of an intron splice site mutation.

In a third aspect the present invention provides wheat grain comprising an Rht-B1 allele which encodes an Rht-B1 polypeptide, the polypeptide comprising an N-terminal domain and a C-terminal domain, wherein the amino acid sequence of the C-terminal domain is at least 98% identical to amino acids 50-621 of SEQ ID NO:5, and wherein the amino acid sequence of the Rht-B1 polypeptide differs from the sequence set forth as SEQ ID NO:5 by at least (i) an insertion of one or more amino acids between amino acids 49 and 50 of SEQ ID NO:5, and (ii) one or more amino acid substitutions in the C-terminal domain relative to amino acids 50-621 of SEQ ID NO:5.

In a fourth aspect the present invention provides a wheat grain comprising an Rht-B1 allele which encodes an Rht-B1 polypeptide, the polypeptide comprising an N-terminal domain and a C-terminal domain, wherein the amino acid sequence of the C-terminal domain is at least 98% identical to amino acids 50-621 of SEQ ID NO:5, wherein the amino acid sequence of the Rht-B1 polypeptide differs from the sequence set forth as SEQ ID NO:5 by at least an insertion of one or more amino acids between amino acids 49 and 50 of SEQ ID NO:5, and wherein the nucleotide sequence of the Rht-B1 allele differs from the nucleotide sequence set forth as SEQ ID NO:1 at least by the presence of an intron splice site mutation.

In a fifth aspect the present invention provides a wheat cell comprising an Rht-B1 allele which encodes an Rht-B1 polypeptide, the polypeptide comprising an N-terminal domain and a C-terminal domain, wherein the amino acid sequence of the C-terminal domain is at least 98% identical to amino acids 50-621 of SEQ ID NO:5, and wherein the amino acid sequence of the Rht-B1 polypeptide differs from the sequence set forth as SEQ ID NO:5 by at least (i) an insertion of one or more amino acids between amino acids 49 and 50 of SEQ ID NO:5, and (ii) one or more amino acid substitutions in the C-terminal domain relative to amino acids 50-621 of SEQ ID NO:5. In a preferred embodiment, the wheat cell is a wheat endosperm cell. Such wheat endosperm cells are not able to be regenerated into a wheat plant.

In a sixth aspect the present invention provides a wheat cell comprising an Rht-B1 allele which encodes an Rht-B1 polypeptide, the polypeptide comprising an N-terminal domain and a C-terminal domain, wherein the amino acid sequence of the C-terminal domain is at least 98% identical to amino acids 50-621 of SEQ ID NO:5, wherein the amino acid sequence of the Rht-B1 polypeptide differs from the sequence set forth as SEQ ID NO:5 by at least an insertion of one or more amino acids between amino acids 49 and 50 of SEQ ID NO:5, and wherein the nucleotide sequence of the Rht-B1 allele differs from the nucleotide sequence set forth as SEQ ID NO:1 at least by the presence of an intron splice site mutation. In a preferred embodiment, the wheat cell is a wheat endosperm cell. Such wheat endosperm cells are not able to be regenerated into a wheat plant.

In a seventh aspect the present invention provides a nucleic acid molecule which encodes an Rht-B1 polypeptide, the polypeptide comprising an N-terminal domain and a C-terminal domain, wherein the amino acid sequence of the C-terminal domain is at least 98% identical to amino acids 50-621 of SEQ ID NO:5, and wherein the amino acid sequence of the Rht-B1 polypeptide differs from the sequence set forth as SEQ ID NO:5 by at least (i) an insertion of one or more amino acids between amino acids 49 and 50 of SEQ ID NO:5, and (ii) one or more amino acid substitutions in the C-terminal domain relative to amino acids 50-621 of SEQ ID NO:5. Such nucleic acid molecules are not naturally occurring. The nucleic acid molecule may be isolated or as a transgene in a transgenic plant.

In an eighth aspect the present invention provides a nucleic acid molecule which encodes an Rht-B1 polypeptide, the polypeptide comprising an N-terminal domain and a C-terminal domain, wherein the amino acid sequence of the C-terminal domain is at least 98% identical to amino acids 50-621 of SEQ ID NO:5, wherein the amino acid sequence of the Rht-B1 polypeptide differs from the sequence set forth as SEQ ID NO:5 by at least an insertion of one or more amino acids between amino acids 49 and 50 of SEQ ID NO:5, and wherein the nucleotide sequence of the Rht-B1 allele differs from the nucleotide sequence set forth as SEQ ID NO:1 at least by the presence of an intron splice site mutation. Such nucleic acid molecules are not naturally occurring. The nucleic acid molecule may be isolated or as a transgene in a transgenic plant.

In a ninth aspect the present invention provides an Rht-B1 polypeptide, comprising an N-terminal domain and a C-terminal domain, wherein the amino acid sequence of the C-terminal domain is at least 98% identical to amino acids 50-621 of SEQ ID NO:5, and wherein the amino acid sequence of the Rht-B1 polypeptide differs from the sequence set forth as SEQ ID NO:5 by at least (i) an insertion of one or more amino acids between amino acids 49 and 50 of SEQ ID NO:5, and (ii) one or more amino acid substitutions in the C-terminal domain relative to amino acids 50-621 of SEQ ID NO:5.

In a tenth aspect the present invention provides an isolated oligonucleotide which comprises at least 19 contiguous nucleotides of a polynucleotide of the seventh or eighth aspect of the present invention, wherein the 19 contiguous nucleotides includes at least one of the nucleotide substitutions selected from the group consisting of G2715A, G2726A, G2747A, G2829A, G2831A, G2849A, C2865T, C2966T, C2972T, C3065A, C3117T, G3477A, C3507T, C3519T, G3624A, G2792A, CC2108TA, G3047A, G2864A, G3671A, G148A, G148T, G147A, G2084A and G2083A, with reference to SEQ ID NO:1, or which is fully complementary thereto.

BRIEF DESCRIPTION OF FIGURES

FIG. 7: ClustalW alignment of amino acid sequences encoded by Rht-A1a (JF930277) (SEQ ID NO: 9), Rht-B1 (JF930278) (SEQ ID NO: 5) and Rht-D1a (JF930281) (SEQ ID NO: 11) in wheat with consensus sequence shown (SEQ ID NO: 31).

FIG. 8: Alignment of wheat Rht-B1a polypeptide (SEQ ID NO: 5, upper sequence) and *Arabidopsis thaliana* GAI protein (Accession No. CAA75492, SEQ ID NO: 13, lower sequence) by Blastp. Asterisks indicate amino acids which are identical (conserved) between the two polypeptides, and "+" symbols indicate similar but not identical amino acids.

NOTES ON THE SEQUENCE LISTING

Figure 1:
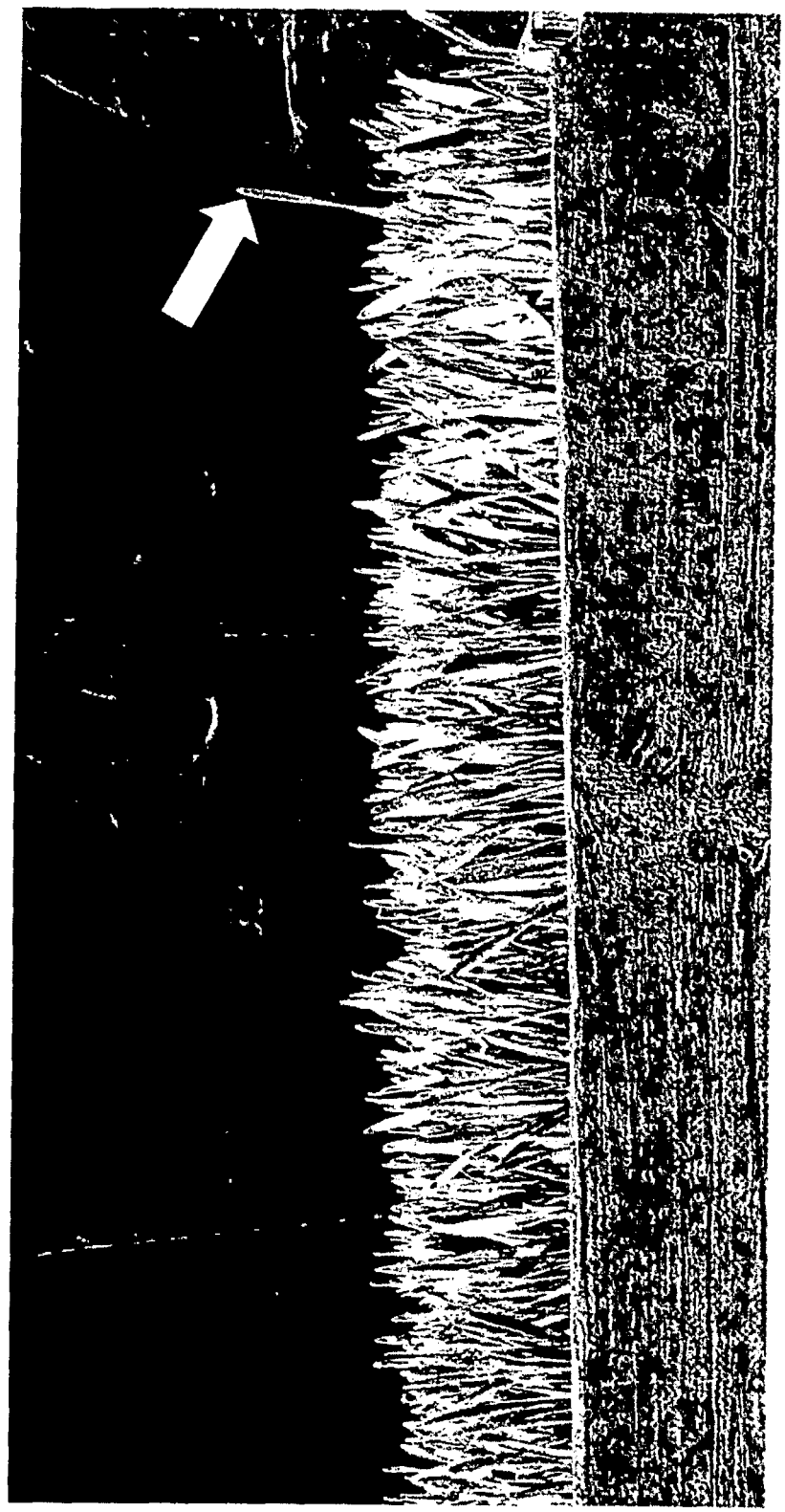
FIG. 1: Example of isolation of wheat overgrowth mutants by screening in flats. One mutant seedling characterized by increased growth rates is arrowed.

SEQ ID NO:1 shows the 3892nt nucleotide sequence of the Rht-B1c gene from Maringa/Rht-B1c, starting at the ATG of the protein coding region to the TGA at the end of the coding region. The 2026nt insertion of the retrotransposon into the Rht-B1 gene to generate Rht-B1c occurs immediately after the first 147nt.

SEQ ID NO:2 shows the 1956nt nucleotide sequence of the cDNA corresponding to the Rht-B1c allele in wheat Maringa/Rht-B1c. The sequence is almost identical to the nucleotide sequence provided in Genbank Accession No. JN857971 (Wu et al., 2011), differing only by 2 nucleotides at positions 813 and 1851. The 90nt insertion in the cDNA relative to the cDNA from the Rht-B1a allele corresponds to nucleotides 148-237 of SEQ ID NO: 2.

SEQ ID NO:3 shows the amino acid sequence of the 651 amino acid polypeptide encoded by the Rht-B1c allele i.e. encoded by the gene having the nucleotide sequence of SEQID NO: 1 and the cDNA of SEQ ID NO: 2. The 30-amino acid insertion into the polypeptide relative to the Rht-B1a polypeptide are amino acids 50-79 of SEQ ID NO:3.

SEQ ID NO:4 shows the nucleotide sequence of the cDNA corresponding to the Rht-B1a (wild-type) allele, starting at the ATG translation start codon (Pearce et al., 2011) (Genbank Accession No. JF930278).

SEQ ID NO:5 shows the amino acid sequence of the Rht-B1a polypeptide (wild-type) (Genbank Accession No JF930278), 621 amino acids.

SEQ ID NO:6 shows the 7057nt nucleotide sequence of the *Triticum aestivum* Rht1-B1b gene for (Genbank Accession No. FN649763) from cultivar Xiaoyan54. Nucleotides 1-2136 correspond to the promoter and 5'UTR of Rht-B1b, nucleotides 2137-4002 correspond to the protein coding region which is interrupted by the C to T nucleotide change at position 2326 relative to the wild-type, and nucleotides 4003-7057 correspond to the 3'UTR of Rht-B1b and the region 3' of the gene.

SEQ ID NO:7 shows the 555 amino acid sequence of the polypeptide encoded by Rht-B1b, which is an N-terminal truncated Rht-B1 protein, having the first 66 amino acids truncated relative to the wild-type Rht-B1a. Translation re-initiates with amino acid 67.

SEQ ID NO:8 shows the 3463nt nucleotide sequence of the *Triticum aestivum* Rht-A1a gene (wild-type Rht-A1), (Genbank Accession No. JF930277) Nucleotides 1-1600 correspond to the promoter and 5'UTR of Rht-A1a, and nucleotides 1601-3463 correspond to the protein coding region of Rht-A1a. The protein coding region is 96% identical to the Rht-B1a coding region.

SEQ ID NO:9 shows the 620 amino acid sequence of the Rht-A1a (wild-type) polypeptide.

SEQ ID NO:10 shows the 1872 nucleotide sequence of a cDNA corresponding to the Rht-D1a gene (Genbank Accession No AJ242531).

SEQ ID NO:11 shows the 623 amino acid sequence of the Rht-D1 polypeptide (Accession No. JF930281).

SEQ ID NO:12 shows the 618 amino acid sequence of the barley Sln1 gene (Accession No. AK372064).

SEQ ID NO:13 shows the 532 amino acid sequence of the *Arabidopsis thaliana* GAI polypeptide (Accession No. CAA75492).

SEQ ID NO:14 shows the amino acid sequence of the 30 amino acid insertion n to the Rht-B1c polypeptide.

SEQ ID NO:15 shows the 11 amino acid sequence of the "Della" motif in the wild-type Rht-B1a polypeptide in wheat, which is interrupted in the Rht-B1c polypeptide.

SEQ ID NO:16 shows the nucleotide sequence of the Rht-B1c gene (Accession No. JN857970, Wu et al., 2011). The cDNA corresponds to nucleotides 206 to 352 joined to 2289 to 4097.

SEQ ID NOs:17-30 show the nucleotide sequences of oligonucleotide primers.

DETAILED DESCRIPTION OF THE INVENTION

Plants

The present invention provides wheat plants, parts thereof such as wheat grain, products obtained from these plants and grain such as food ingredients and food products, and methods of producing and using the same. As used herein, the term "wheat" means a plant, plant part, grain or product derived therefrom of the species *Triticum aestivum* L. or *Triticum turgidum* ssp. durum or *Triticale*. *Triticum aestivum* L., also know as breadwheat, is a hexaploid wheat which has a genome organization of AABBDD, comprised of 42 chromosomes. The "A", "B" and "D" subgenomes of *Triticum aestivum* L. are often referred to as "genomes". *Triticum turgidum* ssp. durum, often referred to as durum wheat is a tetraploid wheat which has a genome organization of AABB, having 28 chromosomes. Diploid progenitors of hexaploid or tetraploid wheat include *Triticum* sp. such as *T. uartu*, *T. monococcum* or *T. boeoticum* for the A genome, *Aegilops speltoides* for the B genome, and *T. tauschii* (also known as *Aegilops squarrosa* or *Aegilops tauschii*) for the D genome, but are not encompassed in "wheat" as used herein. However, plants that are produced by conventional techniques using *Triticum aestivum* L. as a parent in a sexual cross with the non-*Triticum* species Secale cereale (rye), which hybrid progeny are referred to herein as Triticale, are encompassed in "wheat" as used herein. Preferably, the wheat plant is suitable for commercial production of grain, such as commercial varieties of breadwheat or durum wheat, having suitable agronomic characteristics which are known to those skilled in the art.

In a first aspect, the present invention provides a wheat plant comprising an Rht-B1 allele which encodes a variant (non-wild-type) Rht-B1 polypeptide, preferably is homozygous for the Rht-B1 allele. In embodiments the wheat plant comprises an Rht-B1 allele selected from the group consisting of Rht-B1c.1, Rht-B1c.2, Rht-B1c.3, Rht-B1c.4, Rht-B1c.5, Rht-B1c.6, Rht-B1c.7, Rht-B1c.8, Rht-B1c.9, Rht-B1c.10, Rht-B1c.12, Rht-B1c.15, Rht-B1c.16, Rht-B1c.17, Rht-B1c.18, Rht-B1c.21, Rht-B1c.22, Rht-B1c.23, Rht-B1c.24, Rht-B1c.26, Rht-B1c.27, Rht-B1c.28, Rht-B1c.29, Rht-B1c.30 and Rht-B1c.32, and is preferably homozygous for the allele. In preferred embodiments, the wheat plant comprises an Rht-B1 allele selected from the group consisting of Rht-B1c.22, Rht-B1c.23, Rht-B1c.24 and Rht-B1c.26 and is preferably homozygous for the allele. In an embodiment, the Rht-B1 polypeptide comprises an N-terminal domain and a C-terminal domain, wherein the amino acid sequence of the C-terminal domain is at least 98% identical to amino acids 50-621 of SEQ ID NO:5, and wherein the amino acid sequence of the Rht-B1 polypeptide differs from the sequence set forth as SEQ ID NO:5 by at least (i) an insertion of one or more amino acids between amino acids 49 and 50 of SEQ ID NO:5, and (ii) one or more amino acid substitutions in the C-terminal domain relative to amino acids 50-621 of SEQ ID NO:5. SEQ ID NO:5 sets forth the amino acid sequence of a wild-type wheat Rht-B1a protein, with a length of 621 amino acids, which is encoded by a wild-type Rht-B1a allele in wheat, and which is used herein as the reference sequence for a wild-type Rht-B1 polypeptide.

Alternatively, the amino acid sequence of the variant Rht-B1 polypeptide differs from the sequence set forth as SEQ ID NO:5 by at least an insertion of one or more amino acids between about amino acids 49 and 50 of SEQ ID NO:5 and the nucleotide sequence of the Rht-B1 allele encoding the variant Rht-B1 polypeptide differs from the nucleotide sequence set forth as SEQ ID NO:1 at least by the presence of a mutation at or adjacent to an intron splice site such that intron splicing of the RNA transcript of the Rht-B1 allele is affected. As used herein, an "intron splice site" means the 4 nucleotides spanning the intron junction, namely the 2 nucleotides to the 5' and the 2 nucleotides to the 3' side of the intron junction. As used herein, "adjacent to an intron splice site" means the 3 nucleotides to the 5' and the 3 nucleotides to the 3' side of the intron splice site. SEQ ID NO:1 sets forth the nucleotide sequence of the protein coding region of the Rht-B1c allele, derived from the wheat variety Maringa genetic background, starting at the translation initiation ATG to the translation termination codon TGA. SEQ ID NO:1 includes the 2026 nucleotide retrotransposon insertion (nucleotides 148-2173) which was inserted into the Rht-B1 gene to form the Rht-B1c allele (Wu et al., 2011). In this embodiment, the amino acid sequence of the polypeptide encoded by the Rht-B1 allele may be identical to SEQ ID NO:3, or it may be different. The Rht-B1 allele may comprise both the intron splicing mutation and encode a polypeptide having the differences of (i) and (ii) in the previous paragraph, or in a preferred embodiment, the polypeptide has the differences of (i) and (ii) above and is lacking any intron splice site mutation.

As used herein, "an Rht-B1 polypeptide" means a polypeptide which is encoded by an Rht-B1 allele in wheat. Typically, the Rht-B1 polypeptide has an N-terminal domain joined to a C-terminal domain of about 572 amino acids that is at least 98% identical in amino acid sequence to amino acids 50-621 of SEQ ID NO:5. The C-terminal domain includes what is commonly referred to as the GRAS domain. In an embodiment, the N-terminal domain is about 49 to about 79 amino acids in length. In a preferred embodiment, the N-terminal domain is about 79 amino acids in length having a sequence such as, for example, amino acids 1-79 of SEQ ID NO:3 or a variant with 1 to 5 amino acid substitutions with reference to amino acids 1-79 of SEQ ID NO:3. In an alternative embodiment, the Rht-B1 polypeptide is derived from the wild-type Rht-B1 polypeptide by a truncation at the N-terminal end such as, for example, the Rht-B1b polypeptide (SEQ ID NO:7) encoded by the Rht-B1b allele, also known as the Rht1 gene. In an embodiment, the Rht-B1 allele encodes an Rht-B1 polypeptide whose amino acid sequence is at least 98% identical with SEQ ID NO:3.

In an embodiment, the amino acid sequence of the Rht-B1 polypeptide is not identical to SEQ ID NO:5 and is not identical to SEQ ID NO:7, although it may encompass SEQ ID NO:7. In an embodiment, if the amino acid sequence of the polypeptide is identical to SEQ ID NO:3, then the Rht-B1 allele does not have the nucleotide sequence set forth as SEQ ID NO:1; instead it encodes a sequence variant of SEQ ID NO:1 having a mutation at or adjacent to an intron splicing site relative to SEQ ID NO: 1. In a preferred embodiment, the amino acid sequence of the polypeptide is not identical to SEQ ID NO:3. That is, the polypeptide is different in sequence to each of the Rht-B1a (wild-type) polypeptide, the Rht-B1b polypeptide and the Rht-B1c polypeptide. In an embodiment, the amino acid sequence of the polypeptide differs from the Rht-B1a amino acid sequence set forth as SEQ ID NO:5 by at least (i) an insertion of one or more amino acids between amino acids 49 and 50 of SEQ ID NO:5, and (ii) one or more amino acid substitutions in a region of the polypeptide corresponding to amino acids 200 to 621 of SEQ ID NO:5. This region of the Rht-B1a polypeptide corresponds to the GRAS domain of the polypeptide.

In a preferred embodiment, the insertion relative to the Rht-B1a polypeptide ((i) above) of one or more amino acids between amino acids 49 and 50 of SEQ ID NO:5 is an insertion of about 30 amino acids, whose sequence is preferably DSATPPDAPLVAAAGLAANETTHIKISANK (SEQ ID NO: 14; corresponding to amino acids 50 to 79 of SEQ ID NO:3) or a variant thereof, wherein the sequence of the variant differs from SEQ ID NO:14 by amino acid substitutions, insertions or deletions of no more than 5 amino acids, preferably of 1 or 2 amino acid substitutions. The sequence DSATPPDAPLVAAAGLAANETTHIKISANK (SEQ ID NO:14) is the sequence of the insertion in the Rht-B1c polypeptide relative to the Rht-B1a polypeptide. This insertion of 30 amino acids resulted from the insertion into the Rht-B1 gene that formed the Rht-B1c allele. This insertion is within the so called DELLA motif (DELLAALGYKV; SEQ ID NO:15) of the Rht-B1 polypeptide which is thought to be required for interaction with the GA receptor protein, GID1, such that the polypeptide with the insertion no longer binds GID1. Variations of this inserted sequence may be obtained through mutagenesis, and substitutions, insertions or deletions of 1 to 5 amino acids are not expected to affect the loss of the interaction of the polypeptide with GID1.

In an embodiment, the polypeptide of the wheat plant further comprises one or more amino acid substitutions, preferably conservative amino acid substitutions, in a region of the polypeptide corresponding to amino acids 1 to 200 of SEQ ID NO:5, also referred to as the DELLA domain of the wild-type Rht-B1 polypeptide because it comprises the amino acid sequence DELLAALGYKV (SEQ ID NO:15), also referred to as the DELLA motif. It is preferred however, that the amino acid sequence of the Rht-B1 polypeptide of the invention is identical to SEQ ID NO:3 in the mutated DELLA domain, i.e. comprises amino acids 1-230 of SEQ ID NO:3.

In further preferred embodiments, the one or more amino acid substitutions in the C-terminal domain are in the region of the polypeptide corresponding to amino acids 200 to 621 of SEQ ID NO:5. In a preferred embodiment, the one or more amino acid substitutions comprise a substitution of an amino acid selected from the group consisting of G260, V264, A271, G298, A299, A305, A310, P344, L346, G377, P394, R514, T524, S528, G563, V286, D371, A310, E579, S493, R283, R271, G274, A280, V234, R484, V285, G230, S488 and C240 with reference to SEQ ID NO:3. It is preferred that the substitution is selected from the group consisting of G260E, V264M, A271T, G298D, A299T, A305T, A310V, P344S, L346F, G377R, P394L, R514H, T524I, S528F, G563D, V286M, D371N, A310T, E579K, S493F, R283H, R271H, G274D, A280T, V234M, R484H, V285F, G230E, S488F and C240Y. In a more preferred embodiment, the Rht-B1 allele of the wheat plant comprises a sequence variation relative to SEQ ID NO:1, which sequence variation is selected from the group consisting of G2715A, G2726A, G2747A, G2829A, G2831A, G2849A, C2865T, C2966T, C2972T, G3065A, C3117T, G3477A, C3507T, C3519T, G3624A, G2792A, CC2108TA, G3047A, G2864A, G3671A, G148A, G148T, G147A, G2084A and G2083A. These sequence variations correspond to the amino acid substitutions listed immediately above, see Table 3.

It is preferred that the wheat plant of the invention has an increased plant height relative to a wheat plant which is homozygous for the Rht-B1c allele and a decreased height relative to a wheat plant which is homozygous for the Rht-B1a allele when the plants are grown under the same conditions. Accordingly the wheat plant of the invention is referred to as "semi-dwarf". In a preferred embodiment, the height of the wheat plant of the invention is between about 70% and about 94% of the height of the control plant which is homozygous for the Rht-B1a allele ("tall phenotype"), more preferably between about 75% and about 90% of the height of the plant which is homozygous for the Rht-B1a allele. In comparison, the height of the wheat plant which is homozygous for the Rht-B1c allele ("dwarfed plant") is about 42% of the height of the plant which is homozygous for the Rht-B1a allele. The height of the wheat plant of the invention may be about the same or essentially the same as the height of a wheat plant which is homozygous for the Rht-B1b allele, which is about 80-81% of the height of the tall plants, or may be less than the height of the Rht-B1b plant, or greater than the height of the Rht-B1b plant. "Plant height" as used herein means the height of the mature plant from ground level to the top of the tallest stem, i.e. to the base of the head. The plants which are homozygous for the Rht-B1c, Rht-B1a or Rht-B1b alleles and which are used as controls in the comparison preferably have essentially the same genetic background, more preferably are near-isogenic lines, relative to the wheat plant of the invention; they are therefore termed a "corresponding wheat plant which is homozygous for the Rht-B1c (or Rht-B1a or Rht-B1b) allele". Those skilled in the art are readily able to select a corresponding wheat plant which is suitable for the comparison. To make the comparison, the plant of the invention and the control plant are grown under essentially the same timing and environmental conditions, such as in a replicated field trial, including the same temperature regime, light conditions, nutrient and water supply and soil conditions. Preferably the plant height is measured for field grown plants, although glasshouse grown plants may also be used for the comparison, and grown according to field trials as known in the art. The plant heights may be measured at any point in the growth cycle, but are preferably measured at maturity of the plants.

In addition it is preferred that the wheat plant has increased fertility and/or produces an increased amount of grain relative to the wheat plant which is homozygous for the Rht-B1c allele and/or has increased coleoptile length relative to the wheat plant which is homozygous for the Rht-B1c allele and/or is capable of producing grain which has increased dormancy relative to grain obtained from the wheat plant which is homozygous for the Rht-B1a allele. Preferably, the amount of grain produced by the plant is essentially the same as, or greater than, a corresponding wheat plant which is homozygous for the Rht-B1b allele. As used herein, "fertility" is defined as the number of grains per head, and the "amount of grain" or "yield of grain produced from a plant" means the weight of mature grain that can be harvested from the plant. Such grain typically has a moisture content of about 10% to about 15% by weight. The wheat plants of the present invention also preferably have increased coleoptile length relative to a wheat plant which is homozygous for the Rht-B1c allele. Preferably the coleoptile length of the wheat plant of the present invention is between 70% and 120%, preferably between 80% and 100% of the coleoptile length of the plant which is homozygous for the Rht-B1a allele. Another preferred trait of the wheat plants of the present invention is dormancy of the grain obtained from the plant. It is preferred that the plants have increased grain dormancy relative to a wheat plant which is homozygous for the Rht-B1a allele. Preferably the wheat plant has between 50% and 100%, preferably 60% to 100%, of the level of dormancy of a wheat plant which is homozygous for the Rht-B1c allele. In an embodiment, the rate of germination of grain obtained from the wheat plant of the invention is intermediate between that of grain from a wheat plant which is homozygous for the Rht-B1a allele and grain from a wheat plant which is homozygous for the Rht-B1c allele. The rate of germination may be assayed as described in Example 1. For example, the time taken for populations of grains to reach 50% germination may be assayed. In a preferred embodiment, the grain of the wheat plant of the invention requires between 1 and 8 weeks longer, preferably between 2 and 5 weeks longer, of storage at room temperature ("after-ripening period") for the rate of germination to reach 50% relative to grain from a corresponding wheat plant which is homozygous for the Rht-B1a allele.

As would be understood, where a comparison is made between the plants or grain of the present invention and those which are homozygous for the Rht-B1c allele or are homozygous for the Rht-B1a allele, the comparison is performed with plants grown under essentially identical growing conditions, growth time, temperature, water and nutrient supply, etc, and for grain obtained from such plants.

Grain In a second aspect, the invention provides wheat grain which is obtained from, or obtainable from, or which is part of, the wheat plants of the invention. As used herein, "grain" means grain as is typically harvested by farmers from mature wheat plants growing in the field, including grain used for food production or in food products, and germinated grain after it has been sowed but before emergence of seedlings. Grain also includes grain which has been processed for food production or which is an ingredient in a food product. The harvested wheat grain of the invention typically has a moisture content of about 10% to about 15% by weight. In an embodiment, the wheat grain comprises an Rht-B1 allele which encodes a variant (non-wild-type) Rht-B1 polypeptide, preferably the grain is homozygous for the allele. In an embodiment, the Rht-B1 polypeptide comprises an N-terminal domain and a C-terminal domain, wherein the amino acid sequence of the C-terminal domain is at least 98% identical to amino acids 50-621 of SEQ ID NO:5, and wherein the amino acid sequence of the Rht-B1 polypeptide differs from the sequence set forth as SEQ ID NO:5 by at least (i) an insertion of one or more amino acids between amino acids 49 and 50 of SEQ ID NO:5, and (ii) one or more amino acid substitutions in the C-terminal domain relative to amino acids 50-621 of SEQ ID NO:5. In embodiments the wheat grain comprises an Rht-B1 allele selected from the group consisting of Rht-B1c.1, Rht-B1c.2, Rht-B1c.3, Rht-B1c.4, Rht-B1c.5, Rht-B1c.6, Rht-B1c.7, Rht-B1c.8, Rht-B1c.9, Rht-B1c.10, Rht-B1c.12, Rht-B1c.15, Rht-B1c.16, Rht-B1c.17, Rht-B1c.18, Rht-B1c.21, Rht-B1c.22, Rht-B1c.23, Rht-B1c.24, Rht-B1c.26, Rht-B1c.27, Rht-B1c.28, Rht-B1c.29, Rht-B1c.30 and Rht-B1c.32, and is preferably homozygous for the allele. In preferred embodiments, the wheat grain comprises an Rht-B1 allele selected from the group consisting of Rht-B1c.22, Rht-B1c.23, Rht-B1c.24 and Rht-B1c.26 and is preferably homozygous for the allele.

Alternatively, the amino acid sequence of the variant Rht-B1 polypeptide of the grain differs from the sequence set forth as SEQ ID NO:5 by at least an insertion of one or more amino acids between amino acids 49 and 50 of SEQ ID NO:5 and the nucleotide sequence of the Rht-B1 allele encoding the variant Rht-B1 polypeptide differs from the nucleotide sequence set forth as SEQ ID NO:1 at least by the presence of a mutation at or adjacent to an intron splice site such that intron splicing of the RNA transcript of the Rht-B1 allele is affected. In this embodiment, the amino acid sequence of the polypeptide encoded by the Rht-B1 allele may be identical to SEQ ID NO:3, or it may be different. The Rht-B1 allele may comprise both the intron splicing mutation and encode a polypeptide having the differences of (i) and (ii) in the previous paragraph, or in a preferred embodiment, the polypeptide has the differences of (i) and (ii) above and is lacking any intron splice site mutation relative to SEQ ID NO:1.

The variant Rht-B1 polypeptide of the grain and the Rht-B1 allele encoding it may be further defined as described in the paragraphs above with respect to the wheat plant. In a preferred embodiment, the grain has increased dormancy relative to grain obtained from a wheat plant which is homozygous for the Rht-B1a allele. In an embodiment, the rate of germination of grain of the invention is intermediate between that of grain from a wheat plant which is homozygous for the Rht-B1a allele and grain from a wheat plant which is homozygous for the Rht-B1c allele. The rate of germination may be assayed as described in Example 1. For example, the time taken for populations of grains to reach 50% germination may be assayed. In a preferred embodiment showing "increased dormancy", the grain of the invention requires between 1 and 8 weeks longer, preferably between 2 and 5 weeks longer, of storage at room temperature ("after-ripening period") for the rate of germination to reach 50% relative to grain from a corresponding wheat plant which is homozygous for the Rht-B1a allele. It is also preferred that the wheat grain of the invention is capable of growing into a wheat plant when the grain is sown into soil, which plant has an increased height relative to a wheat plant which is homozygous for the Rht-B1c allele and a decreased height relative to a wheat plant which is homozygous for the Rht-B1a allele when the plants are grown under the same conditions. The wheat plant arising from the grain may have increased fertility and/or produces an increased amount of grain relative to the wheat plant which is homozygous for the Rht-B1c allele and/or has increased coleoptile length relative to the wheat plant which is homozygous for the Rht-B1c allele.

The present invention also provides a method of producing grain of the invention, the method comprising (i) growing a wheat plant of the present invention and (ii) harvesting grain from the plant. In some embodiments the wheat grain has been processed so that it is no longer able to germinate. This may be achieved by removal of the embryo from the seed, for example by milling, or by heat treatment or other processing of the grain. The grain may be kibbled, cracked, par-boiled, rolled, pearled, milled or ground grain.

The present invention also provides a method of producing flour, wholemeal, starch, starch granules or bran, the method comprising obtaining the grain of the present invention and processing the grain to produce the flour, wholemeal, starch, starch granules or bran. Such processing methods are well known in the art. The step of obtaining the grain may comprise, for example, harvesting grain from a wheat plant of the invention or purchasing the grain.

The present invention also provides products produced from the plants or grain of the present invention, such as a food product, which may be a food ingredient. Examples of food products include flour, starch, leavened or unleavened breads, pasta, noodles, animal fodder, breakfast cereals, snack foods, cakes, malt, pastries and foods containing flour-based sauces. The food product may be a bagel, a biscuit, a bread, a bun, a croissant, a dumpling, an English muffin, a muffin, a pita bread, a quickbread, a refrigerated/frozen dough product, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food. The food product may be prepared by mixing the grain, or flour, wholemeal or bran from said grain, with another ingredient. Another product is animal feed such as harvested grain, hay, straw or silage. The plants of the invention may be used directly as animal feed, for example when growing in the field.

Polynucleotides In a third aspect the present invention provides a nucleic acid molecule which encodes an Rht-B1 polypeptide of the invention. The nucleic acid molecule may be isolated from a wheat plant or comprised in a wheat plant or as an exogenous nucleic acid molecule in a plant, which may be any plant such as a cereal plant or a plant other than wheat. In an embodiment, the Rht-B1 polypeptide comprises an N-terminal domain and a C-terminal domain, wherein the amino acid sequence of the C-terminal domain is at least 98% identical to amino acids 50-621 of SEQ ID NO:5, and wherein the amino acid sequence of the Rht-B1 polypeptide differs from the sequence set forth as SEQ ID NO:5 by at least (i) an insertion of one or more amino acids between amino acids 49 and 50 of SEQ ID NO:5, and (ii) one or more amino acid substitutions in the C-terminal domain relative to amino acids 50-621 of SEQ ID NO:5. The Rht-B1 polypeptide of the invention may be further defined as described in the paragraphs above with respect to the wheat plant. In preferred embodiments the nucleic acid molecule comprises an Rht-B1 allele selected from the group consisting of Rht-B1c.1, Rht-B1c.2, Rht-B1c.3, Rht-B1c.4, Rht-B1c.5, Rht-B1c.6, Rht-B1c.7, Rht-B1c.8, Rht-B1c.9, Rht-B1c.10, Rht-B1c.12, Rht-B1c.15, Rht-B1c.16, Rht-B1c.17, Rht-B1c.18, Rht-B1c.21, Rht-B1c.22, Rht-B1c.23, Rht-B1c.24, Rht-B1c.26, Rht-B1c.27, Rht-B1c.28, Rht-B1c.29, Rht-B1c.30, and Rht-B1c.32. In more preferred embodiments, the nucleic acid molecule comprises an Rht-B1 allele selected from the group consisting of Rht-B1c.22, Rht-B1c.23, Rht-B1c.24 and Rht-B1c.26.

Polypeptides In a fourth aspect the present invention provides an Rht-B1 polypeptide which comprises an N-terminal domain and a C-terminal domain, wherein the amino acid sequence of the C-terminal domain is at least 98% identical to amino acids 50-621 of SEQ ID NO:5, and wherein the amino acid sequence of the Rht-B1 polypeptide differs from the sequence set forth as SEQ ID NO:5 by at least (i) an insertion of one or more amino acids between amino acids 49 and 50 of SEQ ID NO:5, and (ii) one or more amino acid substitutions in the C-terminal domain relative to amino acids 50-621 of SEQ ID NO:5. The Rht-B1 polypeptide of the invention may be further defined as described in the paragraphs above with respect to the wheat plant.

The present invention also provides a method of genotyping a wheat plant, the method comprising (i) obtaining a sample comprising nucleic acid or protein extracted from a wheat plant, and (ii) detecting in the sample a nucleic acid molecule or polypeptide of the present invention. In preferred embodiments the wheat plant comprises an Rht-B1 allele selected from the group consisting of Rht-B1c.1, Rht-B1c.2, Rht-B1c.3, Rht-B1c.4, Rht-B1c.5, Rht-B1c.6, Rht-B1c.7, Rht-B1c.8, Rht-B1c.9, Rht-B1c.10, Rht-B1c.12, Rht-B1c.15, Rht-B1c.16, Rht-B1c.17, Rht-B1c.18, Rht-B1c.21, Rht-B1c.22, Rht-B1c.23, Rht-B1c.24, Rht-B1c.26, Rht-B1c.27, Rht-B1c.28, Rht-B1c.29, Rht-B1c.30, and Rht-B1c.32.

The present invention also provides a method of introducing an Rht-B1 allele into a wheat plant lacking said allele, the method comprising i) crossing a first parent wheat plant with a second parent wheat plant, wherein the second plant is a wheat plant of the present invention, and ii) backcrossing a progeny plant of the cross of step i) with a plant of the same genotype as the first parent plant to produce a plant with a majority of the genotype of the first parent but comprising said Rht-B1 allele.

The nucleic acid molecule of the present invention may be operably linked to a promoter capable of directing expression of the nucleic acid molecule in a plant cell. Also provided is a vector comprising or encoding the nucleic acid molecule of the present invention and host cells comprising this vector and/or the nucleic acid molecule of the present invention The present invention also provides a genetically modified plant where the plant has been transformed with the nucleic acid molecule of the present invention and progeny plants thereof comprising the nucleic acid molecule. In certain embodiments the genetically modified plant is a wheat or barley plant.

Cereals as used herein means plants or grain of the monocotyledonous families Poaceae or Graminae which are cultivated for the edible components of their seeds, and includes wheat, barley, maize, oats, rye, rice, sorghum, triticale, millet, buckwheat. Preferably, the cereal plant or grain is wheat or barley plant or grain, more preferably wheat plant or grain. In a further preferred embodiment, the cereal plant is not rice or maize or either of these.

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

The wheat plants of the invention may have many uses other than uses for food or animal feed, for example uses in research or breeding. In seed propagated crops such as wheat, the plants can be self-crossed to produce a plant which is homozygous for the desired genes, or haploid tissues such as developing germ cells can be induced to double the chromosome complement to produce a homozygous plant.

The wheat plants of the invention may be crossed with plants containing a more desirable genetic background. The desired genetic background may include a suitable combination of genes providing commercial yield and other characteristics such as agronomic performance or abiotic stress resistance. The genetic background might also include other altered starch biosynthesis or modification genes, for example genes from other wheat lines. The genetic background may comprise one or more transgenes such as, for example, a gene that confers tolerance to a herbicide such as glyphosate.

As used herein, the term "linked" refers to a marker locus and a second locus being sufficiently close on a chromosome that they will be inherited together in more than 50% of meioses, e.g., not randomly. This definition includes the situation where the marker locus and second locus form part of the same gene. Furthermore, this definition includes the situation where the marker locus comprises a polymorphism that is responsible for the trait of interest (in other words the marker locus is directly "linked" to the phenotype). The term "genetically linked" as used herein is narrower, only used in relation to where a marker locus and a second locus being sufficiently close on a chromosome that they will be inherited together in more than 50% of meioses. Thus, the percent of recombination observed between the loci per generation (centimorgans (cM)), will be less than 50. In particular embodiments of the invention, genetically linked loci may be 45, 35, 25, 15, 10, 5, 4, 3, 2, or 1 or less cM apart on a chromosome. Preferably, the markers are less than 5 cM or 2 cM apart and most preferably about 0 cM apart.

As used herein, the "other genetic markers" may be any molecules which are linked to a desired trait of a cereal plant such as wheat. Such markers are well known to those skilled in the art and include molecular markers linked to genes determining traits such disease resistance, yield, plant morphology, grain quality, other dormancy traits such as grain colour, gibberellic acid content in the seed, plant height, flour colour and the like. Examples of such genes are stem-rust resistance genes Sr2 or Sr 38, the stripe rust resistance genes YrIO or Yr 17, the nematode resistance genes such as Cre1 and Cre3, alleles at glutenin loci that determine dough strength such as Ax, Bx, Dx, Ay, By and Dy alleles. With specific regard to grain dormancy, other markers include the R gene for red grain colour (Himi et al., 2002), as well as markers described by Mares et al. (2005), Li et al. (2004), Kato et al. (2001), Mori et al. (2005) and Prada et al. (2004).

The term "plant" as used herein as a noun refers to whole plants, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plants provided by or contemplated for use in the practice of the present invention include both monocotyledons and dicotyledons. In preferred embodiments, the plants of the present invention are crop plants (for example, cereals and pulses, maize, wheat, potatoes, tapioca, rice, sorghum, soybean millet, cassava, barley, or pea), or legumes. The plants may be grown for production of edible roots, tubers, leaves, stems, flowers or fruit.

The terms "seed" and "grain" as used herein have overlapping meanings. "Grain" includes seed which has been harvested from a plant and generally refers to mature, harvested grain but can also refer to grain after imbibition or germination, according to the context. "Seed" can refer to either mature grain, either before or after harvesting, or to immature seeds which are developing in planta. Mature grain commonly has a moisture content of, less than about 10-15%.

As used herein, the term "gene" is to be taken in its broadest context and includes the deoxyribonucleotide sequences comprising the protein coding region of a structural gene and including sequences located adjacent to the coding region on both the 5' and 3' ends for a distance of at least about 2 kb on either end. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

An allele is a variant of a gene at a single genetic locus. Hexaploid wheat such as *Triticum aestivum* L. has six sets of chromosomes with a genome organization of AABBDD. Each chromosome has one copy of each gene (one allele). If both alleles of a chromosome pair are the same, the organism is homozygous with respect to that gene, if the alleles are different, the organism is heterozygous with respect to that gene. The interaction between alleles at a locus is generally described as dominant or recessive.

The wheat plants of the invention can be produced and identified after mutagenesis. This may provide a wheat plant which is non-transgenic, which is desirable in some markets, or which is free of exogenous nucleic acid molecule. Generally, a progenitor plant cell, tissue, seed or plant may be subjected to mutagenesis to produce single or multiple mutations, such as nucleotide substitutions, deletions, additions and/or codon modification.

Mutagenesis can be achieved by chemical or radiation means, for example EMS or sodium azide (Zwar and Chandler, 1995) treatment of seed, or gamma irradiation, well know in the art. Chemical mutagenesis tends to favour nucleotide substitutions rather than deletions. Heavy ion beam (HIB) irradiation is known as an effective technique for mutation breeding to produce new plant cultivars, see for example Hayashi et al., 2007 and Kazama et al, 2008. Ion beam irradiation has two physical factors, the dose (gy) and LET (linear energy transfer, keV/um) for biological effects that determine the amount of DNA damage and the size of DNA deletion, and these can be adjusted according to the desired extent of mutagenesis.

Biological agents useful in producing site-specific mutants include enzymes that include double stranded breaks in DNA that stimulate endogenous repair mechanisms. These include endonucleases, zinc finger nucleases, TAL effectors, transposases and site-specific recombinases. Zinc finger nucleases (ZFNs), for example, facilitate site-specific cleavage within a genome allowing endogenous or other end-joining repair mechanisms to introduce deletions or insertions to repair the gap. Zinc finger nuclease technology is reviewed in Le Provost et al., 2009, See also Dural et al., 2005 and Liu et al., 2010.

Isolation of mutants may be achieved by screening mutagenised plants or seed. For example, a mutagenized population of wheat may be screened directly for the desired genotype or indirectly by screening for a phenotype such as plant height. Screening directly for the genotype preferably includes assaying for the presence of mutations which may be observed in PCR assays by the absence of markers as expected when some of the genes are deleted, or heteroduplex based assays as in Tilling, or by deep sequencing. Screening for the phenotype may comprise screening for out growth as described in the Examples. Using this methodology large populations of mutagenised seeds may be screened for increased growth providing increased plant height.

Identified mutations may then be introduced into desirable genetic backgrounds by crossing the mutant with a plant of the desired genetic background and performing a suitable number of backcrosses to cross out the originally undesired parent background.

In the context of this application, an "induced mutation" or "introduced mutation" is an artificially induced genetic variation which may be the result of chemical or radiation treatment of a progenitor seed or plant. Nucleotide insertional derivatives include 5' and 3' terminal fusions as well as intra-sequence insertions of single or multiple nucleotides. Insertional nucleotide sequence variants are those in which one or more nucleotides are introduced into a site in the nucleotide sequence, either at a predetermined site as is possible with zinc finger nucleases (ZFN), TAL effectors or homologous recombination methods, or by random insertion with suitable screening of the resulting product. Deletional variants are characterised by the removal of one or more nucleotides from the sequence. Preferably, a mutant gene has only a single insertion of a sequence of nucleotides relative to the wild-type gene and one or more substitution mutations. Substitutional nucleotide variants are those in which at least one nucleotide in the sequence has been removed and a different nucleotide inserted in its place. The preferred number of nucleotides affected by substitutions in a mutant gene relative to the wild-type gene is a maximum of ten nucleotides, more preferably a maximum of 9, 8, 7, 6, 5, 4, 3, or 2, or most preferably only one nucleotide.

The term "mutation" as used herein does not include silent nucleotide substitutions which do not affect the activity of the gene, and therefore includes only alterations in the gene sequence which affect the gene activity. The term "polymorphism" refers to any change in the nucleotide sequence including such silent nucleotide substitutions. Screening methods may first involve screening for polymorphisms and secondly for mutations within a group of polymorphic variants.

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants. To further speed up the backcrossing program, the embryo from immature seeds (25 days post anthesis) may be excised and grown up on nutrient media under sterile conditions, rather than allowing full seed maturity.

Any molecular biological technique known in the art which is capable of detecting alleles of Rht-B1 can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, 2000; Langridge et al., 2001).

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (Ed. M J. McPherson and S. G Moller (2000) BIOS Scientific Publishers Ltd, Oxford).

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

The terms "transgenic plant" and "transgenic wheat plant" as used herein refer to a plant that contains a gene construct ("transgene") not found in a wild-type plant of the same species, variety or cultivar. That is, transgenic plants (transformed plants) contain genetic material that they did not contain prior to the transformation. A "transgene" as referred to herein has the normal meaning in the art of biotechnology and refers to a genetic sequence which has been produced or altered by recombinant DNA or RNA technology and which has been introduced into a progenitor plant cell, which cell is used to produce a new plant. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is typically stably integrated into the genome of the plant. The introduced genetic material may comprise sequences that naturally occur in the same species but in a rearranged order or in a different arrangement of elements, for example an antisense sequence or a sequence encoding a double-stranded RNA or an artificial microRNA precursor. Plants containing such sequences are included herein in "transgenic plants". Transgenic plants as defined herein include all progeny of an initial transformed and regenerated plant (TO plant) which has been genetically modified using recombinant techniques, where the progeny comprise the transgene. Such progeny may be obtained by self-fertilisation of the primary transgenic plant or by crossing such plants with another plant of the same species. In an embodiment, the transgenic plants are homozygous for each and every gene that has been introduced (transgene) so that their progeny do not segregate for the desired phenotype. Transgenic plant parts include all parts and cells of said plants which comprise the transgene such as, for example, seeds, cultured tissues, callus and protoplasts. A "non-transgenic plant", preferably a non-transgenic wheat plant, is one which has not been genetically modified by the introduction of genetic material by recombinant DNA techniques.

As used herein, the term "corresponding non-transgenic plant" refers to a plant which is the same or similar in most characteristics, preferably isogenic or near-isogenic relative to the transgenic plant, but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild-type", as used herein, refers to a cell, tissue or plant that has not been modified according to the invention. Wild-type cells, tissue or plants known in the art and may be used as controls to compare levels of expression of an exogenous nucleic acid or the extent and nature of trait modification with cells, tissue or plants modified as described herein. As used herein, "wild-type wheat grain" means a corresponding non-mutagenized, non-transgenic wheat grain. Specific wild-type wheat grains as used herein include but are not limited to Sunstate.

Any of several methods may be employed to determine the presence of a transgene in a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers that will distinguish the transformed and non-transformed plants. An alternative method to confirm a positive transformant is by Southern blot hybridization, well known in the art. Wheat plants which are transformed may also be identified i.e. distinguished from non-transformed or wild-type wheat plants by their phenotype, for example conferred by the presence of a selectable marker gene, or by immunoassays that detect or quantify the expression of an enzyme encoded by the transgene, or any other phenotype conferred by the transgene.

The wheat plants of the present invention may be grown or harvested for grain, primarily for use as food for human consumption or as animal feed, or for fermentation or industrial feedstock production such as ethanol production, among other uses. Alternatively, the wheat plants may be used directly as feed. The plant of the present invention is preferably useful for food production and in particular for commercial food production. Such food production might include the making of flour, dough, semolina or other products from the grain that might be an ingredient in commercial food production. The invention also provides flour, meal or other products produced from the grain. These may be unprocessed or processed, for example by fractionation or bleaching.

The terms "polypeptide" and "protein" are generally used interchangeably herein. The terms "proteins" and "polypeptides" as used herein also include variants, mutants, modifications and/or derivatives of the polypeptides of the invention as described herein. As used herein, "substantially purified polypeptide" refers to a polypeptide that has been separated from the lipids, nucleic acids, other peptides and other molecules with which it is associated in its native state. Preferably, the substantially purified polypeptide is at least 60% free, more preferably at least 75% free, and more preferably at least 90% free from other components with which it is naturally associated. By "recombinant polypeptide" is meant a polypeptide made using recombinant techniques, i.e., through the expression of a recombinant polynucleotide in a cell, preferably a plant cell and more preferably a wheat cell.

The % identity of a polypeptide relative to another polypeptide can be determined by GAP (Needleman and Wunsch, 1970) analysis (GCG program) with a gap creation penalty=5, and a gap extension penalty=0.3. The query sequence is at least 250 amino acids in length and the GAP analysis aligns the two sequences over a region of at least 250 amino acids. Most preferably, two polypeptides in question are aligned over their full length amino acid sequences.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence deletions generally range from about 1 to 15 residues, more preferably about 1 to 10 residues and typically about 1 to 5 contiguous residues. Substitution mutants have at least one amino acid residue in the polypeptide molecule removed and a different residue inserted in its place.

By "isolated" is meant material that is substantially or essentially free from components that normally accompany it in its native state. As used herein, an "isolated polynucleotide" or "isolated nucleic acid molecule" means a polynucleotide which is at least partially separated from, preferably substantially or essentially free of, the polynucleotide sequences of the same type with which it is associated or linked in its native state. For example, an "isolated polynucleotide" includes a polynucleotide which has been purified or separated from the sequences which flank it in a naturally occurring state, e.g., a DNA fragment which has been removed from the sequences which are normally adjacent to the fragment. Preferably, the isolated polynucleotide is also at least 90% free from other components such as proteins, carbohydrates, lipids etc. The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably connected to the nucleotide sequence to be transcribed in the cell.

The present invention refers to use of oligonucleotides which may be used as "probes" or "primers". As used herein, "oligonucleotides" are polynucleotides up to 50 nucleotides in length. They can be RNA, DNA, or combinations or derivatives of either. Oligonucleotides are typically relatively short single stranded molecules of 10 to 30 nucleotides, commonly 15-25 nucleotides in length, typically comprised of 10-30 or 15-25 nucleotides which are identical to, or complementary to, the sequence of interest. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length. Polynucleotides used as a probe are typically conjugated with a detectable label such as a radioisotope, an enzyme, biotin, a fluorescent molecule or a chemiluminescent molecule.

The terms "polynucleotide variant" and "variant" and the like refer to polynucleotides displaying substantial sequence identity with a reference polynucleotide sequence and which are able to function in an analogous manner to, or with the same activity as, the reference sequence. These terms also encompass polynucleotides that are distinguished from a reference polynucleotide by the addition, deletion or substitution of at least one nucleotide, or that have, when compared to naturally occurring molecules, one or more mutations. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Accordingly, these terms encompass polynucleotides that encode polypeptides that exhibit enzymatic or other regulatory activity, or polynucleotides capable of serving as selective probes or other hybridising agents. The terms "polynucleotide variant" and "variant" also include naturally occurring allelic variants. Mutants can be either naturally occurring (that is to say, isolated from a natural source) or synthetic (for example, by performing site-directed mutagenesis on the nucleic acid). Preferably, a polynucleotide variant of the invention which encodes a polypeptide with enzyme activity is greater than 400, more preferably greater than 500, more preferably greater than 600, more preferably greater than 700, more preferably greater than 800, more preferably greater than 900, and even more preferably greater than 1,000 nucleotides in length, up to the full length of the gene.

A variant of an oligonucleotide of the invention includes molecules of varying sizes which are capable of hybridising, for example, to the wheat genome at a position close to that of the specific oligonucleotide molecules defined herein. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise to the target region. In addition, variants may readily be designed which hybridise close (for example, but not limited to, within 50 nucleotides) to the region of the plant genome where the specific oligonucleotides defined herein hybridise.

By "corresponds to" or "corresponding to" in the context of polynucleotides or polypeptides is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein. Terms used to describe sequence relationships between two or more polynucleotides or polypeptides include "reference sequence", "comparison window", "sequence identity", "percentage of sequence identity", "substantial identity" and "identical", and are defined with respect to a defined minimum number of nucleotides or amino acid residues or preferably over the full length. The terms "sequence identity" and "identity" are used interchangeably herein to refer to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, U) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The % identity of a polynucleotide can be determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides, or at least 400, 500 or 600 nucleotides in each case. Reference also may be made to the BLAST family of programs as for example disclosed by Altschul et al., 1997. A detailed discussion of sequence analysis can be found in Unit 19.3 of Ausubel et al., 1994-1998, Chapter 15.

Nucleotide or amino acid sequences are indicated as "essentially similar" when such sequences have a sequence identity of at least about 98%, more particularly at least about 98.5%, quite particularly about 99%, especially about 99.5%, more especially about 100%, quite especially are identical. It is clear that when RNA sequences are described as essentially similar to, or have a certain degree of sequence identity with, DNA sequences, thymine (T) in the DNA sequence is considered equal to uracil (U) in the RNA sequence.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In some embodiments, the present invention refers to the stringency of hybridization conditions to define the extent of complementarity of two polynucleotides. "Stringency" as used herein, refers to the temperature and ionic strength conditions, and presence or absence of certain organic solvents, during hybridization. The higher the stringency, the higher will be the degree of complementarity between a target nucleotide sequence and the labelled polynucleotide sequence. "Stringent conditions" refers to temperature and ionic conditions under which only nucleotide sequences having a high frequency of complementary bases will hybridize. As used herein, the term "hybridizes under low stringency, medium stringency, high stringency, or very high stringency conditions" describes conditions for hybridization and washing. Guidance for performing hybridization reactions can be found in Current Protocols in Molecular Biology, John Wiley & Sons, N.Y. (1989), 6.3.1-6.3.6, herein incorporated by reference. Specific hybridization conditions referred to herein are as follows: 1) low stringency hybridization conditions in 6× sodium chloride/sodium citrate (SSC) at about 45° C., followed by two washes in 0.2×SSC, 0.1% SDS at 50-55° C.; 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and 4) very high stringency hybridization conditions are 0.5 M sodium phosphate, 7% SDS at 65° C., followed by one or more washes at 0.2×SSC, 1% SDS at 65° C.

As used herein, a "chimeric gene" or "genetic construct" refers to any gene that is not a native gene in its native location i.e. it has been artificially manipulated, including a chimeric gene or genetic construct which is integrated into the wheat genome. Typically a chimeric gene or genetic construct comprises regulatory and transcribed or protein coding sequences that are not found together in nature. Accordingly, a chimeric gene or genetic construct may comprise regulatory sequences and coding sequences that are derived from different sources, or regulatory sequences and coding sequences derived from the same source, but arranged in a manner different than that found in nature. The term "endogenous" is used herein to refer to a substance that is normally produced in an unmodified plant at the same developmental stage as the plant under investigation, preferably a wheat plant. An "endogenous gene" refers to a native gene in its natural location in the genome of an organism preferably in a wheat plant. As used herein, "recombinant nucleic acid molecule" refers to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations, preferably the wheat genome, but which does not naturally occur in the cell. These include modified forms of gene sequences found in that cell so long as the introduced gene contains some modification, e.g. an introduced mutation or the presence of a selectable marker gene, relative to the naturally-occurring gene. Foreign or exogenous genes may be genes found in nature that are inserted into a non-native organism, native genes introduced into a new location within the native host, or chimeric genes or genetic constructs. A "transgene" is a gene that has been introduced into the genome by a transformation procedure. The term "genetically modified" includes introducing genes into cells, mutating genes in cells and altering or modulating the regulation of a gene in a cell or organisms to which these acts have been done or their progeny.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide, which is approximately the same as the distance between that promoter and the gene it controls in its natural setting; i.e., the gene from which the promoter is derived. As is known in the art, some variation in this distance can be accommodated without loss of function.

With regard to cereal plants, as used herein the term "germination" refers to the emergence of the coleorhiza from the seed coat after imbibition.

The "rate of germination" of a seed refers to the percentage of seeds in a population which have germinated over a period of time, for example up to 21 days, or in the period 1 to 10 days, after the beginning of imbibition. A population of seeds can be assessed daily over several days to determine the germination percentage over time. Certain aspects of the invention relate to altering/modulating the rate of germination of a seed. This alteration/modulation may be transient during the life span of a seed. For example following harvest a seed of transgenic plant of the invention may have an altered rate of germination when compared to a seed of a corresponding non-transgenic plant upon harvest, however, following six months storage in a silo the seed of the same transgenic plant of the invention may have the same rate of germination when compared to a seed of a corresponding non-transgenic plant following six months storage in a silo, or vice versa. In other words, at some point in the life span of the seed it will have an altered rate of germination when compared to a suitable control (non-transgenic or wild type etc.) which has been exposed to the same conditions.

As used herein, the term "dormant" refers to the failure of the viable, intact seeds of a plant to germinate under specified favourable conditions, particularly in terms of temperature and in the presence of moisture. Dormancy is a quantitative trait. With regard to barley and wheat, seeds of a plant are considered dormant if less than 90% of viable, intact seeds germinate after 7 days at 20° C. following the beginning of imbibition. Viable seeds are those which are able to germinate after dormancy breaking, for example a substantial period (weeks or months) of storage at room temperature or heat treatment, well known in the art.

As used herein, the term "non-dormant" refers to the ability of the seeds of a plant to germinate under specified favourable conditions. With regard to barley and wheat, seeds of a plant are considered non-dormant if at least 90% of the viable, intact seeds germinate after 7 days at 20° C. following the beginning of imbibition.

As used herein, the term "nucleic acid amplification" refers to any in vitro method for increasing the number of copies of a nucleic acid molecule with the use of a DNA polymerase. Nucleic acid amplification results in the incorporation of nucleotides into a DNA molecule or primer thereby forming a new DNA molecule complementary to a DNA template. The newly formed DNA molecule can be used a template to synthesize additional DNA molecules.

The present invention includes the production of various transgenic plants. These include, but are not limited to, plants that have one or more of the desirable traits exhibited by the wheat plants of the present invention.

Nucleic acid constructs useful for producing the above-mentioned transgenic plants can readily be produced using standard techniques. To ensure appropriate expression of the gene encoding an mRNA of interest, the nucleic acid construct typically comprises one or more regulatory elements such as promoters, enhancers, as well as transcription termination or polyadenylation sequences. Such elements are well known in the art. The transcriptional initiation region comprising the regulatory element(s) may provide for regulated or constitutive expression in the plant. The regulatory elements may be selected from, for example, seed-specific promoters, or promoters not specific for seed cells (such as ubiquitin promoter or CaMV35S or enhanced 35S promoters). Examples of seed specific promoters useful for the present invention include, but are not limited to, the wheat low molecular weight glutenin promoter (Colot et al., 1987), the promoter expressing α-amylase in wheat seeds (Stefanov et al., 1991), and the hordein promoter (Brandt et al., 1985). The promoter may be modulated by factors such as temperature, light or stress. Ordinarily, the regulatory elements will be provided 5' of the genetic sequence to be expressed. The construct may also contain other elements that enhance transcription such as the nos 3' or the ocs 3' polyadenylation regions or transcription terminators.

Typically, the nucleic acid construct comprises a selectable marker. Selectable markers aid in the identification and screening of plants or cells that have been transformed with the exogenous nucleic acid molecule. The selectable marker gene may provide antibiotic or herbicide resistance to the wheat cells, or allow the utilization of substrates such as mannose. The selectable marker preferably confers hygromycin resistance to the wheat cells.

Preferably, the nucleic acid construct is stably incorporated into the genome of the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes a recombinant vector, which includes at least one polynucleotide molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred host cells are plant cells, more preferably cells of a cereal plant, more preferably barley or wheat cells, and even more preferably a wheat cell.

Preferably, the transgenic plant is a cereal plant. Examples of cereal plants include, but are not limited to, wheat, barley, sorghum oats, and rye. More preferably, the cereal plant is wheat or barley. In a further preferred embodiment, the cereal plant is not rice.

Transgenic plants, as defined in the context of the present invention include plants and their progeny which have been genetically modified using recombinant techniques. This would generally be to modulate the production of at least one polypeptide defined herein in the desired plant or plant organ. Transgenic plant parts include all parts and cells of said plants such as, for example, cultured tissues, callus and protoplasts. Transformed plants contain genetic material that they did not contain prior to the transformation. The genetic material is preferably stably integrated into the genome of the plant. The introduced genetic material may comprise sequences that naturally occur in the same species but in a rearranged order or in a different arrangement of elements, for example an antisense sequence. Such plants are included herein as "transgenic plants". A "non-transgenic plant" is one which has not been genetically modified with the introduction of genetic material by recombinant DNA techniques. In a preferred embodiment, the transgenic plants are homozygous for each and every gene that has been introduced (transgene) so that their progeny do not segregate for the desired phenotype.

Several techniques exist for introducing foreign genetic material into a plant cell. Such techniques include acceleration of genetic material coated onto microparticles directly into cells (see, for example, U.S. Pat. Nos. 4,945,050 and 5,141,131). Plants may be transformed using *Agrobacterium* technology (see, for example, U.S. Pat. Nos. 5,177,010, 5,104,310, 5,004,863, 5,159,135). Electroporation technology has also been used to transform plants (see, for example, WO 87/06614, U.S. Pat. Nos. 5,472,869, 5,384,253, WO 92/09696 and WO 93/21335). In addition to numerous technologies for transforming plants, the type of tissue which is contacted with the foreign genes may vary as well. Such tissue would include but would not be limited to embryogenic tissue, callus tissue type I and II, hypocotyl, meristem, and the like. Almost all plant tissues may be transformed during development and/or differentiation using appropriate techniques described herein.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors can also contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Any of several methods may be employed to determine the presence of a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers that will distinguish the transformed and non-transformed plants. For example, primers may be designed that will amplify a region of DNA from the transformation vector reading into the construct and the reverse primer designed from the gene of interest. These primers will only amplify a fragment if the plant has been successfully transformed. An alternative method to confirm a positive transformant is by Southern blot hybridization, well known in the art. Plants which are transformed may also be identified i.e. distinguished from non-transformed or wild-type plants by their phenotype, for example conferred by the presence of a selectable marker gene, or conferred by the phenotype of a desired seed dormancy.

Methods for transformation of cereal plants such as wheat and barley for introducing genetic variation into the plant by introduction of an exogenous nucleic acid and for regeneration of plants from protoplasts or immature plant embryos are well known in the art, see for example, Wan and Lemaux (1994), Tingay et al., (1997), Canadian Patent Application No. 2,092,588, Australian Patent Application No 61781/94, Australian Patent No 667939, U.S. Pat. No. 6,100,447, International Patent Application PCT/US97/10621, U.S. Pat. Nos. 5,589,617, 6,541,257, and other methods are set out in Patent specification WO99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts.

The regenerable wheat cells are preferably from the scutellum of immature embryos, mature embryos, callus derived from these, or the meristematic tissue.

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants. To further speed up the backcrossing program, the embryo from immature seeds (25 days post anthesis) may be excised and grown up on nutrient media under sterile conditions, rather than allowing full seed maturity.

Any molecular biological technique known in the art which is capable of detecting Rht-B1 alleles can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, 2000; Langridge et al., 2001). The invention also includes the use of molecular marker techniques to detect polymorphisms linked to Rht-B1 alleles. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al., (2001).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

As used in the subject specification, the singular forms "a", "an" and "the" include plural aspects unless the context clearly dictates otherwise. Thus, for example, reference to "a" includes a single as well as two or more; reference to "an" includes a single as well as two or more; reference to "the" includes a single as well as two or more and so forth.

Having generally described the invention, the same will be more readily understood by reference to the following examples, which are provided by way of illustration and are not intended as limiting.

EXAMPLES

Example 1. Materials and Methods

Plant Material

Grains of the tall wheat variety Maringá (Rht-B1a) and a near-isogenic dwarf line (Rht-B1c) in the Maringa genetic background were obtained from the Australian Winter Cereals Collection, Tamworth, NSW, Australia. Maringá is a Brazilian breadwheat variety. The near-isogenic dwarf line was produced by seven backcrosses (BC7) with recurrent selection of the dwarf allele (Rht-B1c) into Maringá (Hoogendoorn et al. 1988).

Himalaya barley and three previously characterised dwarf mutant derivatives are described in Table 1. Plants were grown either in a greenhouse in 20 cm pots containing a compost-based mix under natural light with daylength extension to 14 hours provided during winter months, or in the field at Black Mountain or at Ginninderra Experimental Station, both located in Canberra, Australia.

Mutagenesis

The method for mutagenesis of barley and wheat grains was a simplification of a procedure used previously (Zwar and Chandler, 1995). 1-2 kg of grain of each line was imbibed in twice its mass of water at 4° C. overnight. They were transferred to 2-litre measuring cylinders filled with water, and aerated with pressurised air for 8 h, with one change of fresh water given after 4 h. Grains were then incubated for 2 h in freshly-prepared 1 mM Na azide dissolved in 0.1 M K phosphate buffer pH 3.0, and then washed extensively in running water for 2 h, placed in a fume hood to dry overnight, and sown in the field within several days of treatment.

Construction of Derivative Lines Carrying Overgrowth Alleles

The barley overgrowth alleles were back-crossed, inter-crossed and out-crossed to generate a set of lines suitable for detailed physiological characterisation. Four of the new Sln1 overgrowth alleles occurred in either grd2b or gse1n dwarfing backgrounds and were back-crossed two generations to the WT allowing overgrowth phenotypes to be compared in tall and dwarf backgrounds. The loss of the original dwarfing allele was confirmed by PCR. The remaining seven new Sln1 overgrowth alleles occurred in the Sln1d dwarf background, and four of these (Sln1d.7, Sln1d.8, Sln1d.9 and TR103) have been through two generations of back-crossing to the WT.

α-Amylase Production by Endosperm Half-Grains

Endosperm half-grains were prepared and incubated with or without $GA_3$ (1 µM) at 22° C. for 0, 42 or 72 h. To each sample, 1.5 mL of a solution of 10 mm $CaCl_2$ was added, the half-grains were homogenised, and an aliquot of 1 mL was clarified by centrifugation (20,000 g for 5 min). The supernatant was analyzed for α-amylase activity using the Megazyme alpha-amylase (Ceralpha) procedure.

Assessment of Grain Dormancy

Plants were grown as single rows in the field, and heads were inspected twice per week to monitor drying. When all green colour had been lost from the heads, they were judged to be physiologically mature and were excised and taken to the lab. Heads were placed in a fume hood for 48 h to promote final drying, especially of basal grains that tended to remain moist, and were then threshed by hand. The grains were placed in a manila envelope and left in the lab environment for different periods of after-ripening. Germination was assessed by incubating 100 grains of each line on moist filter paper in a 20° C. environment with low intensity fluorescent lighting. The percentage germination of each grain sample was assessed after 7 days incubation Germination is defined in this context as emergence of the root radicle from the seed coat. In a first season's experiment, many grain samples, especially from tall wheat plants, showed low dormancy and there was considerable germination (at least 50% of grains germinated) after only 13-19 days after-ripening. These lines were generally not tested again. Other grain samples had low germination after 13-19 days after-ripening, and these were tested again after 32-33 days, and if germination was still low, again after 48-49 days after-ripening. Relative dormancy scores were given on a scale of 1 (least dormant) to 4 (highest dormancy).

Figure 9:
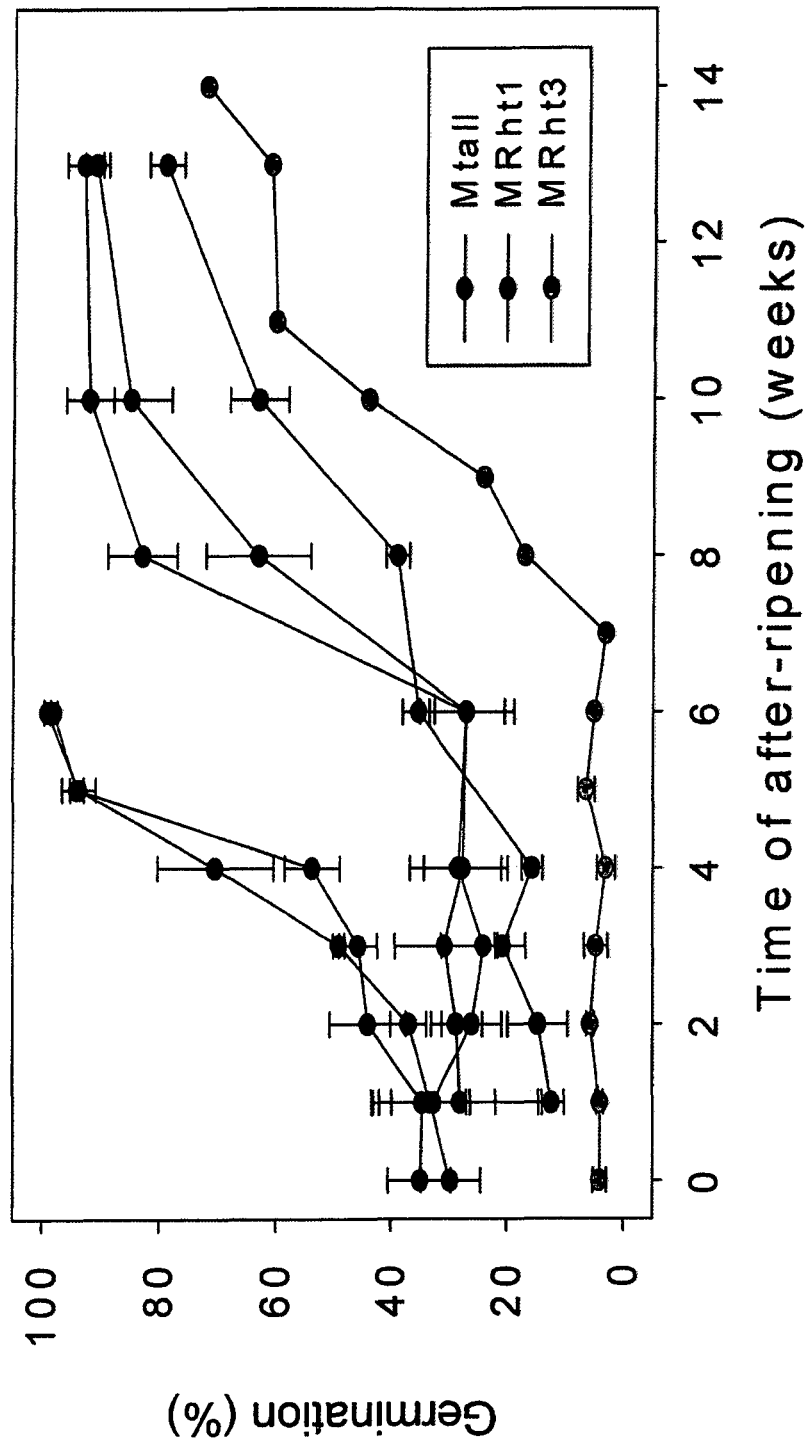

In a second season's experiment, dormancy assessments focused on semidwarf and control lines, and germination was determined weekly from harvest until either dormancy was lost, or up to 12 weeks after-ripening. An example of the results of a grain dormancy test is given in FIG. 9. One measure of the grain dormancy was determined as the number of weeks of storage of the grain (also termed "after-ripening") at room temperature in order for at least 50% of the grains in a grain population to germinate, as assessed by the method described in the previous paragraph.

Coleoptile Lengths of Barley and Wheat Overgrowth Lines

Coleoptile lengths were determined on wheat and barley seedlings after 21 days growth in the dark with a daily temperature program of 12 h at 12° C. and 12 h at 8° C., in the presence of fully adequate supplies of water.

Emergence from Deep Sowing Under Dry Conditions.

Grain samples were sown at a depth of 10 cm in soil (standard potting soil) in the greenhouse. The initial soil moisture content was 12-14% (w/w). Germination, early growth and seedling establishment, until emergence of the third leaf, occured without any additional watering to simulate dry sowing conditions in the field. The percentage of grains that yielded emerged seedlings and the timing of emergence were evaluated.

Leaf Elongation Rates and GA Dose-Response Curves

The methods have been previously described (Chandler and Robertson, 1999). Curves were fitted to data points using a 4-parameter Hill equation.

Root Length Measurements

Root growth is assessed under controlled conditions and in plants growing in the field. In the former case, root lengths are assessed by scanning, while in the field, 2 m cores are taken and root numbers assessed at 10 cm intervals along the cores.

PCR Amplification of DNA and Sequencing

DNA was prepared from barley or wheat leaves by the method of Ellis et al., 2005. Wheat sequences were amplified using primer pairs in which one primer was specific for the Rht-B1 gene (Table 2). The 3' half of the gene was amplified using conserved forward primers and reverse primers that were specific to B gene sequences in the 3' UT region. PCR amplification of barley sequences used primers specific for the Sln1, Spy1 and Gse1 genes. Amplified fragments were treated with Exosap-IT (Affymetrix) to remove primers, and then sequenced using Big Dye Terminator (Applied Biosystems).

DNA Sequences

The sequences of the Rht-A1a, Rht-B1a and Rht-D1b genes of wheat and the proteins encoded thereby are in accessions JF930277, JF930278 and JF930281 respectively. The amino acid sequences are aligned by ClustalW, showing the amino acids that differ (FIG. 7). The partial nucleotide sequence of the Rht3-B1c gene in the dwarf Maringa derivative is shown in SEQ ID NO. 1.

The sequence of the Rht-B1c protein encoded by the Rht-B1c allele is shown in SEQ ID NO. 3.

The sequence accessions for the Sln1 and Spy1 genes of barley are AK372064 and AF035820 respectively.

Example 2. Isolation of Wheat Mutants Comprising New Alleles of Rht-B1

Figure 2:
FIG. 2: Overgrowth mutants of wheat grown under controlled conditions, compared to parental (dwarf) and wild-type (tall) plants. From left to right, derivatives of Maringa carrying Rht-B1c (dwarf), Rht-B1a (tall), or three different overgrowth derivatives of Rht-B1c. The three overgrowth derivatives differ in their final height, and the arrows point to the heads of each line. Two of the derivatives are semi-dwarf, the third is a tall as the wild-type.

Grains of a wheat variety Maringá, which comprised an Rht-B1c allele that caused severe plant dwarfing, were treated with sodium azide as described in Example 1. The mutagenized grains were sown in the field and the resultant $M_1$ plants allowed to self-fertilise. $M_2$ grains were harvested from the $M_1$ plants upon maturity. $M_2$ seeds were sown in the field or at high density in flats (FIG. 1) in the greenhouse and screened for increased height either during early growth or when mature in the field. About 1.6 million $M_2$ plants were screened by these methods. FIG. 1 shows how readily mutants could be identified. Approximately 400 plants were selected which exhibited either early leaf elongation rates or mature plant height that ranged from slightly greater than the dwarf parent variety Maringa (Rht-B1c) to as tall as the near-isogenic, Rht-B1a (wild-type allele) plants. These were self-fertilised and progeny plants grown under controlled conditions and compared to the parental (Rht-B1c) and wild-type (Rht-B1a) plants (FIG. 2). These plants were termed "overgrowth mutants" because they grew at increased rates or to increased mature height relative to the parental variety.

The dwarfing mutation in the Rht-B1c allele was due to a 2026 bp insertion in the Rht-B1 gene in Maringa (Wu et al., 2011). PCR testing revealed that about half of the 400 selected mutant plants were positive for the presence of the insertion in this gene; such plants had retained an Rht-B1 gene. The remainder of the selected plants were negative for the PCR assay and appeared to lack the Rht-B1 gene entirely, although the homoeologous gene encoded by the D genome (Rht-D1) was still present based on positive PCR amplifications. Many in this latter group had distinct morphological alterations and poor spike fertility. It is likely that they represented deletions of the Rht-B1 gene along with varying amounts of flanking chromosomal DNA. These deletion lines were not studied further.

The Rht-B1 gene in each of 139 non-deletion mutants was sequenced by amplifying regions of the gene by PCR. Thirty-five new derivative alleles of Rht-B1c were identified, each one a variant of the Rht-B1c allele in Maringa. These were designated Rht-B1c.1, Rht-B1c.2, Rht-B1c.3 etc. They are listed in Table 3. Many of the 35 alleles were represented by multiple lines containing an identical specific mutation. In some cases, these multiple lines could be siblings, whereas in other cases they must have represented independent mutational events. There was a total of 62 independent events that generated the 35 alleles.

The mutants exhibited three different classes of mutation responsible for the overgrowth phenotype. In a first class, ten alleles comprised premature translation termination codons in the Rht-B1 gene. In most cases, the mutant codon was from a TGG codon (encoding Trp) to a TGA (stop codon). In barley, premature stop codons in DELLA result in an elongated slender phenotype and male sterility. In contrast, plants of these ten mutant wheat lines, with one exception, grew to a height that was the same or nearly the as of the tall (wild-type) isoline and showed a similar fertility to the wild-type. Presumably the expression of the A and/or D genome Rht-1 proteins in those mutants provided genetic compensation for the B genome null mutant genes and limited the phenotypic expression to 'tall' rather than 'slender'. The one exception, plants of the sole Rht-B1c.22 representative (line TR544) were semidwarf rather than 'tall'. This phenotype might have been due to altered splicing of the mutated Rht-B1c.22 gene in these plants that generated a Rht-B1 protein with a different in-frame insertion (discussed below).

The second class comprised amino acid substitutions in the Rht-B1 protein encoded by the B genome. Twenty examples are listed in Table 3. It was of interest to compare these 20 substitutions to the DELLA substitution mutants isolated in barley (Example 5), see FIG. 3. Across the two species, there were 31 single amino acid substitutions, including four sites where identical amino acid changes occurred. It was also noted that identical, though independent, mutations occurred within barley and within wheat, where the same mutation was found at corresponding positions in lines derived from different sub-populations of $M_2$ grains.

Figure 3:
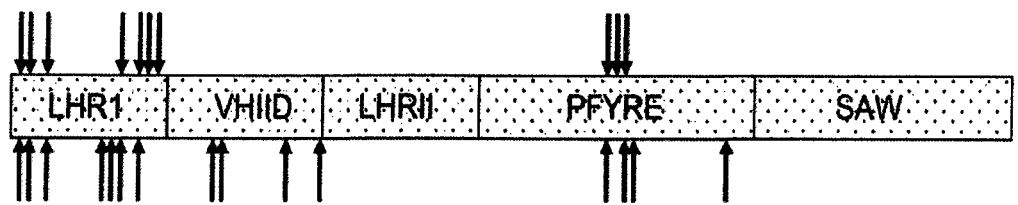
FIG. 3: Schematic of the sites of amino acid substitutions in overgrowth mutants of barley (upper arrows) and wheat (lower arrows) in the C-terminal GRAS domain of the DELLA polypeptides. Conserved amino acid regions are indicated.
Figure 4:
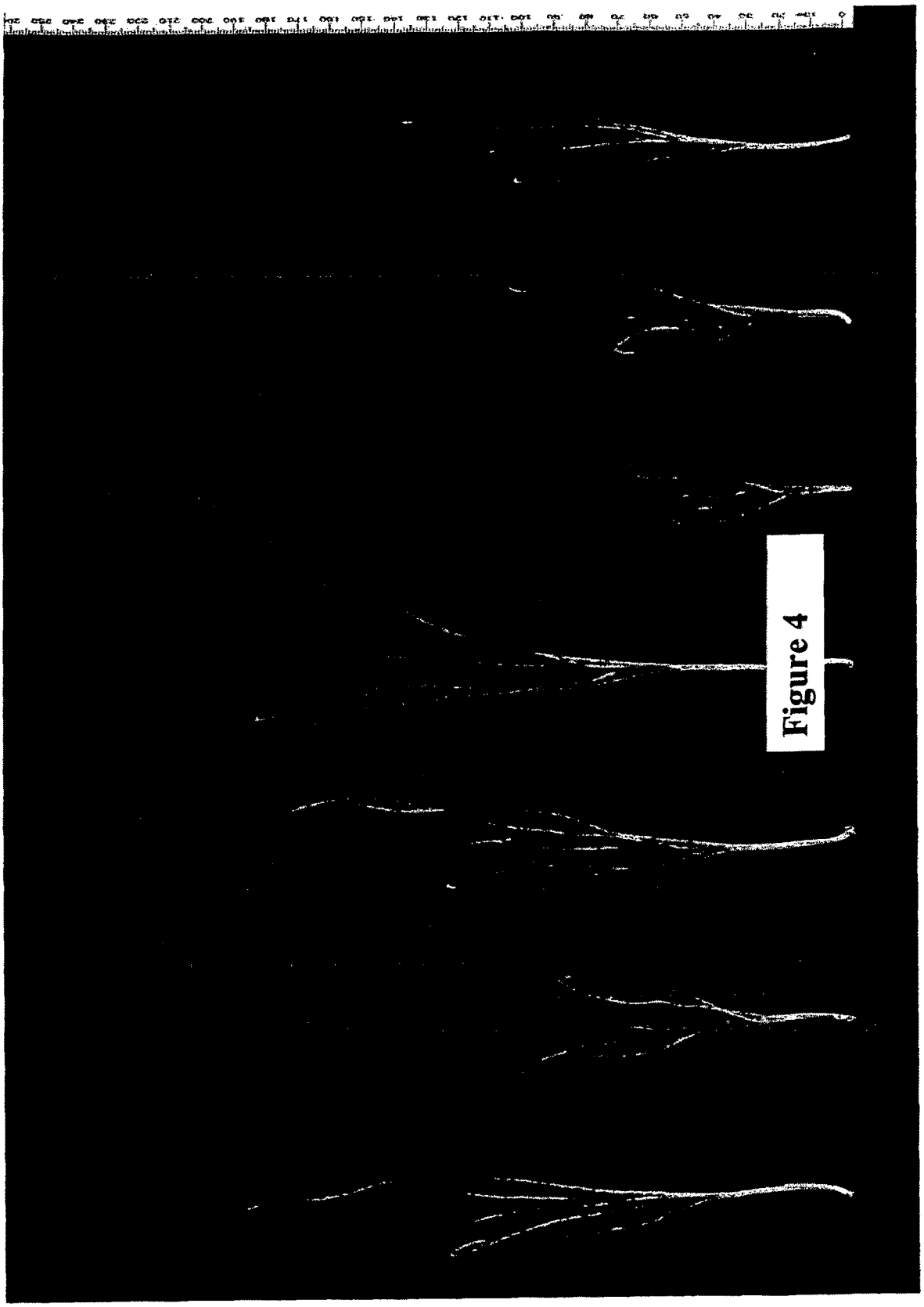
FIG. 4: Barley seedlings at the same age (left to right) Himalaya (WT), M463 (grd2b), TR261 (grd2b, sln1m), M240 (sln1m), M640 (Sln1d), TR107 (Sln1d.10), TR60 (Sln1d.8).
Figure 5:
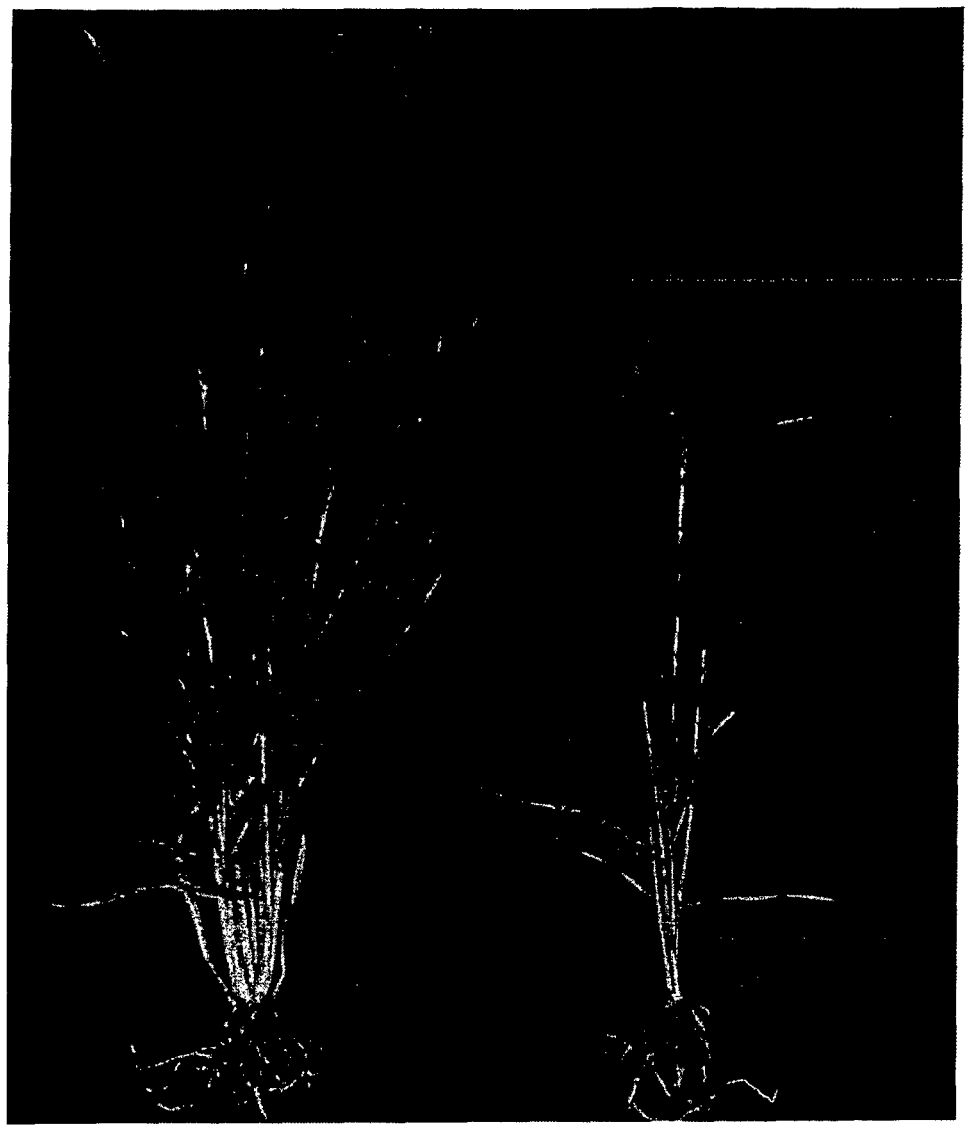
FIG. 5: Altered morphology in some wheat mutant lines. An example of normal (left) and abnormal (right) morphologies, with the latter featuring narrow leaves, thin stems, a poorly developed root system and, in some cases, heads with fewer than normal grains.
Figure 6:
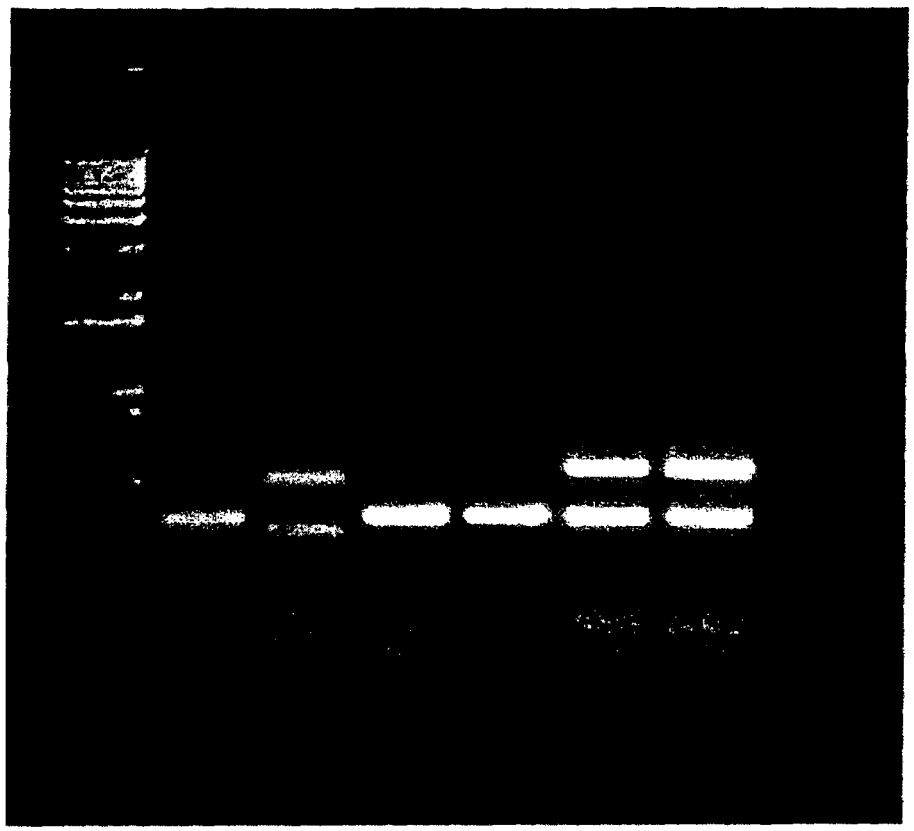
FIG. 6: Duplex PCR analysis of DNA from (1 to r): Maringá rht-1, Maringá Rht-B1c controls; two overgrowth lines with abnormal morphology; two overgrowth lines with normal morphology; no template control. Size markers on the left. The upper band represents amplification of a fragment of the Rht-B1c allele, and the lower band is a product of the Rht-D1 gene.

FIG. 3 schematically shows the sites of amino acid substitutions in the mutants relative to the position of conserved motifs in the in the C-terminal region of the barley and wheat proteins. The observation that the overgrowth mutations were distributed throughout much of the C-terminal region indicated that there was considerable potential for alterations in the binding of the DELLA proteins to interacting protein partners.

The third class of mutants included 5 alleles which each contained a mutation in regions of Rht-B1 predicted to be involved in excision of most of the insertion in the Rht-B1 gene which generated the Rht-B1c allele (Table 3). These alleles each affected one of the four nucleotides immediately adjacent to the splicing donor and acceptor sites. In some cases including for the Rht-B1c.22 allele, and depending on which splicing prediction software was used, there was the potential for these sequence alterations to alter the preferred site of splicing, thereby generating Rht-B1 proteins with slightly larger or smaller in-frame insertions. These splicing alleles presumably produced less of the Rht-B1 protein containing the 30 amino acid insertion and/or produced modified Rht-B1 proteins with altered in-frame insertions. Experimental evidence for alteration in the splicing efficiency was obtained by examining the RNA by RT-PCR methods.

Example 3. Phenotypic Testing of Wheat Mutants Comprising New Alleles of Rht-B1

The overgrowth mutants of wheat comprising new alleles of Rht-B1 were tested for a number of traits that were relevant for practical applications in the field for commercial production of wheat. The lengths of mature stems, the lengths of coleoptiles, and the relative grain dormancy for grain obtained from the mutant plants were measured and compared to control plants. The data are included in Table 4. The stem lengths of mature plants were assessed in different, irrigated field conditions (i.e. well watered) and in different seasons. In most cases, four independent data points were obtained and used to calculate the means shown in Table 4, which are expressed as a percentage relative to Rht-B1a plants. Different alleles led to different stem lengths, with some examples (e.g. Rht-B1c.6, c.8, c.21) being quite dwarfed, and others (Rht-B1c.11, c.25, c.31) as tall as the Rht-B1a isoline. In most cases, there was little variation between lines which carried the same allele. Based on the semi-dwarfing observed for plants of the Rht-B1b isoline which were approximately 81% the height of the wild-type (tall) plants, there were 15 new alleles that caused a similar extent of dwarfing, e.g. in the range 75-91% of the tall height.

Coleoptile lengths were also measured for the mutant plants, and calculated as a percentage of the average coleoptile length for Rht-B1a plants. The values of means from between 2 and 4 independent measurements are shown in Table 4. There was more variation for coleoptile lengths within a line than found for stem length. In part this may have related to differences between grains from field and greenhouse sources. Field-grown grains are available for the vast majority of lines in the next planting season, and further coleoptile measurements are carried out. It is expected these will show less variation. Overall there was a general positive correlation between stem lengths and coleoptile lengths. Further work is required to assess the statistical significance of differences in some cases where the correlation appears to break down.

Dormancy of grains of most of the mutant lines was assessed for grain harvested from two field seasons. In both seasons, the tall and Rht-B1b Maringa isolines showed low dormancy whereas the Rht-B1c isoline had relatively high dormancy. There were considerable differences in relative grain dormancy scores between different overgrowth lines. Data are presented in FIG. 9 for some of the lines, compared to the controls. Of particular interest were alleles that provided a suitable semidwarf plant height and which retained considerable grain dormancy such as Rht-B1c.9, c.17, c.22, c.23, c.24, c.26, c.27). These included the four semidwarfing lines currently being back-crossed into elite varieties.

Many of the lines were tested in a third season in the field. The data for plant height and dormancy score are shown in Table 8. The results were consistent in trend with the previous two seasons, showing that grain of some mutant lines required considerably longer in storage ("after-ripening") for 50% of the grains to germinate in the standard germination test (Example 1). Although the trend in dormancy between the lines and the controls was the same from season to season, the absolute numbers for any one line varied from season to season.

Example 4. Isolation of Overgrowth Mutants in Barley

To isolate overgrowth mutants in barley, three dwarf mutants of 'Himalaya' barley were chosen as starting material. Each mutant comprised a defined single nucleotide substitution in a gene involved in (i) GA biosynthesis, namely Grd2 that encodes GA3-oxidase, (ii) the GA receptor 'GID1', encoded by the Gse1 gene, and (iii) GA response, namely the Sln1 gene encoding the DELLA protein in barley. Grains of each dwarf line were treated with sodium azide, sown in the field, and allowed to self-fertilise to produce M1 seed. These were sown to produce M1 plants, from which $M_2$ grains were harvested. Resultant $M_2$ seedlings growing in soil were screened at the second-leaf stage for those showing more rapid growth than their dwarf siblings. Three different categories of mutant were recovered from a total of about $10^6$ grains sown, representing about 50,000 $M_1$ spikes.

The first category, of most relevance to this application, included 22 plants that grew more rapidly than their dwarf siblings. These were fully fertile and their progeny plants were uniform and showed rapid growth. In each case the presence of the original dwarfing mutation was confirmed by sequencing the appropriate PCR fragment. Their leaf elongation rates were higher than expected based on a dwarfing mutation being present. They showed a range in extent of growth enhancement, some with leaf elongation rates slightly but significantly faster than their dwarf parent, and others that elongated as fast as or even slightly faster than the corresponding tall wild-type plants (see below). Heights at maturity of the different overgrowth mutants ranged from intermediate between the dwarf parent and wild-type to as tall as the wild-type.

The second category, recovered only in the Sln1 d dwarf background, included three plants that grew more rapidly than their dwarfed siblings but still retained some degree of dwarfism. In the next generation the progeny of these plants consisted of dwarfs and typical elongated slender plants in an approximate 3:1 ratio. Further analysis (below) showed that they comprised new sln1 alleles in which a second mutation functioned as an intragenic suppressor of the Sln1d mutation.

The third category, observed in the GA biosynthesis and GA receptor dwarf backgrounds, consisted of typical elongated slender mutants. These were easily recognised by their distinctive highly elongated phenotype and pale green colour and, following transplantation, by their highly elongated stems and sterility. This class of mutant was expected because elongated sln1 null alleles are epistatic to defects in either GA biosynthesis or GA receptor function (Chandler and Robertson, 1999).

Example 5. Identification of Barley Mutations and Genetic Linkage Studies

DNA was prepared from slender plants of the three segregating lines in the Sln1d dwarf background (second category above) and the Sln1 gene was sequenced. Plants of each line contained a different, new mutation in the Sln1 gene resulting in a premature translation termination codon within the open reading frame (ORF). The new mutant alleles were derivatives of Sln1d and were therefore named Sln1d.1, Sln1d.2, Sln1d.3 (Table 1). They represented new intra-allelic mutations, where a second mutation converted the Sln1d dwarfing locus into a typical loss-of-function elongated sln1 allele. These plants were not studied further.

The entire Sln1 gene was sequenced in each of the overgrowth mutants (first category above), to confirm that the Sln1d allele was still present and to determine whether other mutations occurred in this gene since it was one of several candidate genes in which a new mutation might lead to an overgrowth phenotype. New mutations in the Sln1 ORF were found in 20 of the 22 plants. The mutations defined eleven new alleles of the Sln1 gene. Some of the plants carried identical mutations and were presumably siblings. Seven of the new Sln1 overgrowth alleles occurred in the Sln1d dwarf background and were therefore alleles comprising intra-genic suppressor mutations. These were named Sln1d.4-Sln1d.10. Three mutations occurred in the grd2b background (sln1m, sln1o, sln1s), and one occurred in the gseln background (sln1n). Each of the new alleles differed from its parental allele by a single nucleotide substitution which resulted in a single amino acid substitution in the SLN1 protein sequence. The amino acid substitutions that were obtained are listed in Table 1 (TR lines). They all occurred in the C-terminal 60% of the SLN1 protein, corresponding to the GRAS domain, and all of them corresponded to analogous mutations in the wheat mutants described above. Two identical mutational events were observed that resulted in the G829A amino acid substitution, one occurring in the Sln1d. 7 mutant population and the other in the sln1s population. These were independent mutational events since the former was a derivative of the Sln1d allele, whereas the latter occurred in a wild type Sln1 gene in the grd2b dwarf background.

The two remaining overgrowth lines (TR26, TR103) lacked any new mutation in the Sln1 ORF and potentially represented mutations in other genes. They occurred in a Sln1d dwarf background. Plants of these lines were crossed to Himalaya, together with Sln1d.5 as a positive control, to assess genetic linkage between the Sln1d dwarfing allele and the new overgrowth allele. The $F_2$ population from the control WT×Sln1d.5 cross showed the expected 3:1 (Sln1d.5:WT) distribution in maximal leaf elongation rates. There were no F2 individuals with the slow growth rate of the Sln1d parent, indicating complete linkage in this relatively small population between the original dwarfing mutation and the secondary overgrowth mutation. The secondary mutation was therefore an intra-genic suppressor mutation. A similar result was observed for the TR103×WT $F_2$ population, indicating that the overgrowth mutation in TR103 showed complete linkage to Sln1d. In contrast, the TR26× WT $F_2$ population included a majority of seedlings with growth rates the same as Sln1d, about 25% with growth rates the same as WT, and some seedlings with intermediate growth rates. These results were consistent with the overgrowth mutation in TR26 being in a gene that was unlinked to Sln1.

Several other candidate GA signalling genes in TR26 were sequenced. The GA receptor (Gse1) and two F-box candidate genes were the same in sequence as in the wild-type, but the sequence of Spindly1 revealed a single nucleotide substitution (spy1a, Table 1) that resulted in an amino acid substitution in the sixth TPR motif of SPY1. In Arabidopsis this region is important for SPY activity because it includes several mutant alleles (Silverstone et al., 2007). SPY1 encodes a negative regulator of GA signalling that was first identified in Arabidopsis, but functionally-related genes were later shown to exist in barley (Robertson et al., 1998) and rice (Shimada et al., 2006).

In summary, the 22 barley overgrowth mutants represented 13 independent mutational events. Eleven of these were new Sln1 alleles that caused single amino acid substitutions in SLN1. The twelfth was tightly linked to Sln1 but in an unidentified region, possibly a promoter mutation, and the thirteenth was a new allele in an unlinked gene, Spy1.

Example 6. Leaf Elongation Rates of Barley Comprising New Sln1 Alleles

The maximal daily rate of elongation ($LER_{max}$) achieved by the first leaf under standard conditions was a robust measure of GA responsiveness (Chandler and Robertson, 1999) and was therefore determined for all of the barley overgrowth lines and their parents (Table 5). The thirteen original overgrowth lines all had significantly higher $LER_{max}$ values than their respective dwarf parent, although the extent of growth enhancement varied in an allele-dependent manner. Three overgrowth alleles (sln1m, sln1n and sln1s) were compared in both their original dwarfing genetic background as well as after back-crossing to the tall WT background. Growth rates were consistently lower in dwarf backgrounds, indicating that overgrowth alleles were still subject to decreased GA signalling resulting from either impaired GA biosynthesis or GA receptor function. In a wild-type background, the overgrowth alleles tended to enhance growth rates.

Example 7. α-amylase Production by Endosperm Half-Grains

The production of α-amylase by endosperm half-grains of wild-type barley is dependent on the presence of an active GA. Therefore, monitoring α-amylase activity in the absence of an active GA provided a convenient measure of the extent of 'basal' GA signaling in the mutants. Two control lines with normal GA sensitivity (WT, grd2b) showed a near 15-fold increase in α-amylase activity over basal levels after 72 h incubation with $GA_3$ (Table 5). When overgrowth mutants and their dwarf parents were examined, the initial amount of α-amylase activity in mature endosperm half-grains was very low, but with incubation some overgrowth lines (Sln1d.4, Sln1d.7, Sln1d.8, Sln1d.9; Sln1d,spy1a; grd2b,sln1m; grd2b,sln1o; grd2b,sln1s) showed enhanced production of α-amylase relative to their dwarf parent, whereas others (Sln1d.5, Sln1d.6, Sln1d.10; gse1n,sln1n) did not. Among the overgrowth derivatives of Sln1d, the Sln1d.9 derivative was exceptional, accumulating very high levels of α-amylase at both 42 h and 72 h incubation, despite this line showing only a modest restoration of growth rate (Table 5).

Example 8. Other Traits Associated with Overgrowth Alleles

Plants of the overgrowth lines were close to normal in appearance during growth and at maturity, apart from differences in overall height. There was a range in heights among the nine overgrowth derivatives of Sln1d, although none were as tall as wild-type at maturity. Coleoptile lengths of overgrowth lines varied in general accordance with $LER_{max}$ values, and with final plant height.

One general feature of the overgrowth mutant barley plants was that they produced larger grains than their dwarf parents. In different harvests across different growing seasons, grain sizes were generally intermediate between the parental dwarf (grain mass about 40 mg) and the tall wild-type (grain mass about 55 mg). However several of the overgrowth lines that were as tall as wild-type at maturity had considerably larger heads and grains. In different greenhouse generations, the grains of grd2b and sln1m averaged 40% larger than those of the grd2b dwarf parent. When back-crossed to the Himalaya background, there was a 20% average increase observed in grain weight, and on outcrossing to the commercial variety Sloop, a 15% increase was observed in $BC_2$ material. A full analysis is made when $BC_3$ sister lines of Sloop are available.

Example 9. Description of Some Perfect Markers

The new alleles of Rht-B1c in wheat or barley are readily introduced into breeding programs and can be followed by marker assisted selection using a generic perfect marker for the overgrowth alleles. For example for wheat this involves PCR amplification between two primers, one of which is in the 2062 bp insertion in the Rht-B1c gene and the other of which is outside of the insertion, such as in the Rht-B1 coding region. Amplification of the appropriate product will only occur when the template DNA is from plant material that contains at least one copy of the overgrowth allele. Two examples of these are given in Table 2. These amplifications can be used to easily distinguish the new alleles derived from Rht-B1c from the other semi-dwarfing allele Rht-B1b and the Rht-D1b semidwarfing gene. Markers for the Rht-B1 gene other than the Rht-B1c allele or its derivative alleles can be generated easily by using a primer pair that flanks the insertion site in Rht-B1c.

Example 10. Backcrossing of Selected Alleles to Other Wheat Varieties

Crossing studies in barley as described above showed 100% coinheritance between the mutant Rht-B1 alleles and the overgrowth phenotype. In wheat, two crossing experiments were carried out. In the first, plants of six overgrowth lines were crossed with Maringa homozygous for the Rht-B1b allele (semidwarf), and plants of another four lines were crossed with Maringa homozygous for the wild-type Rht-B1a allele (tall). F1 progeny were selfed to produce F2 plants. In no case was the presence of any dwarf (homozygous Rht-B1c) plant detected in the F2 generation, indicating that for each of the ten lines, 100% genetic linkage was observed between the new Rht-B1 alleles and the overgrowth phenotype, and the new mutation suppressing dwarfism was in the Rht-B1 gene rather than being elsewhere in the genome. In the crosses with Rht-B1b, the expected inheritance patterns was shown for the overgrowth alleles and Rht-B1b in $F_2$ progeny, i.e. a 1:2:1 homozygous:heterozygous:homozygous ratio. In one of the crosses, the overgrowth parent (line TR550, Rht-B1c.8) was observed considerably more dwarfed than Rht-B1b, and the $F_2$ population showed segregation for height (homozygous overgrowth=65 cm, heterozygous=80-85 cm, homozygous Rht-B1b=95-100 cm) in a ratio not significantly different from 1:2:1, indicating the phenotype was determined by a single gene difference. Importantly, this moderately dwarfed overgrowth allele was associated with high dormancy in line TR550. Moreover, the F3 grain populations from field-grown F2 plants showed high dormancy for Rht-B1c.8 homozygous F2 plants, intermediate dormancy for Rht-B1c.8/Rht-B1b heterozygous F2 plants, and low dormancy for Rht-B1b homozygous F2 plants. This result indicated that the overgrowth allele was determining both the height and the dormancy phenotypes after crossing.

The four lines crossed with Maringa Rht-B1a were the lines designated 544, 612, 705 and 791 (Table 4), comprising the Rht-B1 alleles Rht-B1c.22, RhtB1c.23, Rht-B1c.24 and Rht-B1c.26, respectively. In each case, the expected genotypic segregation ratio was observed in the F2 generation. The F2 plants homozygous for the overgrowth allele showed the expected height reduction and the enhanced dormancy, indicating that the mutant Rht-B1 alleles could be crossed into other genetic backgrounds and retain the phenotypic effect. This also indicated the genetic linkage of the two phenotypes, namely the semi-dwarf plant height and the enhanced dormancy, caused by the mutant Rht-B1 alleles.

In the second experiment, selected overgrowth alleles were introduced into elite breeding lines by backcrossing, with the intention of replacing their existing semidwarfing gene (either Rht-B1b or Rht-D1b) with a new overgrowth allele. This was done in order to combine the phenotype of semidwarf height at maturity with other beneficial traits such as improved emergence and higher levels of grain dormancy. Crosses were made using plants of lines 544, 612, 705 and 791 as pollen donors with plants of 10 different elite wheat varieties, namely Crusader, EGA Gregory, Espada, Lincoln, Magenta, Yitpi, Young, KWS Chasmin, KWS Scirocco, McNeal and Outlook. $F_1$ grains were obtained from all crosses, and for three of the donor alleles were sown for further back-crossing to the recurrent parents. PCR markers were used to confirm that the F1 plants were hybrid. One of the four donors was slightly taller than plants having Rht-B1b, but three of the four donors were very similar in height to each other and to plants having Rht-B1b (semidwarf). One or two additional alleles that are slightly more dwarfed than Rht-B1b, and which have excellent grain dormancy are included in crossing experiments, such as Rht-B1c.3 and/or Rht-B1c.17.

Discussion

Overgrowth mutants of barley and wheat were isolated following mutagenesis of dwarf varieties containing a severely dwarfing allele. The mutants of interest retained the mutation that caused the severe dwarfing in the parental varieties, but grew faster than the parental plants because of a newly-induced mutation in the same Rht-B1 or Sln1 gene.

They were characterised by enhanced GA signalling, although the extent of the enhancement was specific for both the allele and the GA response being considered. The results indicated that the Della genes (Sln1 in barley, Rht-B1 in wheat) were the most frequent sites of overgrowth mutations. In only a single case was a different gene implicated—in barley one of the overgrowth mutants was due to a new mutation in Spy1.

Five independent lines of evidence supported the conclusion that the new mutations in the Della genes identified here were responsible for the overgrowth phenotypes, rather than an unlinked mutation or a mutation in a different gene, or simply being a general consequence of treatment with mutagen. First, for each of the 13 barley mutants a 'control' gene (Gse1) of about the same length as Sln1 was sequenced, and in no case was a base change detected. Second, the observed mutations were almost exclusively (in 30 of 31 mutants) a substitution of G to A, assuming that C to T represents G to A in the opposite DNA strand, similar to previous observations on azide-induced mutants at other loci including Gse1 (GA receptor), Sln1, genes for GA biosynthesis and starch biosynthesis. The redundancy in the genetic code predicted that with random G to A changes, 33% would have no corresponding amino acid substitution. However not a single case was observed of a silent nucleotide substitution in more than 90 newly-induced mutants each comprising a mutation in an open reading frame in these different barley genes. This absence indicated that mutations were recovered only where an amino acid change impaired protein function, leading to changes in phenotype. Third, the identified mutations nearly always involved amino acid residues that were conserved. For instance, the DELLA mutations involved amino acid residues that were identical, with only two or three exceptions, between cereal species and the taxonomically distant *Arabidopsis*. This can be seen in FIG. 8 which shows an alignment of wheat Rht-B1a and *Arabidopsis* GAI proteins, showing the conserved identical amino acids between the two sequences. Substitution of highly conserved amino acid residues would be much more likely to result in functional disruption to protein activity than changes in poorly conserved residues. Fourth, independent mutagenesis treatments gave examples of identical mutations, and therefore the corresponding identical amino acid substitutions, induced within barley, between barley and wheat, and within wheat. Fifth, following crossing and subsequent segregation, 100% linkage was always observed between the mutant phenotypes and the mutant gene sequences where linkage studies were completed.

Overgrowth alleles enhanced GA signalling and so were most likely to reduce either the amount of DELLA protein or its functional activity, the latter probably involving its interactions with other proteins. In some cases of differential splicing, there was also the potential for DELLA proteins with different in-frame amino acid insertions to be produced. For example, the mutants on occasions produced insertions either shorter or longer than the 30-amino acid insertion in the Rht-B1c protein. Amino acid substitutions could lead to increased degradation of DELLA if they resulted in a stronger affinity for either the GA-GID1 complex or the F-box subunit. Random changes were unlikely to strengthen protein interactions, although with an efficient mutant screen very rare events might still be recovered. Previous attempts to determine the contents of DELLA protein in different parts of the wheat plant by antibody procedures have been unsuccessful (Pearce et al., 2011). The inventors think it more likely that mutant DELLA proteins generated as described above have reduced affinity for other interacting protein partners. A considerable number of amino acid substitutions occurred in the LHR1 motif, a region which in *Arabidopsis* is involved in interactions with PIF4 and PIL5 (de Lucas et al., 2008; Feng et al., 2008). The differential effects of particular overgrowth alleles on growth versus α-amylase production in barley suggested that different regions of the DELLA protein interact with different protein partners to regulate these two responses.

It was unexpected that almost all of the identified overgrowth mutants were in a single gene, especially one that had been demonstrated to be of fundamental importance in growth control in a range of plant species under both controlled and field conditions. The preponderance of new alleles in the DELLA-encoding gene in both wheat and barley highlighted the importance of this gene in growth control. For instance, among overgrowth derivatives of the GA biosynthetic dwarf, mutants which might have increased the content of active GAs such as, for example, mutations in GA-catabolic genes were not identified despite the numbers of mutants analysed. The success in isolating many new mutants in wheat stemmed from the fact that the dwarfism due to semi-dominant alleles such as Rht-B1c was effectively a diploid trait, involving only one of the three genomes. This allowed selection of a range of loss-of-function (relative to Rht-B1c) derivative alleles, many of which involved intra-genic secondary mutations.

In both species, new alleles were recovered for an agronomically important trait, namely plant height. In addition, variation was observed in other GA-influenced traits, some of which were of practical interest. In barley larger grain size and increased production of α-amylase without the need for GA supplementation were both observed. Both traits were considered to be useful, for example for improved early seedling vigour and improved malting performance, respectively. The large collection of wheat mutants included mutants with a range in the extent of dwarfism beyond that of the existing Rht-1 semi-dwarfing alleles, which are expected to be of value in targeting specific alleles to specific environments (Flintham et al., 1997). There was also considerable variation observed in other GA traits of practical importance, e.g. increased coleoptile length relative to plants homozygous for Rht-1, and increased grain dormancy relative to plants homozygous for either Rht-B1a or Rht-B1b. These alleles should function as major genetic determinants for introducing a set of traits into breeding lines, expedited by the perfect molecular markers available for the gene.

The DELLA genes are highly conserved across various species. Sequence comparisons between wheat Rht-B1a protein *Arabidopsis thaliana* GAI proteins are shown in FIG. 8. As can be seen, there was a large degree of identity between these protein sequences across different species. Importantly, of the 20 amino acid substitutions found in the wheat overgrowth mutants, all except two or three were in amino acids conserved between the polypeptides encoded by the wheat and *Arabidopsis* genes. This was strongly supportive of the residues at these particular positions in the DELLA proteins in various species being particularly important to activity.

TABLE 1

Barley lines, genotypes and mutations

| Line | Genotype | Mutation[1] Nucleotide | Amino acid | Reference |
|---|---|---|---|---|
| Himalaya | WT | | | |
| *Sln1d and derivatives* | | | | |
| M640 | Sln1d | G137A | G46E | Chandler et al., 2002 |
| M763seg[2] | Sln1d/Sln1d.1 | G294A[3] | W98ter[3] | This study |
| M778seg[2] | Sln1d/Sln1d.2 | G1041A[3] | W347ter[3] | " |
| M783seg[2] | Sln1d/Sln1d.3 | G1839A[3] | W613ter[3] | " |
| TR1 | Sln1d.4 | C1469T[3] | S490F[3] | " |
| TR9 | Sln1d.5 | G839A[3] | R280H[3] | " |
| TR13 | Sln1d.6 | G803A[3] | R268H[3] | " |
| TR26 | Sln1d, spy1a | G812A (Spy1) | G271D (SPY1) | " |
| TR56[4] | Sln1d.7 | G829A[3] | A277T[3] | " |
| TR60[4] | Sln1d.8 | G691A[3] | V231M[3] | " |
| TR100[4] | Sln1d.9 | G1442A[3] | R481H[3] | " |
| TR103[4] | — | — | | " |
| TR107 | Sln1d.10 | G844T[3] | V282F[3] | " |
| *grd2b and derivatives* | | | | |
| M463 | grd2b | — | | Wolbang et al., 2004 |
| TR216 | grd2b, sln1s | G829A | A277T | This study |
| TR261 | grd2b, sln1m | G680A | G227E | " |
| TR305 | grd2b, sln1o | C1454T | S485F | " |
| *gse1n and derivatives* | | | | |
| M693 | gse1n | — | | Chandler et al., 2008 |
| TR407 | gse1n, sln1n | G710A | C237Y | This study |
| *Other derived lines* | | | | |
| M240[4] | sln1m | As above | | This study |
| M242[4] | sln1n | " | " | |
| M243[4] | sln1s | " | " | |
| M244seg[2] | sln1s/Sln1d.7 | " | " | |
| M247[4] | spy1a | " | " | |
| M248 | grd2b, spy1a | " | " | |
| M249 | gse1l, spy1a | " | " | |

Footnotes
[1]Coordinates refer to the positions in the HvSln1 coding sequence or SLN1 amino acid sequence from Himalaya (Genbank accession AK372064) starting at ATG and ending at TGA. For TR26, the coordinate refers to the position in the HvSpy1 (AF035820) coding sequence or SPY1 amino acid sequence, starting at ATG and ending at TGA.
[2]Grains are progeny from heterozygotes segregating at the Sln1 locus as indicated (the homozygous elongated slender plants are sterile).
[3]Sln1d.1-Sln1d.10 are derivatives of Sln1d, and contain the original Sln1d mutation in addition to the new substitutions indicated. Only the overgrowth lines (Sln1d.4-Sln1d.10) can be maintained as homozygotes.
[4]Lines established after two backcrosses to Himalaya before selecting for homozygosity of the allele shown.

TABLE 2

Nucleotide sequences of PCR primers used herein
(5' to 3')

| | | | SEQ ID NO |
|---|---|---|---|
| *Sequencing primers* | | | |
| 1 | Rht3 F40 | GGCAAGCAAAAGCTTGAGATAGAT | SEQ ID NO: 17 |
| | Rht3 R55 | GGTGCAGGGCAATAAGATG | SEQ ID NO: 18 |
| 2 | Rht3 F54 | GACAGCACCAGACGCTCAC | SEQ ID NO: 19 |
| | Rht3 R2 | GCTCTCGACCCAGGAGGAG | SEQ ID NO: 20 |
| 3 | Rht3 F48 | TGGAGCAGCTGGAGATGG | SEQ ID NO: 21 |
| | Rht3 R8 | TAGGGGCAGGACTCGTAGAA | SEQ ID NO: 22 |
| 4 | Rht3 F13 | GCGCTGGTGAAGCAGATAC | SEQ ID NO: 23 |
| | Rht3 R40 | TTCAAACTCGCGGTCACG | SEQ ID NO: 24 |
| *Insert primers* | | | |
| 1 | NHBF.2 | TCTCCTCCCTCCCCACCCCAAC | SEQ ID NO: 25 |
| | Rht3 R5 | GCGTCCGGTGGAGTTGCC | SEQ ID NO: 26 |
| 2 | Rht3 F6 | GTGTTTTTCCCAGCCCTCTT | SEQ ID NO: 27 |
| | Rht3 R2 | GCTCTCGACCCAGGAGGAG | SEQ ID NO: 28 |
| *D-genome specific primers* | | | |
| | Rht-D1F | GAGGTAGCTCGCGGATCA | SEQ ID NO: 29 |
| | Rht-D1R | CGTTCAAAACTCGCGAGA | SEQ ID NO: 30 |

TABLE 3

Wheat lines, Rht-B1 genotype and mutations

| Rht-B1 allele | Mutation in Rht-B1c | Amino acid substitution or effect |
|---|---|---|
| Rht-B1a | wild-type | none |
| Rht-B1b | | |
| Rht-B1c | Insertion | Insertion |
| Rht-B1c.1 | G2715A | G260E |
| Rht-B1c.2 | G2726A | V264M |
| Rht-B1c.3 | G2747A | A271T |

TABLE 3-continued

Wheat lines, Rht-B1 genotype and mutations

| Rht-B1 allele | Mutation in Rht-B1c | Amino acid substitution or effect |
|---|---|---|
| Rht-B1c.4 | G2829A | G298D |
| Rht-B1c.5 | G2831A | A299T |
| Rht-B1c.6 | G2849A | A305T |
| Rht-B1c.7 | C2865T | A310V |
| Rht-B1c.8 | C2966T | P344S |
| Rht-B1c.9 | C2972T | L346F |
| Rht-B1c.10 | G3065A | G377R |
| Rht-B1c.11 | G3076A | W380ter |
| Rht-B1c.12 | C3117T | P394L |
| Rht-B1c.13 | G3190A | W418ter |
| Rht-B1c.15 | G3477A | R514H |
| Rht-B1c.16 | C3507T | T524I |
| Rht-B1c.17 | C3519T | S528F |
| Rht-B1c.18 | G3624A | G563D |
| Rht-B1c.19 | G3697A | W587ter |
| Rht-B1c.20 | G3874A | W646ter |
| Rht-B1c.21 | G2792A | V286M |
| Rht-B1c.22 | CC2108TA | P58ter |
| Rht-B1c.23 | G3047A | D371N |
| Rht-B1c.24 | G2864A | A310T |
| Rht-B1c.25 | C3071T | Q379ter |
| Rht-B1c.26 | G3671A | E579K |
| Rht-B1c.27 | G148A | splicing |
| Rht-B1c.28 | G148T | splicing |
| Rht-B1c.29 | G147A | splicing |
| Rht-B1c.30 | G2084A | splicing |
| Rht-B1c.31 | G2335A | W133ter |
| Rht-B1c.32 | G2083A | Splicing |
| Rht-B1c.33 | G3841A | W635ter |
| Rht-B1c.34 | G3290T | E452ter |
| Rht-B1c.35 | C2705T | Q257ter |

TABLE 4

Phenotypes of overgrowth lines according to allele

| Rht-B1 allele | TR lines | Mature height (% tall) | Coleoptile length (% tall) | Dormancy Score Season 1 | Dormancy Score Season 2 |
|---|---|---|---|---|---|
| Rht-B1a | | 100 | 100 | 1.0 | 1.0 |
| Rht-B1b | | 81 | 84 | 1.0 | 1.0 |
| Rht-B1c | | 42 | 63 | 4.0 | 4.0 |
| Rht-B1c.1 | 704 | 90 | 91 | 2.0 | |
| | 713 | 90 | 91 | 2.0 | |
| | 714 | 92 | 83 | 2.0 | |
| | 761 | 89 | 94 | 1.0 | |
| | 762 | 92 | 97 | 2.0 | |
| | 778 | 95 | 88 | | |
| | 779 | 98 | 93 | 1 | |
| | 781 | 93 | 83 | 1 | |
| | 793 | 76 | 86 | | 2.0 |
| | 804 | 99 | 87 | 1.0 | |
| | 811 | 92 | 89 | 1.0 | |
| | 813 | 93 | 101 | 2 | |
| | 827 | 92 | 96 | 2.0 | |
| | 830 | 95 | 99 | | |
| | 845 | 96 | 73 | 2 | |
| | 873 | 98 | 97 | 1 | |
| | 879 | 88 | 93 | 1.0 | |
| Rht-B1c.1 | Mean | 92 | 91 | 1.5 | 2.0 |
| Rht-B1c.2 | 610 | 93 | 102 | 2.0 | |
| | 618 | 96 | 98 | 1.0 | |
| | 675 | 96 | 82 | 1.0 | |
| | 881 | 88 | 89 | 1 | |
| | 884 | 97 | 105 | 1 | |
| | 947 | 97 | 96 | 2.0 | |
| | 982 | 98 | 93 | | |
| Rht-B1c.2 | Mean | 95 | 95 | 1.3 | |
| Rht-B1c.3 | 917 | 70 | 75 | 4.0 | 2.0 |
| | 920 | 71 | 78 | 2.0 | 2.0 |

TABLE 4-continued

Phenotypes of overgrowth lines according to allele

| Rht-B1 allele | TR lines | Mature height (% tall) | Coleoptile length (% tall) | Dormancy Score Season 1 | Dormancy Score Season 2 |
|---|---|---|---|---|---|
| Rht-B1c.3 | Mean | 70 | 76 | 3.0 | 2.0 |
| Rht-B1c.4 | 885 | 67 | 85 | 4.0 | |
| Rht-B1c.5 | 725 | 65 | 67 | 3.0 | |
| Rht-B1c.6 | 875 | 59 | 70 | 2.0 | |
| | 983 | 71 | 84 | 2.0 | |
| Rht-B1c.6 | Mean | 65 | 77 | 2.0 | |
| Rht-B1c.7 | 543 | 77 | 91 | 1.0 | 2.0 |
| | 602 | 92 | 95 | 1.0 | |
| | 606 | 90 | 97 | 1.0 | |
| | 608 | 95 | 88 | 3.0 | |
| | 641 | 89 | 92 | | |
| | 646 | 89 | 94 | 3.0 | |
| | 679 | 90 | 79 | 1.0 | |
| | 680 | 93 | 90 | 1.0 | |
| | 710 | 91 | 95 | 2.0 | |
| | 784 | 98 | 102 | 1.0 | |
| | 785 | 94 | 91 | 1.0 | |
| | 790 | 97 | 92 | 1.0 | |
| | 943 | 82 | 88 | 1.0 | 1.0 |
| | 950 | 95 | 108 | 1.0 | |
| Rht-B1c.7 | Mean | 91 | 93 | 1.4 | |
| Rht-B1c.8 | 550 | 59 | 80 | 4.0 | 3.0 |
| | 770 | 59 | 86 | | |
| Rht-B1c.8 | Mean | 59 | 83 | 4.0 | 3.0 |
| Rht-B1c.9 | 703 | 86 | 90 | 3.0 | 3.0 |
| | 730 | 91 | 86 | 2.0 | 2.0 |
| Rht-B1c.9 | Mean | 88 | 88 | 2.5 | 2.5 |
| Rht-B1c.10 | 886 | 64 | 80 | 3.0 | |
| Rht-B1c.11 | 615 | 100 | 94 | 1.0 | |
| | 701 | 93 | 82 | 1.0 | |
| | 712 | 98 | 96 | 2.0 | |
| | 771 | 102 | 95 | 1.0 | |
| | 777 | 103 | 96 | 1.0 | |
| | 782 | 98 | 99 | 1.0 | |
| | 786 | 99 | 97 | 1.0 | |
| | 792 | 100 | 93 | | |
| | 875 | | | | |
| Rht-B1c.11 | Mean | 99 | 94 | 1.1 | |
| Rht-B1c.12 | 687 | 53 | 76 | 4.0 | |
| Rht-B1c.13 | 692 | 80 | 104 | | 1.0 |
| | 810 | 96 | 103 | 1.0 | |
| | 846 | 101 | 89 | 1.0 | |
| | 870 | 99 | 108 | 1.0 | |
| | 882 | 87 | 87 | 1.0 | |
| | 890 | 90 | 100 | | |
| | 979 | 97 | 105 | 1.0 | |
| | 990 | 90 | 91 | | |
| Rht-B1c.13 | Mean | 92 | 98 | 1.0 | |
| Rht-B1c.14 | 973 | 57 | 82 | 4.0 | |
| Rht-B1c.15 | 911 | 90 | 95 | 3.0 | |
| Rht-B1c.16 | 510 | 89 | 92 | 2.0 | 2.0 |
| Rht-B1c.17 | 603 | 78 | 84 | 1.0 | 3.0 |
| | 672 | 80 | 85 | 3.0 | 3.0 |
| | 686 | 76 | 89 | 2.0 | 3.0 |
| | 842 | 80 | 81 | 2.0 | 3.0 |
| Rht-B1c.17 | Mean | 78 | 85 | 2.0 | 3.0 |
| Rht-B1c.18 | 613 | 96 | 94 | 4.0 | |
| | 671 | 93 | 88 | 3.0 | |
| | 783 | 99 | 97 | 1.0 | |
| | 805 | 94 | 105 | 1.0 | |
| Rht-B1c.18 | Mean | 96 | 96 | 2.3 | |
| Rht-B1c.19 | 508 | 85 | 95 | 2.0 | 2.0 |
| | 611 | 94 | 97 | 1.0 | |
| | 648 | 97 | 112 | 2.0 | |
| | 667 | 98 | 98 | 1.0 | |
| Rht-B1c.19 | Mean | 93 | 100 | 1.5 | |
| Rht-B1c.20 | 601 | 93 | 90 | | |
| | 614 | 97 | 93 | 1.0 | |
| | 622 | 97 | 90 | 1.0 | |
| | 647 | 99 | 92 | 2.0 | |
| | 649 | 102 | 95 | 1.0 | |
| | 664 | 97 | 98 | 1.0 | |
| | 666 | 98 | 98 | 1.0 | |
| | 674 | 99 | 84 | 1.0 | |

TABLE 4-continued

Phenotypes of overgrowth lines according to allele

| Rht-B1 allele | TR lines | Mature height (% tall) | Coleoptile length (% tall) | Dormancy Score Season 1 | Dormancy Score Season 2 |
|---|---|---|---|---|---|
| | 677 | 99 | 96 | 1.0 | |
| | 682 | 95 | 97 | 1.0 | |
| | 683 | 98 | 90 | 1.0 | |
| | 684 | 99 | 87 | 1.0 | |
| | 685 | 103 | 84 | | |
| | 889 | 90 | | | |
| | 910 | 95 | 94 | 1.0 | |
| | 986 | 95 | 122 | | |
| | 989 | 84 | 91 | | |
| Rht-B1c.20 Mean | | 96 | 94 | 1.1 | |
| Rht-B1c.21 | 878 | 58 | 74 | 3.0 | |
| | 981 | 63 | 82 | 2.0 | |
| Rht-B1c.21 Mean | | 60 | 78 | 2.5 | |
| Rht-B1c.22 | 544 | 84 | 86 | 4.0 | 1.0 |
| Rht-B1c.23 | 612 | 74 | 82 | 2.0 | 3.0 |
| | 623 | 76 | 80 | 3.0 | 3.0 |
| Rht-B1c.23 Mean | | 75 | 81 | 2.5 | 3.0 |
| Rht-B1c.24 | 542 | 81 | 88 | | |
| | 688 | 85 | 92 | | 3.0 |
| | 705 | 77 | 90 | 3.0 | 3.0 |
| | 722 | 82 | 84 | 4.0 | 3.0 |
| | 723 | 84 | 84 | 2.0 | 3.0 |
| | 741 | 97 | 85 | 1.0 | |
| | 877 | 81 | 88 | 3.0 | 2.0 |
| Rht-B1c.24 Mean | | 84 | 87 | 2.6 | 2.8 |
| Rht-B1c.25 | 774 | 102 | 85 | 1.0 | |
| | 776 | 100 | 90 | 1.0 | |
| Rht-B1c.25 Mean | | 101 | 88 | 1.0 | |
| Rht-B1c.26 | 717 | 74 | 78 | 2.0 | 3.0 |
| | 773 | 76 | 75 | | 2.0 |
| | 791 | 80 | 83 | 3.0 | 3.0 |
| | 815 | 78 | 80 | 3.0 | |
| Rht-B1c.26 Mean | | 77 | 79 | 2.7 | 2.7 |
| Rht-B1c.27 | 507 | 77 | 67 | 1.0 | 1.0 |
| | 605 | 76 | 73 | 4.0 | 1.0 |
| | 624 | 84 | 76 | 2.0 | 1.0 |
| | 880 | 77 | 75 | 1.0 | 1.0 |
| Rht-B1c.27 Mean | | 79 | 73 | 2.0 | 1.0 |
| Rht-B1c.28 | 645 | 81 | 73 | 1.0 | 1.0 |
| Rht-B1c.29 | 901 | 83 | 72 | 1.0 | 1.0 |
| Rht-B1c.30 | 670 | 84 | 92 | 1.0 | 1.0 |
| | 678 | 82 | 85 | 1.0 | 1.0 |
| | 690 | 80 | 78 | 1.0 | |
| | 752 | 86 | 82 | 1.0 | 1.0 |
| Rht-B1c.30 Mean | | 83 | 84 | 1.0 | 1.0 |
| Rht-B1c.31 | 872 | 102 | 89 | 1 | |
| | 902 | 100 | 92 | 1 | |
| | 912 | 101 | 84 | 1 | |
| Rht-B1c.31 Mean | | 101 | 88.3 | 1.0 | |
| Rht-B1c.32 | 913 | 91 | 87 | 1.0 | |
| | 987 | 82 | 88 | | |
| Rht-B1c.32 Mean | | 87 | 87.5 | 1.0 | |
| Rht-B1c.33 | 644 | 98 | 101 | 1.0 | |
| | 729 | 98 | 112 | 1.0 | |
| | 750 | 95 | 92 | 1.0 | |
| | 789 | 95 | 91 | 1.0 | |
| Rht-B1c.33 Mean | | 97 | 99 | 1.0 | |
| Rht-B1c.34 | 728 | 98 | 91 | 1.0 | |
| | 745 | 95 | 89 | 1.0 | |
| Rht-B1c.34 Mean | | 96 | 90 | 1.0 | |
| Rht-B1c.35 | 914 | 95 | 87 | | |
| | 971 | 96 | 92 | 1.0 | |
| Rht-B1c.35 Mean | | 96 | 89.5 | 1.0 | |

TABLE 5

Leaf elongation rates and α-amylase production of barley overgrowth mutants

| Line | Genotype LER | $LER_{max}$ (mm·d$^{-1}$) | α-Amylase (Ceralpha units/grain) at: 0 h (×10$^3$) | 42 h | 72 h |
|---|---|---|---|---|---|
| Him | WT | 34.6 ± 0.9 | 1.6 | 0.36 ± 0.08 | 1.7 ± 0.09 |
| Him (GA$_3$) | WT | 52.3 ± 0.1 | nd | 9.81 ± 0.86 | 23.1 ± 2.8 |
| M640 | Sln1d | 9.2 ± 0.2 | 1.6 | 0.21 ± 0.01 | 0.19 ± 0.05 |
| M640 (GA$_3$) | Sln1d | 12.1 ± 0.3 | nd | nd | nd |
| TR1 | Sln1d.4 | 23.8 ± 0.5 | 2.5 | 0.26 ± 0.01 | 2.88 ± 0.27 |
| TR9 | Sln1d.5 | 15.5 ± 0.7 | 1.6 | 0.21 ± 0.01 | 0.16 ± 0.04 |
| TR13 | Sln1d.6 | 15.8 ± 0.6 | 1.8 | 0.20 ± 0.02 | 0.19 ± 0.04 |
| TR26 | | See Table 6 | | | |
| TR56 | Sln1d.7 | 16.7 ± 0.6 | 2.7 | 0.93 ± 0.22 | 3.24 ± 0.47 |
| TR60 | Sln1d.8 | 28.6 ± 0.9 | 3.6 | 0.82 ± 0.13 | 3.76 ± 0.23 |
| TR100 | Sln1d.9 | 20.2 ± 0.6 | 3.2 | 4.34 ± 0.13 | 14.6 ± 0.39 |
| TR103 | — | 16.1 ± 0.4 | 3.4 | 0.74 ± 0.10 | 0.39 ± 0.1 |
| TR107 | Sln1d.10 | 13.2 ± 0.3 | 2.4 | 0.39 ± 0.07 | 0.17 ± 0.03 |
| M463 | grd2b | 16.9 ± 0.8 | 2.5 | 0.67 ± 0.04 | 1.3 ± 0.2 |
| M463 (GA$_3$) | grd2b | 49.8 ± 0.8 | nd | 7.20 ± 0.73 | 18.9 ± 1.4 |
| TR216 | grd2b, sln1s | 23.2 ± 0.6 | 4.1 | 1.01 ± 0.12 | 4.16 ± 0.55 |
| TR261 | grd2b, sln1m | 38.4 ± 1.5 | 3.8 | 7.50 ± 0.24 | 18.1 ± 0.8 |
| TR305 | grd2b, sln1o | 32.9 ± 0.9 | 3.8 | 9.85 ± 0.43 | 16.9 ± 1.2 |
| M693 | gse1n | 19.7 ± 0.4 | 2.5 | 0.29 ± 0.05 | 0.11 ± 0.01 |
| M693 (GA$_3$) | gse1n | 35.3 ± 1.2 | nd | nd | nd |
| TR407 | gse1n, sln1n | 29.3 ± 0.5 | 9.9 | 0.27 ± 0.03 | 0.26 ± 0.13 |
| M240 | sln1m | 42.2 ± 1.6 | 6.5 | 11.6 ± 1.4 | 22.6 ± 2.3 |
| M242 | sln1n | 44.3 ± 3.1 | 3.0 | 1.07 ± 0.08 | 6.39 ± 1.52 |
| M243 | sln1s | 35.4 ± 0.9 | 3.8 | 3.66 ± 0.53 | 15.4 ± 0.9 |

TABLE 6

Effect of spy1a on growth rates and α-amylase production

| | | | α-Amylase (Ceralpha units/grain) at: | | |
|---|---|---|---|---|---|
| Line | Genotype | LER$_{max}$ (mm · d$^{-1}$) | 0 h (×10³) | 42 h | 72 h |
| Himalaya | WT | 34.6 ± 0.9 | 1.6 | 0.36 ± 0.08 | 1.7 ± 0.09 |
| M247 | spy1a | 37.6 ± 0.7 | 4.6 | 3.33 ± 0.22 | 12.5 ± 1.2 |
| M640 | Sln1d | 9.2 ± 0.2 | 1.6 | 0.21 ± 0.01 | 0.19 ± 0.05 |
| TR26 | Sln1d, spy1a | 17.1 ± 0.4 | 2.3 | 0.66 ± 0.10 | 2.84 ± 0.46 |
| M463 | grd2b | 17.7 ± 0.6 | 2.1 | 0.53 ± 0.1 | 3.7 ± 0.3 |
| M248 | grd2b, spy1a | 23.4 ± 0.5 | 3.6 | 10.2 ± 0.9 | 15.0 ± 1.8 |
| M691 | gse1l | 20.6 ± 0.4 | 1.6 | 0.07 ± 0.01 | 0.13 ± 0.03 |
| M249 | gse1l, spy1a | 25.8 ± 0.5 | 2.1 | 1.2 ± 0.2 | 7.2 ± 1.0 |

TABLE 7

Coleoptile lengths (in mm) of barley overgrowth lines

| Line | Genotype | Coleoptile length (mm) |
|---|---|---|
| Himalaya | WT | 100.3 ± 1.6 |
| M640 | Sln1d | 32.6 ± 1.8 |
| TR1 | Sln1d.4 | 65.8 ± 3.1 |
| TR9 | Sln1d.5 | 40.7 ± 2.4 |
| TR13 | Sln1d.6 | 45.2 ± 1.8 |
| TR26 | Sln1d, spy1a | 50.9 ± 1.0 |
| TR56 | Sln1d.7 | 60.7 ± 2.1 |
| TR60 | Sln1d.8 | 80.7 ± 2.5 |
| TR100 | Sln1d.9 | 66.9 ± 1.7 |
| TR103 | — | 58.5 ± 1.5 |
| TR107 | Sln1d.10 | 44.6 ± 2.0 |
| M463 | grd2b | 62.4 ± 2.2 |
| TR216 | grd2b, sln1s | 84.1 ± 1.7 |
| TR261 | grd2b, sln1m | 96.4 ± 3.5 |
| TR305 | grd2b, sln1o | 104.4 ± 2.0 |
| M693 | gse1n | 72.0 ± 1.5 |
| TR407 | gse1n, sln1n | 89.7 ± 1.5 |
| M240 | sln1m | 123.3 ± 2.7 |
| M242 | sln1n | 119.8 ± 2.3 |
| M243 | sln1s | 112.9 ± 4.6 |
| M247 | spy1a | 101.6 ± 2.5 |

TABLE 8

Plant height relative to tall variety (Rht-B1a allele) and grain dormancy scores for wheat plants of the mutant lines

| Rht allele | Height (% tall) | Dormancy score* 2012 |
|---|---|---|
| Rht-B1a | 100 | 0 |
| Rht-B1b | 81 | 0 |
| Rht-B1c | 42 | 8 |
| Rht-B1c.1 | 93 | 2 |
| Rht-B1c.2 | 95 | 0 |
| Rht-B1c.3 | 71 | 2 |
| Rht-B1c.4 | 67 | 4 |
| Rht-B1c.5 | 65 | 5 |
| Rht-B1c.6 | 71 | 5 |
| Rht-B1c.7 | 91 | 1.5 |
| Rht-B1c.8 | 59 | 5 |
| Rht-B1c.9 | 88 | 2 |
| Rht-B1c.14 | 57 | 3 |
| Rht-B1c.15 | 90 | 0.5 |
| Rht-B1c.16 | 89 | 0 |
| Rht-B1c.17 | 78 | 4 |
| Rht-B1c.18 | 96 | 1.5 |
| Rht-B1c.21 | 60 | 4 |
| Rht-B1c.22 | 84 | 1 |
| Rht-B1c.23 | 75 | 3 |
| Rht-B1c.24 | 82 | 3.5 |
| Rht-B1c.26 | 77 | 3.5 |
| Rht-B1c.27 | 81 | 1.5 |
| Rht-B1c.28 | 81 | 0 |
| Rht-B1c.29 | 83 | 0.5 |
| Rht-B1c.30 | 83 | 1 |
| Rht-B1c.36 | 55 | 4 |

*Dormancy score calculated as the number of weeks of storage of the grain in order for 50% of the grains to germinate in the germination test

REFERENCES

Achard et al., (2009). *J. Exptl Bot.* 60, 1085-1092.
Arana et al., (2011). *Proc. Natl. Acad. Sci. USA.* 108, 9292-9297.
Asano et al., (2009). *Mol. Genet Genomics* 281, 223-231.
Carol et al., (1995*Planta* 197, 414-417.
Chandler et al., (1999). *Plant Physiol.* 120, 623-632.
Chandler et al., (2002). *Plant Physiol* 129, 181-190.
Chandler et al., (2008). *Mol. Plant.* 1, 285-294.
de Lucas M et al., (2008). *Nature* 451, 480-484.
Dill et al., (2004). *Plant Cell* 16, 1392-1405.
Ellis et al., (2005). *Theor Appl Genet* 111, 423-430.
Feng et al., (2008). *Nature* 451, 475-479.
Flintham et al., (1997). *J. Agric. Sci.* 128, 11-25.
Fu et al., (2002). *Plant Cell* 14, 3191-3200.
Griffiths et al., (2006). *Plant Cell* 18, 3399-3414.
Hartweck, (2008). *Planta* 229, 1-13.
Hirano et al., (2010). *Plant Cell* 22, 2680-2696.
Hoogendoorn et al., (1988). In Miller T. E., Koebner, R. M. D., Proceedings of the Seventh International Wheat Genetics Symposium, Institute of Plant Science Research, Cambridge, U.K., pp. 1093-1100.
Ikeda et al., (2001). *Plant Cell,* 13, 999-1010.
Kuppusamy et al., (2009). *Plant Mol. Biol.* 69, 375-381.
Monna et al., (2002). *DNA Res.* 9, 11-17.
Murase et al., (2008). *Nature* 456, 459-463.
Pearce et al., (2011). *Plant Physiol.* DOI:10.1104/pp.111.183657.
Peng et al., J (1999*Nature* 400, 256-261.
Robertson et al., (1998). *Plant Cell* 10, 995-1007.
Sasaki et al., (2002). *Nature* 416, 701-702.
Sasaki et al., (2003). *Science* 299, 1896-1898.
Shimada et al., (2006). *Plant J.* 48, 390-402.
Shimada et al., (2008*Nature* 456, 520-544.
Silverstone et al., (1997). *Genetics* 146, 1087-1099.
Silverstone et al., (2007). *Plant Physiol.* 143, 987-1000.

Spielmeyer et al., (2002). *Proc Natl Acad Sci (USA)* 99, 9043-9048.
Sun, (2010). *Plant Physiol* 154, 567-570.
Ueguchi-Tanaka et al., (2005). *Nature* 437, 693-698.
Willige et al., (2007). *Plant Cell* 19, 1209-1220.
Wilson et al., (1995). *Plant Physiol* 108: 495-502.
Wolbang et al., (2004). *Plant Physiol* 134, 769-776.
Wu et al., (2011) *Plant Physiol* DOI:10.1104/pp.111.185272.
Yamaguchi, (2008). *Annu. Rev. Plant Biol.* 59, 225-251.
Yamamoto et al., (2010). *Plant Cell* 22, 3589-3602.
Zwar et al., (1995). *Planta* 197, 39-48.

---

The invention claimed is:

1. A wheat plant comprising an Rht-B1 allele which encodes an Rht-B1 polypeptide, the polypeptide comprising an N-terminal domain and a C-terminal domain, wherein the amino acid sequence of the C-terminal domain is at least 98% identical to amino acids 50-621 of SEQ ID NO:5, and wherein the amino acid sequence of the Rht-B1 polypeptide differs from the sequence set forth as SEQ ID NO:5 by at least (i) an insertion of one or more amino acids between amino acids 49 and 50 of SEQ ID NO:5, and (ii) one or more amino acid substitutions in the C-terminal domain relative to amino acids 50-621 of SEQ ID NO:5, wherein said wheat plant has an increased height relative to a wheat plant which is homozygous for a Rht-B1c allele and has a decreased height relative to a wheat plant which is homozygous for a Rht-B1a allele when the plants are grown under the same conditions.

2. The wheat plant as described in claim 1, wherein the wheat plant is homozygous for the Rht-B1 allele and has an increased plant height relative to a wheat plant which is homozygous for a Rht-B1c allele and a decreased height relative to a wheat plant which is homozygous for a Rht-B1a allele when the plants are grown under the same conditions.

3. The wheat plant of claim 2 in which the plant has increased fertility and/or produces an increased yield of grain relative to a wheat plant which is homozygous for a Rht-B1c allele.

4. The wheat plant of claim 3, wherein the yield of grain is about the same as, or greater than, a wheat plant which is homozygous for a Rht-B1b allele.

5. The wheat plant of claim 1, wherein the plant is homozygous for the Rht-B1 allele and has increased coleoptile length relative to a wheat plant which is homozygous for a Rht-B1c allele and wherein the coleoptile length is 80-100%, of the coleoptile length of a wheat plant which is homozygous for a Rht-B1a allele.

6. The wheat plant of claim 1 wherein the plant is homozygous for the Rht-B1 allele and is capable of producing grain which has increased dormancy relative to grain obtained from a wheat plant which is homozygous for a Rht-B1a allele.

7. The wheat plant of claim 1, wherein the Rht-B1 polypeptide comprises one or more amino acid substitutions in the N-terminal domain relative to amino acids 1 to 49 of SEQ ID NO:5.

8. The wheat plant of claim 1, wherein the insertion of one or more amino acids between amino acids 49 and 50 of SEQ ID NO:5 is an insertion of the sequence DSATPPDAPLVAAAGLAANETTHIKISANK (SEQ ID NO:14) or a variant thereof, wherein the sequence of the variant differs from SEQ ID NO:14 by amino acid substitutions, insertions or deletions of not more than 5 amino acids.

9. The wheat plant of claim 1, wherein the one or more amino acid substitutions in the C-terminal domain of the Rht-B1 polypeptide comprise a substitution of an amino acid corresponding to amino acid G260, V264, A271, G298, A299, A305, A310, P344, L346, G377, P394, R514, T524, S528, G563, V286, D371, or E579 with reference to SEQ ID NO: 3, or an amino acid corresponding to amino acid S493, R283, R271, A280, V234, R484, V285, G230, S488 or C240 with reference to SEQ ID NO:5.

10. The wheat plant of claim 2, wherein the one or more amino acid substitutions in the C-terminal domain of the Rht-B1 polypeptide comprise a substitution of an amino acid selected from the group consisting of G260E, V264M, A271T, G298D, A299T, A305T, A310V, P344S, L346F, G377R, P394L, R514H, T524I, S528F, G563D, V286M, D371N, A310T, and E579K, with reference to SEQ ID NO: 3, and S493F, R283H, R271H, A280T, V234M, R484H, V285F, G230E, S488F and C240Y, with reference to SEQ ID NO: 5.

11. The wheat plant of claim 1, wherein the Rht-B1 allele comprises a sequence variation relative to SEQ ID NO:1 which sequence variation is selected from the group consisting of G2715A, G2726A, G2747A, G2829A, G2831A, G2849A, C2865T, C2966T, C2972T, G3065A, C3117T, G3477A, C3507T, C3519T, G3624A, G2792A, CC2108TA, G3047A, G2864A, and G3671A.

12. The wheat plant of claim 1, wherein the plant is homozygous for the Rht-B1 allele.

13. The wheat plant of claim 1, wherein the wheat plant has a genetic background other than the wheat variety Maringa.

14. A process for producing wheat grain, comprising (i) growing a wheat plant as claimed in claim 1, and (ii) harvesting grain from the plant.

15. A process for producing bins of wheat grain comprising: a) reaping above-ground parts of wheat plants according to claim 1, b) threshing and/or winnowing the parts of the wheat plants to separate the grain from the remainder of the plant parts, and c) sifting and/or sorting the grain separated in step b), and loading the sifted and/or sorted grain into bins, thereby producing bins of grain.

16. Wheat grain obtained from the wheat plant of claim 1 the wheat grain comprising the Rht-B1 allele.

17. The wheat grain of claim 16, which wheat grain is capable of growing into a wheat plant when the grain is sown into soil, which plant is homozygous for the Rht-B1 allele and has an increased height relative to a wheat plant which is homozygous for the Rht-B1c allele and a decreased height relative to a wheat plant which is homozygous for the Rht-B1a allele when the plants are grown under the same conditions.

18. The wheat grain of claim 16, which wheat grain is capable of growing into a wheat plant when the grain is sown into soil, which plant is homozygous for the Rht-B1 allele and has increased fertility and/or produces an increased yield of grain relative to a wheat plant which is homozygous for the Rht-B1c allele.

19. The wheat grain of claim 18, wherein the yield of grain is about the same as, or greater than, a wheat plant which is homozygous for the Rht-B1b allele.

20. The wheat grain of claim 16, which wheat grain is capable of growing into a wheat plant when the grain is sown into soil, which plant is homozygous for the Rht-B1 allele and has increased coleoptile length relative to a wheat plant which is homozygous for the Rht-B1c allele.

21. The wheat grain of claim 16, which wheat grain is homozygous for the Rht-B1 allele and has increased dormancy relative to grain obtained from a wheat plant which is homozygous for the Rht-B1a allele.

22. The wheat grain of claim 16, wherein the wheat grain has one or more of the following characteristics:
the Rht-B1 polypeptide comprises one or more amino acid substitutions in the N-terminal domain relative to amino acids 1 to 49 of SEQ ID NO:5,
the insertion of one or more amino acids between amino acids 49 and 50 of SEQ ID NO:5 is an insertion of the sequence DSATPPDAPLVAAAGLAANETTHIKISANK (SEQ ID NO:14) or a variant thereof, wherein the sequence of the variant differs from SEQ ID NO:14 by amino acid substitutions, insertions or deletions of not more than 5 amino acids,
the one or more amino acid substitutions in the C-terminal domain of the Rht-B1 polypeptide comprise a substitution of an amino acid corresponding to amino acid G260, V264, A271, G298, A299, A305, A310, P344, L346, G377, P394, R514, T524, S528, G563, V286, D371, or E579 with reference to SEQ ID NO:3, or an amino acid corresponding to amino acid S493, R283, R271, G274, A280, V234, R484, V285, G230, S488 or C240 with reference to SEQ ID NO:5,
the wheat grain is as claimed in claim 16 and the Rht-B1 allele comprises a sequence variation relative to SEQ ID NO:1 which sequence variation is selected from the group consisting of G2715A, G2726A, G2747A, G2829A, G2831A, G2849A, C2865T, C2966T, C2972T, G3065A, C3117T, G3477A, C3507T, C3519T, G3624A, G2792A, CC2108TA, G3047A, G2864A, and G3671A,
the wheat grain is homozygous for the Rht-B1 allele, and the wheat grain has a genetic background other than the wheat variety Maringa.

23. The wheat grain of claim 16, which has been processed so that it is no longer able to germinate, which is kibbled, cracked, par-boiled, rolled, pearled, milled or ground grain.

24. A wheat cell derived from or capable of growing into the wheat plant of claim 1 comprising an Rht-B1 allele which encodes an Rht-B1 polypeptide, the polypeptide comprising an N-terminal domain and a C-terminal domain, wherein the amino acid sequence of the C-terminal domain is at least 98% identical to amino acids 50-621 of SEQ ID NO:5, and wherein the amino acid sequence of the Rht-B1 polypeptide differs from the sequence set forth as SEQ ID NO:5 by at least (i) an insertion of one or more amino acids between amino acids 49 and 50 of SEQ ID NO:5, and (ii) one or more amino acid substitutions in the C-terminal domain relative to amino acids 50-621 of SEQ ID NO:5.

25. The wheat cell of claim 24 wherein the wheat cell has one or more of the following characteristics:
the Rht-B1 polypeptide comprises one or more amino acid substitutions in the N-terminal domain relative to amino acids 1 to 49 of SEQ ID NO:5,
the insertion of one or more amino acids between amino acids 49 and 50 of SEQ ID NO:5 is an insertion of the sequence DSATPPDAPLVAAAGLAANETTHIKISANK (SEQ ID NO:14) or a variant thereof, wherein the sequence of the variant differs from SEQ ID NO:14 by amino acid substitutions, insertions or deletions of not more than 5 amino acids,
the one or more amino acid substitutions in the C-terminal domain of the Rht-B1 polypeptide comprise a substitution of an amino acid corresponding to amino acid G260, V264, A271, G298, A299, A305, A310, P344, L346, G377, P394, R514, T524, S528, G563, V286, D371, E579 with reference to SEQ ID NO:3, or an amino acid corresponding to amino acid S493, R283, R271, G274, A280, V234, R484, V285, G230, S488 or C240 with reference to SEQ ID NO:5,
the wheat cell is as claimed in claim 24 and the Rht-B1 allele comprises a sequence variation relative to SEQ ID NO:1 which sequence variation is selected from the group consisting of G2715A, G2726A, G2747A, G2829A, G2831A, G2849A, C2865T, C2966T, C2972T, G3065A, C3117T, G3477A, C3507T, C3519T, G3624A, G2792A, CC2108TA, G3047A, G2864A, and G3671A,
the wheat cell is homozygous for the Rht-B1 allele, and
the wheat cell has a genetic background other than the wheat variety Maringa.

26. A method of producing wheat flour, wholemeal, starch, starch granules or bran, the method comprising obtaining the grain of claim 16 and processing the grain to produce the flour, wholemeal, starch, starch granules or bran.

27. Wheat flour, wholemeal, or bran produced by the method of claim 26, the wheat flour, wholemeal or bran comprising the Rht-B1 allele.

28. A method of producing a food product, comprising mixing the grain of claim 16 or wheat flour, wholemeal, or bran produced therefrom, comprising the Rht-B1 allele, with at least one other food ingredient to produce the food product.

29. A method of producing starch, the method comprising obtaining the grain of claim 16 and processing the grain to produce the starch.

30. A method of producing ethanol, the method comprising fermenting starch obtained from the grain of claim 16, thereby producing the ethanol.

31. A method of feeding an animal, comprising providing to the animal the wheat plant of claim 1, wheat grain obtained therefrom and comprising the Rht-B1 allele, or a feed product comprising the wheat flour, wholemeal, or bran obtained therefrom and comprising the Rht-B1 allele.

32. A food product comprising wheat grain of claim 16 and/or an ingredient which is wheat flour, wholemeal, or bran produced from wheat grain of claim 16 and comprising the Rht-B1 allele or Rht-B1 polypeptide thereof.

33. The food product of claim 32, wherein the food product is leavened or unleavened bread, pasta, noodle, breakfast cereal, snack food, cake, pastry or a flour-based sauces.

34. A method of growing a wheat plant of claim 1, the method comprising (i) obtaining a sample comprising nucleic acid or protein extracted from a wheat plant or grain, (ii) detecting in the sample an Rht-B1 allele which encodes an Rht-B1 polypeptide or the Rht-B1 polypeptide, the Rht-B1 polypeptide comprising an N-terminal domain and a C-terminal domain, wherein the amino acid sequence of the C-terminal domain is at least 98% identical to amino acids 50-621 of SEQ ID NO:5, and wherein the amino acid sequence of the Rht-B1 polypeptide differs from the sequence set forth as SEQ ID NO:5 by at least (a) an insertion of one or more amino acids between amino acids 49 and 50 of SEQ ID NO:5, and (b) one or more amino acid substitutions in the C-terminal domain relative to amino acids 50-621 of SEQ ID NO:5 and (iii) growing a wheat plant having the Rht-B1 allele.

35. A method as claimed in claim 34 in which the wheat plant or grain comprises an Rht-B1 allele selected from the group consisting of Rht-B1c.1, Rht-B1c.2, Rht-B1c.3, Rht-B1c.4, Rht-B1c.5, Rht-B1c.6, Rht-B1c.7, Rht-B1c.8, Rht-B1c.9, Rht-B1c.10, Rht-B1c.12, Rht-B1c.15, Rht-B1c.16, Rht-B1c.17, Rht-B1c.18, Rht-B1c.21, Rht-B1c.22, Rht-B1c.23, Rht-B1c.24, and Rht-B1c.26.

36. A method of selecting a wheat plant from a population of wheat plants, the method comprising; i) crossing two plants of which at least one plant is a wheat plant according to claim 1 and growing a population therefrom; ii) genotyping each plant in said population of wheat plants, and iii) selecting said wheat plant on the basis of the genotyping.

37. A method of introducing an Rht-B1 allele into a wheat plant lacking said allele, the method comprising;
i) crossing a first parent wheat plant with a second parent wheat plant, wherein the second plant is a wheat plant according to claim 1, and
ii) backcrossing a progeny plant of the cross of step i) with a plant of the same genotype as the first parent plant to produce a plant with a majority of the genotype of the first parent but comprising said Rht-B1 allele.

38. The method of claim 36, wherein the progeny plant is genotyped for the presence or absence of said allele.

39. A method of trading wheat grain, comprising (a) obtaining wheat grain obtained from the wheat plant of claim 1 the wheat grain comprising the Rht-B1 allele, optionally comprising a step of
(i) cultivating the plant of claim 1
(ii) harvesting grain comprising the Rht-B1 allele from the plant,
and (b) trading the obtained grain for pecuniary gain.

40. The wheat plant of claim 1, wherein the insertion of one or more amino acids between amino acids 49 and 50 of SEQ ID NO:5 is an insertion of the sequence DSATPPDAPLVAAAGLAANETTHIKISANK (SEQ ID NO:14).

41. The wheat plant of claim 40, wherein the one or more amino acid substitutions in the C-terminal domain of the Rht-B1 polypeptide comprise a substitution of an amino acid corresponding to amino acid G260, V264, A271, G298, A299, A305, A310, P344, L346, G377, P394, R514, T524, S528, G563, V286, D371, or E579 with reference to SEQ ID NO: 3, or an amino acid corresponding to amino acid S493, R283, R271, A280, V234, R484, V285, G230, S488 or C240 with reference to SEQ ID NO:5.

42. The wheat plant of claim 40, wherein the one or more amino acid substitutions in the C-terminal domain of the Rht-B1 polypeptide comprise a substitution of an amino acid corresponding to amino acid G260, V264, A271, G298, A299, A305, A310, P344, L346, G377, P394, R514, T524, S528, G563, V286, D371 or E579 with reference to SEQ ID NO:3.

43. The wheat plant of claim 41, in which the one or more amino acid substitutions is selected from the group consisting of G260E, V264M, A271T, G298D, A299T, A305T, A310V, P344S, L346F, G377R, P394L, R514H, T524I, S528F, G563D, V286M, D371N, A310T, and E579K, with reference to SEQ ID NO: 3, and S493F, R283H, R271H, A280T, V234M, R484H, V285F, G230E, S488F and C240Y, with reference to SEQ ID NO: 5.

44. The wheat plant of claim 40, wherein the Rht-B1 allele comprises a sequence variation relative to SEQ ID NO:1 which sequence variation is selected from the group consisting of G2715A, G2726A, G2747A, G2829A, G2831A, G2849A, C2865T, C2966T, C2972T, G3065A, C3117T, G3477A, C3507T, C3519T, G3624A, G2792A, CC2108TA, G3047A, G2864A, and G3671A.

45. The wheat plant of claim 1, wherein the Rht-B1 polypeptide comprises amino acids 1-230 of SEQ ID NO:3.

46. The wheat plant of claim 45, wherein the one or more amino acid substitutions in the C-terminal domain of the Rht-B1 polypeptide comprise a substitution of an amino acid corresponding to amino acid G260, V264, A271, G298, A299, A305, A310, P344, L346, G377, P394, R514, T524, S528, G563, V286, D371, or E579 with reference to SEQ ID NO: 3, or an amino acid corresponding to amino acid S493, R283, R271, A280, V234, R484, V285, G230, S488 or C240 with reference to SEQ ID NO:5.

47. The wheat plant of claim 46, in which the one or more amino acid substitutions is selected from the group consisting of G260E, V264M, A271T, G298D, A299T, A305T, A310V, P344S, L346F, G377R, P394L, R514H, T524I, S528F, G563D, V286M, D371N, A310T, and E579K, with reference to SEQ ID NO: 3, and S493F, R283H, R271H, A280T, V234M, R484H, V285F, G230E, S488F and C240Y with reference to SEQ ID NO: 5.

48. The wheat plant of claim 1, wherein the Rht-B1 polypeptide is at least 99% identical in its amino acid sequence to SEQ ID NO:3.

49. The wheat plant of claim 48, wherein the one or more amino acid substitutions in the C-terminal domain of the Rht-B1 polypeptide comprise a substitution of an amino acid corresponding to amino acid G260, V264, A271, G298, A299, A305, A310, P344, L346, G377, P394, R514, T524, S528, G563, V286, D371, A310, or E579 with reference to SEQ ID NO: 3, or an amino acid corresponding to amino acid S493, R283, R271, A280, V234, R484, V285, G230, S488 or C240 with reference to SEQ ID NO:5.

50. The wheat plant of claim 49, in which the one or more amino acid substitutions is selected from the group consisting of G260E, V264M, A271T, G298D, A299T, A305T, A310V, P344S, L346F, G377R, P394L, R514H, T524I, S528F, G563D, V286M, D371N, A310T, and E579K, with reference to SEQ ID NO: 3, and S493F, R283H, R271H, A280T, V234M, R484H, V285F, G230E, S488F and C240Y with reference to SEQ ID NO: 5.

51. The wheat plant of claim 48, wherein the Rht-B1 polypeptide is at least 99.6% identical in its amino acid sequence to SEQ ID NO:3.

52. The wheat plant of claim 1, wherein the amino acid sequence of the C-terminal domain is at least 99% identical to amino acids 50-621 of SEQ ID NO:5.

53. The wheat plant of claim 40, wherein the Rht-B1 polypeptide differs in amino acid sequence from the sequence set forth as SEQ ID NO:3 by an amino acid substitution of amino acid G260, V264, A271, G298, A299, A305, A310, P344, L346, G377, P394, R514, T524, S528, G563, V286, D371 or E579.

54. The wheat plant of claim 53, wherein the amino acid substitution is selected from the group consisting of G260E, V264M, A271T, G298D, A299T, A305T, A310V, P344S, L346F, G377R, P394L, R514H, T524I, S528F, G563D, V286M, D371N, A310T and E579K.

55. Wheat grain produced by a wheat plant of claim 40, wherein the wheat grain comprises the Rht-B1 allele.

56. Wheat grain produced by a wheat plant of claim 41, wherein the wheat grain comprises the Rht-B1 allele.

57. Wheat grain produced by a wheat plant of claim 42, wherein the wheat grain comprises the Rht-B1 allele.

58. Wheat grain produced by a wheat plant of claim 43, wherein the wheat grain comprises the Rht-B1 allele.

59. Wheat grain produced by a wheat plant of claim 44, wherein the wheat grain comprises the Rht-B1 allele.

60. Wheat grain produced by a wheat plant of claim 45, wherein the wheat grain comprises the Rht-B1 allele.

61. Wheat grain produced by a wheat plant of claim 46, wherein the wheat grain comprises the Rht-B1 allele.

62. Wheat grain produced by a wheat plant of claim 47, wherein the wheat grain comprises the Rht-B1 allele.

63. Wheat grain produced by a wheat plant of claim 48, wherein the wheat grain comprises the Rht-B1 allele.

64. Wheat grain produced by a wheat plant of claim 49, wherein the wheat grain comprises the Rht-B1 allele.

65. Wheat grain produced by a wheat plant of claim 50, wherein the wheat grain comprises the Rht-B1 allele.

66. Wheat grain produced by a wheat plant of claim 51, wherein the wheat grain comprises the Rht-B1 allele.

67. Wheat grain produced by a wheat plant of claim 52, wherein the wheat grain comprises the Rht-B1 allele.

68. Wheat grain produced by a wheat plant of claim 53, wherein the wheat grain comprises the Rht-B1 allele.

69. Wheat grain produced by a wheat plant of claim 54, wherein the wheat grain comprises the Rht-B1 allele.

70. A wheat plant comprising an Rht-B1 allele which encodes an Rht-B1 polypeptide, the polypeptide comprising an N-terminal domain and a C-terminal domain, wherein the amino acid sequence of the C-terminal domain is at least 98% identical to amino acids 50-621 of SEQ ID NO:5, and wherein the amino acid sequence of the Rht-B1 polypeptide differs from the sequence set forth as SEQ ID NO:5 by at least (i) an insertion of one or more amino acids between amino acids 49 and 50 of SEQ ID NO:5, and (ii) one or more amino acid substitutions in the C-terminal domain relative to amino acids 50-621 of SEQ ID NO:5, and wherein the one or more substitutions in the C-terminal domain are selected from the group consisting of G260E, V264M, A271T, G298D, A299T, A305T, A310V, P344S, L346F, G377R, P394L, R514H, T524I, S528F, G563D, V286M, D371N, A310T, and E579K, with reference to SEQ ID NO: 3, and S493F, R283H, R271H, A280T, V234M, R484H, V285F, G230E, S488F and C240Y, with reference to SEQ ID NO: 5.

71. Wheat grain produced by a wheat plant of claim 70, wherein the wheat grain comprises the Rht-B1 allele.

* * * * *

SEQUENCE LISTING

```
<160> NUMBER OF SEQ ID NOS: 31

<210> SEQ ID NO 1
<211> LENGTH: 3892
<212> TYPE: DNA
<213> ORGANISM: Triticum aestivum

<400> SEQUENCE: 1
atgaagcgcg agtaccagga cgccggaggg agcggcggtg gccggggagg catgggctcg    60
tccgaggaca agataatggt gtcggggtcg gcggcggcgg gggaggggga ggaggtggac   120
gagctgctgg cggcgctcgg gtacaaggtg tgttggcgcc gcctcctcgc agcgccgttc   180
ttcttcctct catctctcat gaacacacac catggagaaa ctctacacac acacacacac   240
aaccaagaag aacaccggct gttactttgc acgagaggcc cttctccttg gtggaacaag   300
agactacatt gtgttttttcc cagccctctt ggctcacttt tctcattcat cttctccaac   360
ttaaatagct aagtacaaga ctgacccaag cacttgccag ccgccactct cgcagctgct   420
aacgcccact aactcatgca ctaggccact aatcacaact aactcatgca cgcatgcacc   480
acaccggcca ctatcacatg accgggcgac taacccacta gctacatgca tgcaactaga   540
taactacctt atccatgcac tccaggactc ggcaactcca ccggacgccc cgctcgtagc   600
agccgcggga cttgctgcta acgaaaccac gcacatcaag attagtgcta acatttcccc   660
ccttaatctt gacacgcctt gccgtcgacc gtcatcttga acgcctgagc tcgacgtctt   720
cacacgcctc cgcgcccgct gcgacgtgcc gtgcgcccgc ctgtcaccgg agttgatgca   780
gcttgcgtcg tcgtcgtcac ggccgtgacc cagcctgcgg acccgacccg acgcatcgac   840
gccggtcaca ccgccacgga cccgacctgg cgcactgacg ccggtcgcac cgtgctccct   900
cacgaccccg gcgacatacg ccgagctcct ccgccggcga cacgcctg cgtccctct   960 gcgtcccgca cgtcccgcac gcatccgacg tgcccgacga gcccgaccgc agcagtgcgt  1020
cccgcacgtc ccgcgcgcat tcgacgcgcc cgacgagccc gacagcacca gacgctcacc  1080
acgtgccgcc tccgcgtccg ccatggcagc caccacgccg cgcctacgtg ccacgcacct  1140
tccacggtcg ttgccccgag ccgtcgcgac ctatgcgcca ccacgcaggt ccttcgcgac  1200
ctcctcgtct ccgcgaccgc cgtgcccttc gcgcacactc ccacgtccc cgcgctccca  1260 gcccgcgctc ccgccgcgca cgtacgcggt ctgcgcaacc aggtccagcg cctcgacgcg  1320
gtccactccc gcggtcccga cgcgctcgac acgtccagtg cgcgcccata acacgcaccg  1380
gtcgcgtccg gctcgccgcc gcatcttatt gccctgcacc gccgcggcct ccatgccgcc  1440
atgcagtgcc tccacgccgc cacaccgtgt tgcaccgctg cgccaccacg cagcgcctcg  1500
gcggcctccg cggtcgccgc acgtacgacg tcaccgcccg ccgcctccgc cacgcgctcg  1560
ccgcgcgccg cagccgatgc ctccatgtcg gccgcgcatg ccccgtccgc cgcggacgcc  1620
accgcgcgcc acgccgcccc ctcgaacctt gtggctctga ataccaaatg ttggcgccgc  1680
ctcctcgcag cgccgttctt cttcctctca tctctcatga acacacacca tggagaaact  1740
ctacacacac acacacacaa ccaagaagaa caccggctgt tactttgcac gagaggccct  1800
tctccttggt ggaacaagag actacattgt gttttttccca gccctcttgg ctcactttc  1860
```

```
tcattcatct tctccaactt aaatagctaa gtacaagact gacccaagca cttgccagcc    1920
gccactctcg cagctgctaa cgcccactaa ctcatgcact aggccactaa tcacaactaa    1980
ctcatgcacg catgcaccac accggccact atcacatgac cgggcgacta acccactagc    2040
tacatgcatg caactagata actaccttat ccatgcactc caggactcgg caactccacc    2100
ggacgccccg ctcgtagcag ccgcgggact tgctgctaac gaaaccacgc acatcaagat    2160
tagtgctaac aaggtgcggg cgtccgacat ggcggacgtg gcgcagaagc tggagcagct    2220
ggagatggcc atggggatgg gcggcgtggg cgccggcgcc gcgcccgacg acagcttcgc    2280
cacccacctc gccacggaca ccgtgcacta aaccccacc gacctctcct cctgggtcga     2340
gagcatgctg tcggagctca acgcgccgcc gccgccccte ccgcccgccc cgcagctcaa    2400
cgcctccacc tcctccaccg tcaccggcgg cgggtacttc gatctcccgc cctccgtcga    2460
ctcctcctgc agcacctacg cgctgcggcc gatcccgtcc ccggccgtcg cgccggccga    2520 cctcccgcc gactccgtcg tgcgggatcc caagcggatg cgcactggcg gcagcagcac     2580
ctcgtcgtca tcctcatcgt cctctctcgg cggtggcggc gccaggagct ctgtggtgga    2640
ggctgccccg ccggtggccg ccgcggccgg tgcgccgcg ctgccggtcg tcgtggtcga     2700
cacgcaggag gccgggattc ggctggtgca cgcgctgctg gcgtgcgcgg aggccgtgca    2760
gcaggagaac ttctctgccg cggaggcgct ggtgaagcag ataccttgc tggccgcgtc     2820 ccagggcggc gccatgcgca aggtcgccgc ctacttcggc gaggccctcg ccgccgcgt     2880 cttccgcttc cgcccgcagc cggacagctc cctcctcgac gccgccttcg ccgacctcct    2940
ccacgcgcac ttctacgagt cctgcccta cctcaagttc gcccacttca ccgccaacca     3000
ggccatcctg gaggcgttcg ccggctgccg ccgcgtgcac gtcgtcgact tcggcatcaa    3060
gcaggggatg cagtggcccg ccttctcca ggccctggcg ctccgtcccg gcggccctcc     3120
ctcgttccgc ctcaccggcg tcggcccccc gcagccggac gagaccgacg ccttgcagca    3180
ggtgggctgg aagctcgccc agttcgcgca caccatccgc gtcgacttcc agtaccgcgg    3240
cctcgtcgcc gccacgctcg cggacctgga gccgttcatg ctgcagccgg agggcgagga    3300
ggacccgaac gaggagcccg aggtaatcgc cgtcaactcg gtcttcgaga tgcaccggct    3360
gctcgcgcag cccggcgccc tggagaaggt cctgggcacc gtgcgcgccg tgcggccgag    3420
gatcgtcacc gtggtggagc aggaggcgaa ccacaactcc ggcacattcc tggaccgctt    3480
caccgagtcc ctgcactact actccaccat gttcgattct ctggagggcg gcagctccgg    3540
cggcccatcg gaagtctcat ctggggcgg tgctgctcct gccgccgccg gcacggacca    3600
ggtcatgtcc gaggtgtacc tcggccggca gatctgcaac gtggtggcct gcgaggggc    3660 ggagcgcaca gagcggcacg agaccctggg gcagtggcgg aaccgcctcg gcaacgccgg    3720
gttcgagacc gtccacctgg gctccaatgc ctacaagcag gcgagcacgc tgctggcgct    3780
cttcgccggc ggcgacgggt acaaggtgga ggagaaggag ggctgcctga cgctggggtg    3840
gcacacgcgc ccgctgatcg ccacctccgc atggcgcctg ccgcgccgt ga             3892
```

<210> SEQ ID NO 2
<211> LENGTH: 1956
<212> TYPE: DNA
<213> ORGANISM: Triticum aestivum

<400> SEQUENCE: 2

```
atgaagcgcg agtaccagga cgccggaggg agcggcggtg gccggggagg catgggctcg      60
```

```
tccgaggaca agataatggt gtcggggtcg gcggcggcgg gggaggggga ggaggtggac    120
gagctgctgg cggcgctcgg gtacaaggac tcggcaactc caccggacgc cccgctcgta    180
gcagccgcgg gacttgctgc taacgaaacc acgcacatca agattagtgc taacaaggtg    240
cgggcgtccg acatggcgga cgtggcgcag aagctggagc agctggagat ggccatgggg    300
atgggcggcg tgggcgccgg cgccgcgccc gacgacagct cgccacccca cctcgccacg    360
gacaccgtgc actacaaccc caccgacctc tcctcctggg tcgagagcat gctgtcggag    420
ctcaacgcgc cgccgccgcc cctcccgccc gccccgcagc tcaacgcctc cacctcctcc    480
accgtcaccg gcggcgggta cttcgatctc ccgccctccg tcgactcctc ctgcagcacc    540
tacgcgctgc ggccgatccc gtccccggcc gtcgcgccgg ccgacctctc cgccgactcc    600
gtcgtgcggg atcccaagcg gatgcgcact ggcggcagca gcacctcgtc gtcatcctca    660
tcgtcctctc tcggcggtgg cggcgccagg agctctgtgg tggaggctgc cccgccggtg    720
gccgccgcgg ccgtgcgcc cgcgctgccg gtcgtcgtgg tcgacacgca ggaggccggg    780
attcggctgg tgcacgcgct gctggcgtgc gcggaggccg tgcagcagga gaacttctct    840
gccgcggagg cgctggtgaa gcagataccc ttgctggccg cgtcccaggg cggcgccatg    900
cgcaaggtcg ccgcctactt cggcgaggcc ctcgcccgcc gcgtcttccg cttccgcccg    960
cagccggaca gctccctcct cgacgccgcc ttcgccgacc tcctccacgc gcacttctac   1020
gagtcctgcc cctacctcaa gttcgcccac ttcaccgcca accaggccat cctggaggcg   1080
ttcgccggct ccgccgcgt gcacgtcgtc gacttcggca tcaagcaggg gatgcagtgg   1140 cccgccttc tccaggccct ggcgctccgt cccggcggcc ctccctcgtt ccgcctcacc   1200
ggcgtcggcc cccgcagcc ggacgagacc gacgccttgc agcaggtggg ctggaagctc   1260
gcccagttcg cgcacaccat ccgcgtcgac ttccagtacc gcggcctcgt cgccgccacg   1320
ctcgcggacc tggagccgtt catgctgcag ccggagggcg aggaggaccc gaacgaggag   1380
cccgaggtaa tcgccgtcaa ctcggtcttc gagatgcacc ggctgctcgc gcagcccggc   1440
gccctggaga aggtcctggg cacccgtgcgc ccgtgcggc cgaggatcgt caccgtggtg   1500
gagcaggagg cgaaccacaa ctccggcaca ttcctggacc gcttcaccga gtccctgcac   1560
tactactcca ccatgttcga ttctctggag gcggcagct ccggcggccc atccgaagtc   1620
tcatctgggg cggctgctgc tcctgccgcc gccggcacgg accaggtcat gtccgaggtg   1680
tacctcggcc ggcagatctg caacgtggtg gcctgcgagg gggcggagcg cacagagcgg   1740
cacgagaccc tggggcagtg gcggaaccgc ctcggcaacg ccgggttcga accgtccac    1800 ctgggctcca atgcctacaa gcaggcgagc acgctgctgg cgctcttcgc cggcggcgac   1860
gggtacaagg tggaggagaa ggagggctgc ctgacgctgg ggtggcacac gcgcccgctg   1920
atcgccacct ccgcatggcg cctggccgcg ccgtga                             1956
```

<210> SEQ ID NO 3
<211> LENGTH: 651
<212> TYPE: PRT
<213> ORGANISM: Triticum aestivum

<400> SEQUENCE: 3

```
Met Lys Arg Glu Tyr Gln Asp Ala Gly Gly Ser Gly Gly Gly Arg Gly
1               5                   10                  15

Gly Met Gly Ser Ser Glu Asp Lys Ile Met Val Ser Gly Ser Ala Ala
            20                  25                  30

Ala Gly Glu Gly Glu Glu Val Asp Glu Leu Leu Ala Ala Leu Gly Tyr
```

```
            35                  40                  45
Lys Asp Ser Ala Thr Pro Pro Asp Ala Pro Leu Val Ala Ala Gly
 50                  55                  60

Leu Ala Ala Asn Glu Thr Thr His Ile Lys Ile Ser Ala Asn Lys Val
 65                  70                  75                  80

Arg Ala Ser Asp Met Ala Asp Val Ala Gln Lys Leu Glu Gln Leu Glu
                 85                  90                  95

Met Ala Met Gly Met Gly Val Gly Ala Gly Ala Ala Pro Asp Asp
                100                 105                 110

Ser Phe Ala Thr His Leu Ala Thr Asp Thr Val His Tyr Asn Pro Thr
            115                 120                 125

Asp Leu Ser Ser Trp Val Glu Ser Met Leu Ser Glu Leu Asn Ala Pro
        130                 135                 140

Pro Pro Pro Leu Pro Pro Ala Pro Gln Leu Asn Ala Ser Thr Ser Ser
145                 150                 155                 160

Thr Val Thr Gly Gly Gly Tyr Phe Asp Leu Pro Pro Ser Val Asp Ser
                165                 170                 175

Ser Cys Ser Thr Tyr Ala Leu Arg Pro Ile Pro Ser Pro Ala Val Ala
                180                 185                 190

Pro Ala Asp Leu Ser Ala Asp Ser Val Val Arg Asp Pro Lys Arg Met
            195                 200                 205

Arg Thr Gly Gly Ser Ser Thr Ser Ser Ser Ser Ser Ser Ser Ser Leu
        210                 215                 220

Gly Gly Gly Gly Ala Arg Ser Ser Val Val Glu Ala Ala Pro Pro Val
225                 230                 235                 240

Ala Ala Ala Ala Gly Ala Pro Ala Leu Pro Val Val Val Asp Thr
                245                 250                 255

Gln Glu Ala Gly Ile Arg Leu Val His Ala Leu Leu Ala Cys Ala Glu
                260                 265                 270

Ala Val Gln Gln Glu Asn Phe Ser Ala Ala Glu Ala Leu Val Lys Gln
            275                 280                 285

Ile Pro Leu Leu Ala Ala Ser Gln Gly Gly Ala Met Arg Lys Val Ala
        290                 295                 300

Ala Tyr Phe Gly Glu Ala Leu Ala Arg Arg Val Phe Arg Phe Arg Pro
305                 310                 315                 320

Gln Pro Asp Ser Ser Leu Leu Asp Ala Ala Phe Ala Asp Leu Leu His
                325                 330                 335

Ala His Phe Tyr Glu Ser Cys Pro Tyr Leu Lys Phe Ala His Phe Thr
                340                 345                 350

Ala Asn Gln Ala Ile Leu Glu Ala Phe Ala Gly Cys Arg Arg Val His
            355                 360                 365

Val Val Asp Phe Gly Ile Lys Gln Gly Met Gln Trp Pro Ala Leu Leu
        370                 375                 380

Gln Ala Leu Ala Leu Arg Pro Gly Gly Pro Pro Ser Phe Arg Leu Thr
385                 390                 395                 400

Gly Val Gly Pro Pro Gln Pro Asp Glu Thr Asp Ala Leu Gln Gln Val
                405                 410                 415

Gly Trp Lys Leu Ala Gln Phe Ala His Thr Ile Arg Val Asp Phe Gln
                420                 425                 430

Tyr Arg Gly Leu Val Ala Ala Thr Leu Ala Asp Leu Glu Pro Phe Met
            435                 440                 445

Leu Gln Pro Glu Gly Glu Glu Asp Pro Asn Glu Glu Pro Glu Val Ile
        450                 455                 460
```

| | | | | | | | | | | | | | | |
|---|---|---|---|---|---|---|---|---|---|---|---|---|---|---|

Ala Val Asn Ser Val Phe Glu Met His Arg Leu Leu Ala Gln Pro Gly
465                 470                 475                 480

Ala Leu Glu Lys Val Leu Gly Thr Val Arg Ala Val Arg Pro Arg Ile
                485                 490                 495

Val Thr Val Val Glu Gln Glu Ala Asn His Asn Ser Gly Thr Phe Leu
            500                 505                 510

Asp Arg Phe Thr Glu Ser Leu His Tyr Tyr Ser Thr Met Phe Asp Ser
        515                 520                 525

Leu Glu Gly Gly Ser Ser Gly Gly Pro Ser Glu Val Ser Ser Gly Ala
    530                 535                 540

Ala Ala Ala Pro Ala Ala Ala Gly Thr Asp Gln Val Met Ser Glu Val
545                 550                 555                 560

Tyr Leu Gly Arg Gln Ile Cys Asn Val Val Ala Cys Glu Gly Ala Glu
                565                 570                 575

Arg Thr Glu Arg His Glu Thr Leu Gly Gln Trp Arg Asn Arg Leu Gly
            580                 585                 590

Asn Ala Gly Phe Glu Thr Val His Leu Gly Ser Asn Ala Tyr Lys Gln
        595                 600                 605

Ala Ser Thr Leu Leu Ala Leu Phe Ala Gly Gly Asp Gly Tyr Lys Val
    610                 615                 620

Glu Glu Lys Glu Gly Cys Leu Thr Leu Gly Trp His Thr Arg Pro Leu
625                 630                 635                 640

Ile Ala Thr Ser Ala Trp Arg Leu Ala Ala Pro
                645                 650

<210> SEQ ID NO 4
<211> LENGTH: 1866
<212> TYPE: DNA
<213> ORGANISM: Triticum aestivum

<400> SEQUENCE: 4

```
atgaagcgcg agtaccagga cgccggaggg agcggcggtg cgggggagg catgggctcg    60 tccgaggaca agatgatggt gtcggggtcg gcggcggcgg gggagggga ggaggtggac   120 gagctgctgg cggcgctcgg gtacaaggtg cgggcgtccg acatggcgga cgtggcgcag   180
aagctggagc agctggagat ggccatgggg atgggcggcg tgggcgccgg cgccgcgccc   240
gacgacagct tcgccaccca cctgccacg gacaccgtgc actacaaccc caccgacctc   300
tcctcctggg tcgagagcat gctgtcggag ctcaacgcgc cgccgccgcc cctcccgccc   360
gccccgcagc tcaacgcctc cacctcctcc accgtcaccg cggcgggta cttcgatctc   420 ccgccctccg tcgactcctc ctgcagcacc tacgcgctgc ggccgatccc gtccccggcc   480
gtcgcgccgg ccgacctctc cgccgactcc gtcgtgcggg atcccaagcg gatgcgcact   540
ggcggcagca gcacctcgtc gtcatcctca tcgtcctctc tcggcggtgg cggcgccagg   600
agctctgtgg tggaggctgc cccgccggtg gccgccgcgg ccgtgcgcc cgcgctgccg   660 gtcgtcgtgg tcgacacgca ggaggccggg attcggctgg tgcacgcgct gctggcgtgc   720
gcagaggccg tgcagcagga gaacttctct gccgcggagg cgctggtgaa gcagatacccc   780 ttgctggccc gtcccaggg cggcgccatg cgcaaggtcg ccgcctactt cggcgaggcc   840
ctcgcccgcc gcgtcttccg cttccgcccg cagccggaca gctccctcct cgacgccgcc   900
ttcgccgacc tcctccacgc gcacttctac gagtcctgcc cctacctcaa gttcgcccac   960
ttcaccgcca accaggccat cctggaggcg ttcgccggct gccgccgcgt gcacgtcgtc  1020
```

-continued

```
gacttcggca tcaagcaggg gatgcagtgg cccgcccttc tccaggccct ggcgctccgt    1080
cccggcggcc ctccctcgtt ccgcctcacc ggcgtcggcc cccgcagcc ggacgagacc     1140 gacgccttgc agcaggtggg ctggaagctc gcccagttcg cgcacaccat ccgcgtcgac    1200
ttccagtacc gcggcctcgt cgccgccacg ctcgcggacc tggagccgtt catgctgcag    1260
ccggagggcg aggaggaccc gaacgaggag cccgaggtaa tcgccgtcaa ctcggtcttc    1320
gagatgcacc ggctgctcgc gcagcccggc gccctggaga aggtcctggg caccgtcgcg    1380
gccgtgcggc cgaggatcgt caccgtggtg gagcaggagg cgaaccacaa ctccggcaca    1440
ttcctggacc gcttcaccga gtccctgcac tactactcca ccatgttcga ttctctggag    1500
ggcggcagct ccggcggccc atccgaagtc tcatctgggg cggctgctgc cctgccgcc    1560 gccggcacgg accaggtcat gtccgaggtg tacctcggcc ggcagatctg caacgtggtg    1620
gcctgcgagg gggcggagcg cacagagcgg cacgagaccc tggggcagtg gcggaaccgc    1680
ctcggcaacg ccgggttcga gaccgtccac ctgggctcca atgcctacaa gcaggcgagc    1740
acgctgctgg cgctcttcgc aggcggcgac gggtacaagg tggaggagaa ggagggctgc    1800
ctgacgctgg ggtggcacac gcgcccgctg atcgccacct ccgcatggcg cctggccgcg    1860
ccgtga                                                               1866
```

<210> SEQ ID NO 5
<211> LENGTH: 621
<212> TYPE: PRT
<213> ORGANISM: Triticum aestivum

<400> SEQUENCE: 5

```
Met Lys Arg Glu Tyr Gln Asp Ala Gly Gly Ser Gly Gly Gly Gly Gly
1               5                   10                  15

Gly Met Gly Ser Ser Glu Asp Lys Met Met Val Ser Gly Ala Ala
            20                  25                  30

Ala Gly Glu Gly Glu Glu Val Asp Glu Leu Leu Ala Ala Leu Gly Tyr
        35                  40                  45

Lys Val Arg Ala Ser Asp Met Ala Asp Val Ala Gln Lys Leu Glu Gln
    50                  55                  60

Leu Glu Met Ala Met Gly Met Gly Gly Val Gly Ala Gly Ala Ala Pro
65                  70                  75                  80

Asp Asp Ser Phe Ala Thr His Leu Ala Thr Asp Thr Val His Tyr Asn
                85                  90                  95

Pro Thr Asp Leu Ser Ser Trp Val Glu Ser Met Leu Ser Glu Leu Asn
            100                 105                 110

Ala Pro Pro Pro Leu Pro Pro Ala Pro Gln Leu Asn Ala Ser Thr
        115                 120                 125

Ser Ser Thr Val Thr Gly Gly Tyr Phe Asp Leu Pro Pro Ser Val
    130                 135                 140

Asp Ser Ser Cys Ser Thr Tyr Ala Leu Arg Pro Ile Pro Ser Pro Ala
145                 150                 155                 160

Val Ala Pro Ala Asp Leu Ser Ala Asp Ser Val Arg Asp Pro Lys
                165                 170                 175

Arg Met Arg Thr Gly Gly Ser Ser Thr Ser Ser Ser Ser Ser Ser
            180                 185                 190

Ser Leu Gly Gly Gly Gly Ala Arg Ser Ser Val Val Glu Ala Ala Pro
        195                 200                 205

Pro Val Ala Ala Ala Ala Gly Ala Pro Ala Leu Pro Val Val Val Val
    210                 215                 220
```

```
Asp Thr Gln Glu Ala Gly Ile Arg Leu Val His Ala Leu Leu Ala Cys
225                 230                 235                 240

Ala Glu Ala Val Gln Gln Asn Phe Ser Ala Glu Ala Leu Val
            245                 250                 255

Lys Gln Ile Pro Leu Leu Ala Ala Ser Gln Gly Gly Ala Met Arg Lys
            260                 265                 270

Val Ala Ala Tyr Phe Gly Glu Ala Leu Ala Arg Arg Val Phe Arg Phe
            275                 280                 285

Arg Pro Gln Pro Asp Ser Ser Leu Leu Asp Ala Ala Phe Ala Asp Leu
            290                 295                 300

Leu His Ala His Phe Tyr Glu Ser Cys Pro Tyr Leu Lys Phe Ala His
305                 310                 315                 320

Phe Thr Ala Asn Gln Ala Ile Leu Glu Ala Phe Ala Gly Cys Arg Arg
                325                 330                 335

Val His Val Val Asp Phe Gly Ile Lys Gln Gly Met Gln Trp Pro Ala
            340                 345                 350

Leu Leu Gln Ala Leu Ala Leu Arg Pro Gly Pro Pro Ser Phe Arg
            355                 360                 365

Leu Thr Gly Val Gly Pro Pro Gln Pro Asp Glu Thr Asp Ala Leu Gln
370                 375                 380

Gln Val Gly Trp Lys Leu Ala Gln Phe Ala His Thr Ile Arg Val Asp
385                 390                 395                 400

Phe Gln Tyr Arg Gly Leu Val Ala Ala Thr Leu Ala Asp Leu Glu Pro
                405                 410                 415

Phe Met Leu Gln Pro Glu Gly Glu Glu Asp Pro Asn Glu Glu Pro Glu
            420                 425                 430

Val Ile Ala Val Asn Ser Val Phe Glu Met His Arg Leu Leu Ala Gln
            435                 440                 445

Pro Gly Ala Leu Glu Lys Val Leu Gly Thr Val Arg Ala Val Arg Pro
450                 455                 460

Arg Ile Val Thr Val Val Glu Gln Glu Ala Asn His Asn Ser Gly Thr
465                 470                 475                 480

Phe Leu Asp Arg Phe Thr Glu Ser Leu His Tyr Tyr Ser Thr Met Phe
                485                 490                 495

Asp Ser Leu Glu Gly Gly Ser Ser Gly Gly Pro Ser Glu Val Ser Ser
            500                 505                 510

Gly Ala Ala Ala Ala Pro Ala Ala Gly Thr Asp Gln Val Met Ser
            515                 520                 525

Glu Val Tyr Leu Gly Arg Gln Ile Cys Asn Val Val Ala Cys Glu Gly
            530                 535                 540

Ala Glu Arg Thr Glu Arg His Glu Thr Leu Gly Gln Trp Arg Asn Arg
545                 550                 555                 560

Leu Gly Asn Ala Gly Phe Glu Thr Val His Leu Gly Ser Asn Ala Tyr
                565                 570                 575

Lys Gln Ala Ser Thr Leu Leu Ala Leu Phe Ala Gly Gly Asp Gly Tyr
            580                 585                 590

Lys Val Glu Glu Lys Glu Gly Cys Leu Thr Leu Gly Trp His Thr Arg
            595                 600                 605

Pro Leu Ile Ala Thr Ser Ala Trp Arg Leu Ala Ala Pro
610                 615                 620

<210> SEQ ID NO 6
<211> LENGTH: 7057
```

<212> TYPE: DNA
<213> ORGANISM: Triticum aestivum

<400> SEQUENCE: 6

```
gaattcgaac tgcacatacg tatgaagatg acctcaaggt ccaccgattt ggtccattga      60
ttatatatag ggctaattcc tccaaaagga ggatcggctc gcatcaccaa agtatccaac     120
gtactcagtc actcaagcgg atatgcatga ccggcacga cttggtcgcg ccgcgcgtac      180
cacacgagcg ggcgggtggg cgtcgcgatt accggtccg tgcgctcgta cagtcacgca      240
cagggcgcac caccgatctc gaacaatttt cactaccccc tccacacttc ttctgttgtg     300
gctgtacgac ggaaattatc ggcgcgggcg gtgcaccgtg gaccgatcgg gggcccacc      360
ggtgcagcag ctctggtcca cgaagacccg tggtatcccc gcggtgaccc ccacaggaag     420
aagcacatgg cgctgcctcc gcgataaggt ttgctaggcc tcgtgaacct accaggatcg     480
gctgcacgaa tcgtgaggcc tgcgtcggat ccgcccgcgg cgaccgtccg tggcccacgg     540
cagctcagcc gtctctgaaa gaaagtctgg tggcccacgg caactgtagt acgcgcgcgg     600
ggtggaaaat gataatgcgc gccagaagaa taaataaaca gaaataagga ttttctagc     660
aaggataaac aaaaataaag tgggagtcgg ggtccaatcc ggtatagccc atccctgctc     720
cgttttctgc accgccgggt ccagtgtgcc gacctgtggc ttttgacaaa tgtgtacagc     780
aaacacactg acgatctgct tagatcgatc agtattagtg gagaagataa gacaattata     840
tatgccatag tagtagttgt catatttagc tatatatttt cattgttaat tttaatcatc     900
ccacatatct aggagcatgc aagcattaat agttatatgt aacaccaaga gatagcgtgt     960
cattttttaat gacatgtgtg gcataagtac atgatctaaa agacttgagt ggatgataat    1020
ttttcctcca aatagaatac atttgtgaga ggaaaaacgt aagagctccg attacattga    1080
tcaatgatat gcatgtgaaa gcagtctcca acagattgga atgacatagc gcgtatataa    1140
caaggtatga tcaatgacaa aataatagcc attctccaag atgaatcaca tagctaacgc    1200
gacgaggagc atcccacggt cattatcatg tacccaccgc cagctcaagt gggtcctcat    1260
gttttttgct ttctcttctt tgcttgttgg atctagagct tcttttgtat tgacttgagt    1320
tatgagtgga tattgatggt gaacattgct gacatgagat tacctcttgt gattcccacc    1380
ggttcccccc ttatgttcgt cgtgctctta ctcgaatcca cctccaatca tgaagatcgg    1440
ccgcccctatg gcttgccctg tatcagaacc gtgtgtcgca ttagctatgt atacgtgtca    1500
cgtgaggcaa aatcacgcaa gtacttgaaa tgttggttgt tatatccttg gtaaatattc    1560
gtgctggatt caatcctaca aactaaacga ccagcacgaa aaagaatccc aagtcttgga    1620
atccattttg ccataagcca cagggagggc cacacggccg cagcgcacgg agagggagag    1680
ggagagggag tctgacgcag cagagagccc catcacccgc agcgtttttt ttctctaatt    1740
tgcgggatt tctggggtgg tgggctcagg atttgtaact ggatggcgaa gtttgtctgg     1800
tgataaagac gcgcgcgacg aatccgtcca tcgatccaac gctgtgcgcg tgttggcccg    1860
ggccccgccc gccagcgacc caccactgtg ccccgcccag atgccttccc ccccctccca    1920
tccatcgccc gatgccgtct acaactacta cgctgccgct ccctcgctgc tctgctcgct    1980
ctcctccctc cccaccccaa ccatccccgt ctcctcctcc ttcctcctct ccccgaccc     2040
tggatccaaa tcccggcccg ccccagagcc ggaatcgagg caagcaaaag cttgagatag    2100
atagagaggc gaggtaggga ggcgagaggc gagatcatga agcgcgagta ccaggacgcc    2160
ggagggagcg gcggtggcgg gggaggcatg ggctcgtccg aggacaagat gatggtgtcg    2220
```

```
gggtcggcgg cggcggggga gggggaggag gtggacgagc tgctggcggc gctcgggtac    2280
aaggtgcggg cgtccgacat ggcggacgtg gcgcagaagc tggagtagct ggagatggcc    2340
atggggatgg gcggcgtggg cgccggcgcc gcgcccgacg acagcttcgc cacccacctc    2400
gccacggaca ccgtgcacta caaccccacc gacctctcct cctgggtcga gagcatgctg    2460
tcggagctca acgcgccgcc gccgcccctc ccgcccgccc cgcagctcaa cgcctccacc    2520
tcctccaccg tcaccggcgg cgggtacttc gatctcccgc cctccgtcga ctcctcctgc    2580
agcacctacg cgctgcggcc gatcccgtcc ccggccgtcg cgccggccga cctctccgcc    2640
gactccgtcg tgcgggatcc caagcggatg cgcactggcg gcagcagcac ctcgtcgtca    2700
tcctcatcgt cctctctcgg cggtggcggc gccaggagct ctgtggtgga ggctgccccg    2760
ccggtggccg ccgcggccgg tgcgcccgcg ctgccggtcg tcgtggtcga cacgcaggag    2820
gccgggattc ggctggtgca cgcgctgctg gcgtgcgcag aggccgtgca gcaggagaac    2880
ttctctgccg cggaggcgct ggtgaagcag ataccttgc tggccgcgtc ccagggcggc    2940
gccatgcgca aggtcgccgc ctacttcggc gaggccctcg cccgccgcgt cttccgcttc    3000
cgcccgcagc cggacagctc cctcctcgac gccgccttcg ccgacctcct ccacgcgcac    3060
ttctacgagt cctgccccta cctcaagttc gcccacttca ccgccaacca ggccatcctg    3120
gaggcgttcg ccggctgccg ccgcgtgcac gtcgtcgact tcggcatcaa gcaggggatg    3180
cagtggcccg ccttctcca ggccctggcg ctccgtcccg gcggccctcc ctcgttccgc    3240
ctcaccggcg tcggcccccc cagccggac gagaccgacg ccttgcagca ggtgggctgg    3300
aagctcgccc agttcgcgca caccatccgc gtcgacttcc agtaccgcgg cctcgtcgcc    3360
gccacgctcg cggacctgga gccgttcatg ctgcagccgg agggcgagga gaacccgaac    3420
gaggagcccg aggtaatcgc cgtcaactcg gtcttcgaga tgcaccggct gctcgcgcag    3480
cccggcgccc tggagaaggt cctgggcacc gtgcgcgccg tgcggccgag gatcgtcacc    3540
gtggtggagc aggaggcgaa ccacaactcc ggcacattcc tggaccgctt caccgagtcc    3600
ctgcactact actccgccat gttcgattct ctggagggcg gcagctccgg cggcccatcc    3660
gaagtctcat ctggggcggc tgctgctcct gccgccgccg gcacggacca ggtcatgtcc    3720
gaggtgtacc tcggccggca gatctgcaac gtggtggcct gcgaggggc ggagcgcaca    3780 gagcggcacg agaccctggg gcagtggcgg aaccgcctcg gcaacgccgg gttcgagacc    3840
gtccacctgg gctccaatgc ctacaagcag gcgagcacgc tgctggcgct cttcgcaggc    3900
ggcgacgggg acaaggtgga ggagaaggag ggctgcctga cgctggggtg gcacacgcgc    3960
ccgctgatcg ccacctccgc atggcgcctg gccgcgccgt gaccgcgagt tttgaacgct    4020
gtaagtacac atcgtgagca tggaggacga cacaaccccg gcggccgccc cggctctccg    4080
gcgcacgcac gcacgcacgc tcttgaagaa gaagaagaag ctaaatgtca tgtcagtgaa    4140
cgctgaattg cagcggccgg ccacgatcga ccgtccggcg tgaagagacg gacgacgacg    4200
aactccgagc cgaccatccc accggcatgt agtaatgtaa tcccttcttc gtccccagtt    4260
ctccaccgcc tccatgatca cccgtaaaac tcccaagccc tactactact actactacta    4320
ctactactac tatcatgttt aaatgtctat tattgcaatg tgtaattcct ccaatcgctc    4380
atatcaaaat aagcgcgggc cggactttgt tagctgctcc aatgagaatg aaaatgaatt    4440
ttgtacgcaa cgcacgtccg aaactgagcc gagctctgtt ctgttcttga tgttcatggt    4500 gtcttggtg atcaacttag cttccttgc cgtgtttgag ggcttgccga aggaagtttc    4560
ccgatctagg agttgctgca aatgatgcgg cgtgttggaa agatctcgtg tagtttcccc    4620
```

```
ctgcggtgtg tggtcacccc gccgctggct gtttcctgat ctaaaaatga acctgcacgt    4680
tagttggaga gggggcgca tcagcatcag catcaccacc gatcggccaa ggcttcggcc     4740
ctgctgccgg agcaatcagt tgatcaaaac cgaataccgt ttctgcacaa cagcttgccg   4800
tctaagggca tgtacaatgg tggcatatgg atacatatgt cccatgacaa aaagtaattt   4860
gaggcaccta catttagttt ttcttcccaa ggcaacccac agtaagaaga ctcattaaga   4920
aatagaaaat aaaaatttta gtacacatgc atctctactt ttcacttcaa ttttttcagc   4980
ttttgtcacc ggacttcaag cacccgcctc ctggagagga tcccgctttc ctatccgaat   5040
ctactttacg tcatatccga tcctacatgg catgtgaggc atcaccttga ggctatgcat   5100
tgtacatgac atgagtgccg caccgccgta gcaatcagct cgatgatcaa agcatgttat   5160
acccgagcgc atacgcatta ccggcggcgc tgatcgtcgt cggggagcag taacttttgc   5220
gggatgggat tggcgcagag gcgggcggag cagtaacttt tgcgggatgg gattggcgca   5280
gaggcgggcg gagcagtgga aacctgagag gccactgctg gctggcgtgg cgcattgcca   5340
cttctgttgg tgatttctgc ctctgcacag tgaccagcgt ggccggccgg cctatcgaaa   5400
ctcaccgcgc cgcgcggtaa aatgttcgtc cgttgggcgg gggcgtgggg ctgggctgca   5460
gcacagagaa cacttaaccc gcgtgcatca tcaccgccag ccagccggcc agccgcggcg   5520
tccgtggtgt acccacggga gcttctgaca gcagtaaaaa aaacacaagg cggtgtgtgg   5580
atgggccgtg gagatctggc gtgcgtggcc gcaaatctcc cccgccggtg acgtcgggcc   5640
tgcgagcttt ttatttaacc tggcctgccc gaggcgaggc ccggcggcca atgggaggcc   5700
gcggtagaag tttgggcggg gggaaaggaa agggaaggag gtgggcggca gcaacagctg   5760
tccaatcggg atcaggtggg cgtgtcaggg agatgatggt ggtgggccc ggccgtcggc    5820
ctctgcccct ccctgtcgat cccagtcaga gacacacacc gctagctagc tgtggctact   5880
agcagctctg ggcctctgac tcacctcctg ctcggcccgg ggacagcccg gccccaccgc   5940
cgataaagaa aacggaaaaa ggagagggga aatagttcta gcgtgggtgg gggccccaac   6000
cccagctccg ccgatccggg gccgggggt caattcgcgc gtgtgtgacc ccgacgggcg    6060
cgatgatgcc gccccccgtgc cgtgcccgcg cacgcctcgc cgctcccccgg tcgccgggtc  6120
agctccgtcg cgcgccgcgg cggcgacgtg tagcccgccc ctgctcgccc cacatgcaca   6180
cggaccacgc cggtgacctg acccatccaa ccgaacccga tcctatcctc gcgtcgcggc   6240
catgccgagg gatgggcggt tttgttatcc cgcggcgcgc cacgaggccg gtcctatccg   6300
acggccggcg caccggcgca tggaattgtt gcgctgggcg cggcgggggg acgtgtgagc   6360
gtgtccgtgc atgggtacgc gtgggattcc gtgcgattcc gctggccatt ggccacgcag   6420
ctgcaaggga agggtggtgg tggttgggtg ggaggatcga ttcggtggat gtgacccggt   6480
gtggtggtgc gcgcacatgc gacggggtgg tgcgggtcag gggctcatcg gccgtcttgt   6540
gctcgaacca ctctctgcag gggaaatgcg ccggagcccg cgtcaactcg gcggtcacac   6600
cgatcacagg ataaggttga cggacgagat gttttctctt gttcgatata agaaagggtg   6660
gcgttaaagc gactgcacgc agaggcgtca ggtctatata aagaagattt ttttttttaca   6720
ttcggaaaat gtgggctagt actcctacat acatatgttt tctttttttt ttgagcatca   6780
tacatatgtt ttctttgatt tgaaggcgcg taaatatgga ttgacttatt tattggaact   6840
ggaatattga ttacgtaagt tatttattgg agctggacat gcttacccag tgcgattaat   6900
gctgcaacta cctccattct gatttattag cccccttgta tttaaggcaa aaaaaaaga    6960
```

```
aattaaggtc atagtttgac cataatttca actaataaag taaaagttaa acataggaga    7020
aataatatta tccgaaacta ttgtcaaata tgaattc                             7057
```

<210> SEQ ID NO 7
<211> LENGTH: 555
<212> TYPE: PRT
<213> ORGANISM: Triticum aestivum

<400> SEQUENCE: 7

```
Met Ala Met Gly Met Gly Gly Val Gly Ala Gly Ala Ala Pro Asp Asp
1               5                   10                  15

Ser Phe Ala Thr His Leu Ala Thr Asp Thr Val His Tyr Asn Pro Thr
            20                  25                  30

Asp Leu Ser Ser Trp Val Glu Ser Met Leu Ser Glu Leu Asn Ala Pro
        35                  40                  45

Pro Pro Pro Leu Pro Pro Ala Pro Gln Leu Asn Ala Ser Thr Ser Ser
    50                  55                  60

Thr Val Thr Gly Gly Tyr Phe Asp Leu Pro Pro Ser Val Asp Ser
65                  70                  75                  80

Ser Cys Ser Thr Tyr Ala Leu Arg Pro Ile Pro Ser Pro Ala Val Ala
                85                  90                  95

Pro Ala Asp Leu Ser Ala Asp Ser Val Val Arg Asp Pro Lys Arg Met
            100                 105                 110

Arg Thr Gly Gly Ser Ser Thr Ser Ser Ser Ser Ser Ser Ser Ser Leu
        115                 120                 125

Gly Gly Gly Gly Ala Arg Ser Ser Val Val Glu Ala Ala Pro Pro Val
    130                 135                 140

Ala Ala Ala Ala Gly Ala Pro Ala Leu Pro Val Val Val Val Asp Thr
145                 150                 155                 160

Gln Glu Ala Gly Ile Arg Leu Val His Ala Leu Leu Ala Cys Ala Glu
                165                 170                 175

Ala Val Gln Gln Glu Asn Phe Ser Ala Ala Glu Ala Leu Val Lys Gln
            180                 185                 190

Ile Pro Leu Leu Ala Ala Ser Gln Gly Gly Ala Met Arg Lys Val Ala
        195                 200                 205

Ala Tyr Phe Gly Glu Ala Leu Ala Arg Arg Val Phe Arg Phe Arg Pro
    210                 215                 220

Gln Pro Asp Ser Ser Leu Leu Asp Ala Ala Phe Ala Asp Leu Leu His
225                 230                 235                 240

Ala His Phe Tyr Glu Ser Cys Pro Tyr Leu Lys Phe Ala His Phe Thr
                245                 250                 255

Ala Asn Gln Ala Ile Leu Glu Ala Phe Ala Gly Cys Arg Arg Val His
            260                 265                 270

Val Val Asp Phe Gly Ile Lys Gln Gly Met Gln Trp Pro Ala Leu Leu
        275                 280                 285

Gln Ala Leu Ala Leu Arg Pro Gly Gly Pro Ser Phe Arg Leu Thr
    290                 295                 300

Gly Val Gly Pro Pro Gln Pro Asp Glu Thr Asp Ala Leu Gln Gln Val
305                 310                 315                 320

Gly Trp Lys Leu Ala Gln Phe Ala His Thr Ile Arg Val Asp Phe Gln
                325                 330                 335

Tyr Arg Gly Leu Val Ala Ala Thr Leu Ala Asp Leu Glu Pro Phe Met
            340                 345                 350

Leu Gln Pro Glu Gly Glu Glu Asn Pro Asn Glu Glu Pro Glu Val Ile
```

```
                355                 360                 365
Ala Val Asn Ser Val Phe Glu Met His Arg Leu Leu Ala Gln Pro Gly
    370                 375                 380
Ala Leu Glu Lys Val Leu Gly Thr Val Arg Ala Val Arg Pro Arg Ile
385                 390                 395                 400
Val Thr Val Val Glu Gln Ala Asn His Asn Ser Gly Thr Phe Leu
                405                 410                 415
Asp Arg Phe Thr Glu Ser Leu His Tyr Tyr Ser Ala Met Phe Asp Ser
                420                 425                 430
Leu Glu Gly Gly Ser Ser Gly Gly Pro Ser Glu Val Ser Ser Gly Ala
                435                 440                 445
Ala Ala Pro Ala Ala Ala Gly Thr Asp Gln Val Met Ser Glu Val
    450                 455                 460
Tyr Leu Gly Arg Gln Ile Cys Asn Val Val Ala Cys Glu Gly Ala Glu
465                 470                 475                 480
Arg Thr Glu Arg His Glu Thr Leu Gly Gln Trp Arg Asn Arg Leu Gly
                485                 490                 495
Asn Ala Gly Phe Glu Thr Val His Leu Gly Ser Asn Ala Tyr Lys Gln
                500                 505                 510
Ala Ser Thr Leu Leu Ala Leu Phe Ala Gly Gly Asp Gly Tyr Lys Val
                515                 520                 525
Glu Glu Lys Glu Gly Cys Leu Thr Leu Gly Trp His Thr Arg Pro Leu
                530                 535                 540
Ile Ala Thr Ser Ala Trp Arg Leu Ala Ala Pro
545                 550                 555

<210> SEQ ID NO 8
<211> LENGTH: 3463
<212> TYPE: DNA
<213> ORGANISM: Triticum aestivum

<400> SEQUENCE: 8
tatacatgtt gtggtactag ttgtcatatt tagctatata tttttcaata ttaattttaa     60
tcaacccaca tatctaggag catgcaagca ttaatagtta gacttaacac caagagatag    120
tgtgtctttc ttaataacat gtgtggcata agtacacgat ctaaaagact tgagtcgatg    180
ataatttgtc ctccaaaaag aatacatttg tgagagatag aacacaagaa ctccgatcac    240
attgatcaat gatctgcatg tgaaaatggt ctccagcgga ttagaatgac atagcgcgta    300
tttaacaaga tatggtcaat gacaaaataa tagtcactgt acaagatgaa tgacatagct    360
aaactgacgc ggagcatccc atggtcatca ccatgcacac accgccaact caagtgggtc    420
ctaatgttat ttgcttttctc tagtttgctt gttggatcta acggttcttt tgtattaact    480
tgagttatga gtggatattg gtggagaata ttattgactt gtgcctacct ctttttatcc    540
cccctccccg ttttccccctt ctattcatcg ttttgttact tgaatccgcc tccaatcatg    600
aatattgacc atccctatgg cttgacccgt atcataaccg tgtgtcgcat tagctatgta    660
cgtgtcatgc gagacaaaat catgtagata ggtcaaaatg ttggttgtta gattcggtca    720
tcgatagaca gttagggca tctttgattc acatgattct agaaacacat gaaatgaaaa    780
gattgcaaag ttacgcccat ttgaatcatg cacggttttt ggtttggttg catcgccgga    840
aaaacgtgga tccttttcat gaggttttca gtggacacta gaattccttg aatgaatac     900 aaatgaatcc ttggcaaata tttgtgttgg attcaatcct acaaactaaa cgaccagcac    960
ggaaaaagaa tccccaagga ttaaaagact ccttcgattc aaagaggccc tcaacagtgc   1020
```

```
aataccttca aagtcttgga atccatttt  cccatgagca ctgcaagcca cagagagggc    1080
cacacggccg cagcgcacgg agaaggagtc agacgtagca gagcccccat cccgcatagc    1140
atttttattt aatttgcggg gatttctggg gtggtgggcg caagatttgt aactggatgg    1200
cgaagtttgt ctggtgataa agatgggcgc gacgaatccg tccatcgatc caacgctgtg    1260
cgcgtgttgg cccggggccc cgcccgccag cgacccacca ctccacccag acccagatgc    1320
cttccccctc ccatcacccg atgccgtctc gcaatctccc ccctcccctt ccctacaac     1380 tactactact cgctcccgct gccgctcgct cgctcgctcg ctgctttgct ctctctcctt    1440
cttcttcctc cttcttcctc ccccacccc  cgccccccga ccctggatcc aaatcccgac    1500
cctccccaga accggaaccg aggcaagcaa aagcttggcg caattattgg ccggagatag    1560
gtagagaagc gaggcagctc gctcgcggtg aggcgagatc atgaagcgcg agtaccagga    1620
cgccggcggg agcggtggcg ggggcggcat gggctcgtct gaggacaaga tgatggtgtc    1680
ggcggcggcg ggggagggg  aggaggtgga cgagctgctg gcggcgctcg ggtacaaggt    1740
gcgggcctcc gacatggcgg acgtggcgca gaagctggag cagctggaga tggccatggg    1800
gatgggcggc gtgggcgccg cgccgccccc cgacgacagc ttcgccaccc acctcgccac    1860
ggacaccgtg cactacaacc ccaccgacct ctcctcctgg gtcgagagca tgctgtcgga    1920
gctcaacgcg ccgccgccgc ccctcccgcc cgccccgcag cagctcaacg cctccacctc    1980
ctccaccgtc acgggcggtg ggtacttcga tctcccgccc tcggttgact cctcctgcag    2040
cacctacgcc ctgcggccga tcccctcccc ggccggcgcc gtcgggccgg ccgacctgtc    2100
cgccgactcc gtgcgggacc ccaagcggat gcgcactggc gggagcagca cctcgtcgtc    2160
gtcatcctcc tcgtcctctc tcggtggggg cgccaggagc tctgtggtgg aggctgctcc    2220
gccggtcgcg gccggggcca acgcgcccgc gctgccggtc gtcgtggtcg acacgcagga    2280
ggccgggatt cggctggtgc acgcgctgct ggcctgcgcg gaggccgtgc agcaggagaa    2340
cttctctgcc gcggaggcgc tggtgaagca gataccccttg ctggccgcgt cccagggcgg    2400
cgcgatgcgc aaggtcgccg cctacttcgg cgaggccctc gcccgccgcg tcttccgctt    2460
ccgcccgcag ccggacagct ccctcctcga cgccgccttc gccgacctcc tccacgcgca    2520
cttctacgag tcctgcccct acctcaagtt cgcccacttc accgccaacc aggccatcct    2580
ggaggccttc gccggctgcc gccgcgtgca cgtcgtcgac ttcggcatca gcagggat     2640 gcagtggccc gccctcctcc aggccctcgc gctccgtccc ggcggccctc cctcgttccg    2700
cctcaccggc gtcggccccc gcagccgga  cgagaccgac gccttgcagc aggtgggctg    2760
gaagctcgcc cagttcgcgc acaccatccg cgtcgacttc cagtaccgcg gcctcgtcgc    2820
cgccacgctc gcggacctgg agccattcat gctgcagccg gagggcgagg aggacccgaa    2880
cgaggagccc gaggtaatcg ccgtcaactc ggtcttcgag atgcaccggc tgctcgcgca    2940
gcccggcgcc ctggagaagg tcctgggcac cgtgcgcgcc gtgcggccga ggatcgtcac    3000
cgtggtggag caggaggcca accacaactc cggcacattc ctggaccgct tcaccgagtc    3060
tctgcactac tactccacca tgttcgattc cctcgagggc ggcagctccg gcggcccatc    3120
cgaagtctca tcgggggctg ccgctgctcc tgccgccgcc ggcacggacc aggtcatgtc    3180
cgaggtgtac ctcggccggc agatctgcaa cgtggtggcc tgcgagggg  cggagcgcac    3240 agagcgccac gagacgctgg ggcagtggcg gaaccggctg gcaacgccg  ggttcgagac    3300 cgtgcacctg ggctccaatg cctacaagca ggcgagcacg ctgctggccc tattcgccgg    3360
```

```
cggcgacggg tacaaggtgg aggagaagga gggctgcctg actctcgggt ggcacacgcg    3420
cccgctgatc gccacctcgg catggcgcct ggccgcgccg tga                      3463
```

<210> SEQ ID NO 9
<211> LENGTH: 620
<212> TYPE: PRT
<213> ORGANISM: Triticum aestivum

<400> SEQUENCE: 9

```
Met Lys Arg Glu Tyr Gln Asp Ala Gly Gly Ser Gly Gly Gly Gly Gly
1               5                   10                  15

Met Gly Ser Ser Glu Asp Lys Met Met Val Ser Ala Ala Ala Gly Glu
            20                  25                  30

Gly Glu Glu Val Asp Glu Leu Leu Ala Ala Leu Gly Tyr Lys Val Arg
        35                  40                  45

Ala Ser Asp Met Ala Asp Val Ala Gln Lys Leu Glu Gln Leu Glu Met
    50                  55                  60

Ala Met Gly Met Gly Gly Val Gly Ala Gly Ala Ala Pro Asp Asp Ser
65                  70                  75                  80

Phe Ala Thr His Leu Ala Thr Asp Thr Val His Tyr Asn Pro Thr Asp
                85                  90                  95

Leu Ser Ser Trp Val Glu Ser Met Leu Ser Glu Leu Asn Ala Pro Pro
            100                 105                 110

Pro Pro Leu Pro Pro Ala Pro Gln Gln Leu Asn Ala Ser Thr Ser Ser
        115                 120                 125

Thr Val Thr Gly Gly Gly Tyr Phe Asp Leu Pro Pro Ser Val Asp Ser
    130                 135                 140

Ser Cys Ser Thr Tyr Ala Leu Arg Pro Ile Pro Ser Pro Ala Gly Ala
145                 150                 155                 160

Val Gly Pro Ala Asp Leu Ser Ala Asp Ser Val Arg Asp Pro Lys Arg
                165                 170                 175

Met Arg Thr Gly Gly Ser Ser Thr Ser Ser Ser Ser Ser Ser Ser Ser
            180                 185                 190

Ser Leu Gly Gly Gly Ala Arg Ser Ser Val Val Glu Ala Ala Pro Pro
        195                 200                 205

Val Ala Ala Gly Ala Asn Ala Pro Ala Leu Pro Val Val Val Val Asp
    210                 215                 220

Thr Gln Glu Ala Gly Ile Arg Leu Val His Ala Leu Leu Ala Cys Ala
225                 230                 235                 240

Glu Ala Val Gln Gln Glu Asn Phe Ser Ala Ala Glu Ala Leu Val Lys
                245                 250                 255

Gln Ile Pro Leu Leu Ala Ala Ser Gln Gly Gly Ala Met Arg Lys Val
            260                 265                 270

Ala Ala Tyr Phe Gly Glu Ala Leu Ala Arg Arg Val Phe Arg Phe Arg
        275                 280                 285

Pro Gln Pro Asp Ser Ser Leu Leu Asp Ala Ala Phe Ala Asp Leu Leu
    290                 295                 300

His Ala His Phe Tyr Glu Ser Cys Pro Tyr Leu Lys Phe Ala His Phe
305                 310                 315                 320

Thr Ala Asn Gln Ala Ile Leu Glu Ala Phe Ala Gly Cys Arg Arg Val
                325                 330                 335

His Val Val Asp Phe Gly Ile Lys Gln Gly Met Gln Trp Pro Ala Leu
            340                 345                 350

Leu Gln Ala Leu Ala Leu Arg Pro Gly Gly Pro Pro Ser Phe Arg Leu
```

```
                355                 360                 365
Thr Gly Val Gly Pro Gln Pro Asp Glu Thr Asp Ala Leu Gln Gln
    370                 375                 380

Val Gly Trp Lys Leu Ala Gln Phe Ala His Thr Ile Arg Val Asp Phe
385                 390                 395                 400

Gln Tyr Arg Gly Leu Val Ala Ala Thr Leu Ala Asp Leu Glu Pro Phe
                405                 410                 415

Met Leu Gln Pro Glu Gly Glu Asp Pro Asn Glu Glu Pro Glu Val
        420                 425                 430

Ile Ala Val Asn Ser Val Phe Glu Met His Arg Leu Leu Ala Gln Pro
                435                 440                 445

Gly Ala Leu Glu Lys Val Leu Gly Thr Val Arg Ala Val Arg Pro Arg
    450                 455                 460

Ile Val Thr Val Val Glu Gln Glu Ala Asn His Asn Ser Gly Thr Phe
465                 470                 475                 480

Leu Asp Arg Phe Thr Glu Ser Leu His Tyr Tyr Ser Thr Met Phe Asp
                485                 490                 495

Ser Leu Glu Gly Gly Ser Ser Gly Pro Ser Glu Val Ser Ser Gly
        500                 505                 510

Ala Ala Ala Ala Pro Ala Ala Ala Gly Thr Asp Gln Val Met Ser Glu
            515                 520                 525

Val Tyr Leu Gly Arg Gln Ile Cys Asn Val Val Ala Cys Glu Gly Ala
    530                 535                 540

Glu Arg Thr Glu Arg His Glu Thr Leu Gly Gln Trp Arg Asn Arg Leu
545                 550                 555                 560

Gly Asn Ala Gly Phe Glu Thr Val His Leu Gly Ser Asn Ala Tyr Lys
                565                 570                 575

Gln Ala Ser Thr Leu Leu Ala Leu Phe Ala Gly Gly Asp Gly Tyr Lys
            580                 585                 590

Val Glu Glu Lys Glu Gly Cys Leu Thr Leu Gly Trp His Thr Arg Pro
    595                 600                 605

Leu Ile Ala Thr Ser Ala Trp Arg Leu Ala Ala Pro
    610                 615                 620

<210> SEQ ID NO 10
<211> LENGTH: 1872
<212> TYPE: DNA
<213> ORGANISM: Triticum aestivum

<400> SEQUENCE: 10
atgaagcggg agtaccagga cgccggaggg agcggcggcg gcggtggcgg catgggctcg    60
tccgaggaca agatgatggt gtcggcggcg gcggggagg gggaggaggt ggacgagctg   120
ctggcggcgc tcgggtacaa ggtgcgcgcc tccgacatgg cggacgtggc gcagaagctg   180
gagcagctcg agatggccat ggggatgggc ggcgtgggcg ccggcgccgc ccccgacgac   240
agcttcgcca cccacctcgc cacggacacc gtgcactaca cccccaccga cctgtcgtct   300
tgggtcgaga gcatgctgtc ggagctcaac gcgccgccgc cgcccctccc gcccgccccg   360
cagctcaacg cctccacctc ctccaccgtc acgggcagcg cggctacttc gatctcccg   420 ccctccgtcg actcctccag cagcatctac gcgctgcggc cgatcccctc ccggccggc   480 gcgacggcgc cggccgacct gtccgccgac tcgtgcgggg atcccaagcg gatgcgcact   540
ggcgggagca gcacctcgtc gtcatcctcc tcctcgtcgt ctctcggtgg ggcgccagg   600 agctctgtgg tggaggctgc cccgccggtc gcggccgcgg ccaacgcgac gcccgcgctg   660
```

```
ccggtcgtcg tggtcgacac gcaggaggcc gggattcggc tggtgcacgc gctgctggcg      720
tgcgcggagg ccgtgcagca ggagaacctc tccgccgcgg aggcgctggt gaagcagata      780
cccttgctgg ccgcgtccca gggcggcgcg atgcgcaagg tcgccgccta cttcggcgag      840
gccctcgccc gccgcgtctt ccgcttccgc ccgcagccgg acagctccct cctcgacgcc      900
gccttcgccg acctcctcca cgcgcacttc tacgagtcct gccoctacct caagttcgcg      960 cacttcaccg ccaaccaggc catcctggag gcgttcgccg gctgccgccg cgtgcacgtc     1020
gtcgacttcg gcatcaagca ggggatgcag tggcccgcac ttctccaggc cctcgccctc     1080
cgtcccggcg ccctcccctc gttccgcctc accggcgtcg ccccccgca gccgacgag      1140 accgacgccc tgcagcaggt gggctggaag ctcgcccagt cgcgcacac catccgcgtc     1200 gacttccagt accgcggcct cgtcgccgcc acgctcgcgg acctggagcc gttcatgctg     1260
cagccggagg gcgaggagga cccgaacgag gagcccgagg taatcgccgt caactcagtc     1320
ttcgagatgc accggctgct cgcgcagccc ggcgccctgg agaaggtcct gggcaccgtg     1380
cgcgccgtgc ggcccaggat cgtcaccgtg gtggagcagg aggcgaatca caactccggc     1440
acattcctgg accgcttcac cgagtctctg cactactact ccaccatgtt cgattccctc     1500
gagggcggca gctccggcgg cggcccatcc gaagtctcat cggggctgc tgctgctcct      1560 gccgccgccg gcacggacca ggtcatgtcc gaggtgtacc tcggccggca gatctgcaac     1620
gtggtggcct gcgaggggc ggagcgcaca gagcgccacg agacgctggg ccagtggcgg      1680
aaccggctgg gcaacgccgg gttcgagacc gtccacctgg gctccaatgc ctacaagcag     1740
gcgagcacgc tgctggcgct cttcgccggc ggcgacggct acaaggtgga ggagaaggaa     1800
ggctgcctga cgctgggggtg gcacacgcgc ccgctgatcg ccacctcggc atggcgcctg     1860
gccgggccgt ga                                                         1872
```

<210> SEQ ID NO 11
<211> LENGTH: 623
<212> TYPE: PRT
<213> ORGANISM: Triticum aestivum

<400> SEQUENCE: 11

```
Met Lys Arg Glu Tyr Gln Asp Ala Gly Gly Ser Gly Gly Gly Gly
1               5                   10                  15

Gly Met Gly Ser Ser Glu Asp Lys Met Met Val Ser Ala Ala Ala Gly
            20                  25                  30

Glu Gly Glu Glu Val Asp Glu Leu Leu Ala Ala Leu Gly Tyr Lys Val
        35                  40                  45

Arg Ala Ser Asp Met Ala Asp Val Ala Gln Lys Leu Glu Gln Leu Glu
    50                  55                  60

Met Ala Met Gly Met Gly Gly Val Gly Ala Gly Ala Ala Pro Asp Asp
65                  70                  75                  80

Ser Phe Ala Thr His Leu Ala Thr Asp Thr Val His Tyr Asn Pro Thr
                85                  90                  95

Asp Leu Ser Ser Trp Val Glu Ser Met Leu Ser Glu Leu Asn Ala Pro
            100                 105                 110

Pro Pro Pro Leu Pro Pro Ala Pro Gln Leu Asn Ala Ser Thr Ser Ser
        115                 120                 125

Thr Val Thr Gly Ser Gly Gly Tyr Phe Asp Leu Pro Pro Ser Val Asp
    130                 135                 140

Ser Ser Ser Ser Ile Tyr Ala Leu Arg Pro Ile Pro Ser Pro Ala Gly
```

```
            145                 150                 155                 160
        Ala Thr Ala Pro Ala Asp Leu Ser Ala Asp Ser Val Arg Asp Pro Lys
                        165                 170                 175

Arg Met Arg Thr Gly Ser Ser Thr Ser Ser Ser Ser Ser Ser Ser Ser
                        180                 185                 190

Ser Ser Leu Gly Gly Gly Ala Arg Ser Ser Val Val Glu Ala Ala Pro
                        195                 200                 205

Pro Val Ala Ala Ala Ala Asn Ala Thr Pro Ala Leu Pro Val Val Val
        210                 215                 220

Val Asp Thr Gln Glu Ala Gly Ile Arg Leu Val His Ala Leu Leu Ala
        225                 230                 235                 240

Cys Ala Glu Ala Val Gln Gln Glu Asn Leu Ser Ala Ala Glu Ala Leu
                        245                 250                 255

Val Lys Gln Ile Pro Leu Leu Ala Ser Gln Gly Gly Ala Met Arg
                        260                 265                 270

Lys Val Ala Ala Tyr Phe Gly Glu Ala Leu Ala Arg Arg Val Phe Arg
                        275                 280                 285

Phe Arg Pro Gln Pro Asp Ser Ser Leu Leu Asp Ala Ala Phe Ala Asp
                        290                 295                 300

Leu Leu His Ala His Phe Tyr Glu Ser Cys Pro Tyr Leu Lys Phe Ala
        305                 310                 315                 320

His Phe Thr Ala Asn Gln Ala Ile Leu Glu Ala Phe Ala Gly Cys Arg
                        325                 330                 335

Arg Val His Val Val Asp Phe Gly Ile Lys Gln Gly Met Gln Trp Pro
                        340                 345                 350

Ala Leu Leu Gln Ala Leu Ala Leu Arg Pro Gly Gly Pro Pro Ser Phe
                        355                 360                 365

Arg Leu Thr Gly Val Gly Pro Pro Gln Pro Asp Glu Thr Asp Ala Leu
                        370                 375                 380

Gln Gln Val Gly Trp Lys Leu Ala Gln Phe Ala His Thr Ile Arg Val
        385                 390                 395                 400

Asp Phe Gln Tyr Arg Gly Leu Val Ala Ala Thr Leu Ala Asp Leu Glu
                        405                 410                 415

Pro Phe Met Leu Gln Pro Glu Gly Glu Glu Asp Pro Asn Glu Glu Pro
                        420                 425                 430

Glu Val Ile Ala Val Asn Ser Val Phe Glu Met His Arg Leu Leu Ala
                        435                 440                 445

Gln Pro Gly Ala Leu Glu Lys Val Leu Gly Thr Val Arg Ala Val Arg
                        450                 455                 460

Pro Arg Ile Val Thr Val Val Glu Gln Glu Ala Asn His Asn Ser Gly
        465                 470                 475                 480

Thr Phe Leu Asp Arg Phe Thr Glu Ser Leu His Tyr Tyr Ser Thr Met
                        485                 490                 495

Phe Asp Ser Leu Glu Gly Gly Ser Ser Gly Gly Pro Ser Glu Val
                        500                 505                 510

Ser Ser Gly Ala Ala Ala Pro Ala Ala Gly Thr Asp Gln Val
                        515                 520                 525

Met Ser Glu Val Tyr Leu Gly Arg Gln Ile Cys Asn Val Val Ala Cys
                        530                 535                 540

Glu Gly Ala Glu Arg Thr Glu Arg His Glu Thr Leu Gly Gln Trp Arg
        545                 550                 555                 560

Asn Arg Leu Gly Asn Ala Gly Phe Glu Thr Val His Leu Gly Ser Asn
                        565                 570                 575
```

```
Ala Tyr Lys Gln Ala Ser Thr Leu Leu Ala Leu Phe Ala Gly Gly Asp
            580                 585                 590

Gly Tyr Lys Val Glu Glu Lys Glu Gly Cys Leu Thr Leu Gly Trp His
        595                 600                 605

Thr Arg Pro Leu Ile Ala Thr Ser Ala Trp Arg Leu Ala Gly Pro
    610                 615                 620

<210> SEQ ID NO 12
<211> LENGTH: 618
<212> TYPE: PRT
<213> ORGANISM: Hordeum vulgare

<400> SEQUENCE: 12

Met Lys Arg Glu Tyr Gln Asp Gly Gly Ser Gly Gly Gly Gly Gly Asp
1               5                   10                  15

Glu Met Gly Ser Ser Arg Asp Lys Met Met Val Ser Ser Ser Glu Ala
            20                  25                  30

Gly Glu Gly Glu Glu Val Asp Glu Leu Leu Ala Ala Leu Gly Tyr Lys
        35                  40                  45

Val Arg Ala Ser Asp Met Ala Asp Val Ala Gln Lys Leu Glu Gln Leu
    50                  55                  60

Glu Met Ala Met Gly Met Gly Gly Pro Ala Pro Asp Asp Gly Phe Ala
65                  70                  75                  80

Thr His Leu Ala Thr Asp Thr Val His Tyr Asn Pro Thr Asp Leu Ser
                85                  90                  95

Ser Trp Val Glu Ser Met Leu Ser Glu Leu Asn Ala Pro Pro Pro Pro
            100                 105                 110

Leu Pro Pro Ala Pro Pro Gln Leu Asn Ala Ser Thr Ser Ser Thr Val
        115                 120                 125

Thr Gly Gly Gly Gly Tyr Phe Asp Leu Pro Pro Ser Val Asp Ser Ser
    130                 135                 140

Ser Ser Thr Tyr Ala Leu Arg Pro Ile Ile Ser Pro Pro Val Ala Pro
145                 150                 155                 160

Ala Asp Leu Ser Ala Asp Ser Val Arg Asp Pro Lys Arg Met Arg Thr
                165                 170                 175

Gly Gly Ser Ser Thr Ser Ser Ser Ser Ser Ser Ser Ser Ser Leu Gly
            180                 185                 190

Gly Gly Ala Ala Arg Ser Ser Val Val Glu Ala Ala Pro Pro Val Ala
        195                 200                 205

Ala Ala Ala Ala Pro Ala Leu Pro Val Val Val Asp Thr Gln
    210                 215                 220

Glu Ala Gly Ile Arg Leu Val His Ala Leu Leu Ala Cys Ala Glu Ala
225                 230                 235                 240

Val Gln Gln Glu Asn Leu Ser Ala Ala Glu Ala Leu Val Lys Gln Ile
                245                 250                 255

Pro Leu Leu Ala Ala Ser Gln Gly Gly Ala Met Arg Lys Val Ala Ala
            260                 265                 270

Tyr Phe Gly Glu Ala Leu Ala Arg Arg Val Phe Arg Phe Arg Pro Gln
        275                 280                 285

Pro Asp Ser Ser Leu Leu Asp Ala Ala Phe Ala Asp Leu Leu His Ala
    290                 295                 300

His Phe Tyr Glu Ser Cys Pro Tyr Leu Lys Phe Ala His Phe Thr Ala
305                 310                 315                 320

Asn Gln Ala Ile Leu Glu Ala Phe Ala Gly Cys Arg Arg Val His Val
```

```
                    325                 330                 335
Val Asp Phe Gly Ile Lys Gln Gly Met Gln Trp Pro Ala Leu Leu Gln
                340                 345                 350

Ala Leu Ala Leu Arg Pro Gly Pro Pro Ser Phe Arg Leu Thr Gly
            355                 360                 365

Val Gly Pro Pro Gln Pro Asp Glu Thr Asp Ala Leu Gln Gln Val Gly
    370                 375                 380

Trp Lys Leu Ala Gln Phe Ala His Thr Ile Arg Val Asp Phe Gln Tyr
385                 390                 395                 400

Arg Gly Leu Val Ala Ala Thr Leu Ala Asp Leu Glu Pro Phe Met Leu
                405                 410                 415

Gln Pro Glu Gly Glu Glu Asp Pro Asn Glu Pro Glu Val Ile Ala
            420                 425                 430

Val Asn Ser Val Phe Glu Met His Arg Leu Leu Ala Gln Pro Gly Ala
                435                 440                 445

Leu Glu Lys Val Leu Gly Thr Val Arg Ala Val Arg Pro Arg Ile Val
            450                 455                 460

Thr Val Val Glu Gln Glu Ala Asn His Asn Ser Gly Ser Phe Leu Asp
465                 470                 475                 480

Arg Phe Thr Glu Ser Leu His Tyr Tyr Ser Thr Met Phe Asp Ser Leu
                485                 490                 495

Glu Gly Gly Ser Ser Gly Gly Pro Ser Glu Val Ser Ser Gly Gly Ala
            500                 505                 510

Ala Pro Ala Ala Ala Gly Thr Asp Gln Val Met Ser Glu Val Tyr
            515                 520                 525

Leu Gly Arg Gln Ile Cys Asn Val Val Ala Cys Glu Gly Thr Glu Arg
530                 535                 540

Thr Glu Arg His Glu Thr Leu Gly Gln Trp Arg Asn Arg Leu Gly Asn
545                 550                 555                 560

Ala Gly Phe Glu Thr Val His Leu Gly Ser Asn Ala Tyr Lys Gln Ala
                565                 570                 575

Ser Thr Leu Leu Ala Leu Phe Ala Gly Gly Asp Gly Tyr Lys Val Glu
            580                 585                 590

Glu Lys Glu Gly Cys Leu Thr Leu Gly Trp His Thr Arg Pro Leu Ile
            595                 600                 605

Ala Thr Ser Ala Trp Arg Leu Ala Ala Pro
            610                 615

<210> SEQ ID NO 13
<211> LENGTH: 532
<212> TYPE: PRT
<213> ORGANISM: Arabidopsis thaliana

<400> SEQUENCE: 13

Met Lys Arg Asp His His His His Gln Asp Lys Lys Thr Met Met
1               5                   10                  15

Met Asn Glu Glu Asp Asp Gly Asn Gly Met Asp Glu Leu Leu Ala Val
                20                  25                  30

Leu Gly Tyr Lys Val Arg Ser Ser Glu Met Ala Asp Val Ala Gln Lys
            35                  40                  45

Leu Glu Gln Leu Glu Val Met Met Ser Asn Val Gln Glu Asp Asp Leu
        50                  55                  60

Ser Gln Leu Ala Thr Glu Thr Val His Tyr Asn Pro Ala Glu Leu Tyr
65              70                  75                  80
```

```
Thr Trp Leu Asp Ser Met Leu Thr Asp Leu Asn Pro Ser Ser Asn
                 85                  90                  95

Ala Glu Tyr Asp Leu Lys Ala Ile Pro Gly Asp Ala Ile Leu Asn Gln
            100                 105                 110

Phe Ala Ile Asp Ser Ala Ser Ser Asn Gln Gly Gly Gly Gly Asp
            115                 120                 125

Thr Tyr Thr Thr Asn Lys Arg Leu Lys Cys Ser Asn Gly Val Val Glu
            130                 135                 140

Thr Thr Thr Ala Thr Ala Glu Ser Thr Arg His Val Val Leu Val Asp
145                 150                 155                 160

Ser Gln Glu Asn Gly Val Arg Leu Val His Ala Leu Leu Ala Cys Ala
                165                 170                 175

Glu Ala Val Gln Lys Glu Asn Leu Thr Val Ala Glu Ala Leu Val Lys
                180                 185                 190

Gln Ile Gly Phe Leu Ala Val Ser Gln Ile Gly Ala Met Arg Lys Val
                195                 200                 205

Ala Thr Tyr Phe Ala Glu Ala Leu Ala Arg Arg Ile Tyr Arg Leu Ser
            210                 215                 220

Pro Ser Gln Ser Pro Ile Asp His Ser Leu Ser Asp Thr Leu Gln Met
225                 230                 235                 240

His Phe Tyr Glu Thr Cys Pro Tyr Leu Lys Phe Ala His Phe Thr Ala
                245                 250                 255

Asn Gln Ala Ile Leu Glu Ala Phe Gln Gly Lys Lys Arg Val His Val
                260                 265                 270

Ile Asp Phe Ser Met Ser Gln Gly Leu Gln Trp Pro Ala Leu Met Gln
            275                 280                 285

Ala Leu Ala Leu Arg Pro Gly Gly Pro Pro Val Phe Arg Leu Thr Gly
            290                 295                 300

Ile Gly Pro Pro Ala Pro Asp Asn Phe Asp Tyr Leu His Glu Val Gly
305                 310                 315                 320

Cys Lys Leu Ala His Leu Ala Glu Ala Ile His Val Glu Phe Glu Tyr
                325                 330                 335

Arg Gly Phe Val Ala Asn Thr Leu Ala Asp Leu Asp Ala Ser Met Leu
            340                 345                 350

Glu Leu Arg Pro Ser Glu Ile Glu Ser Val Ala Val Asn Ser Val Phe
            355                 360                 365

Glu Leu His Lys Leu Leu Gly Arg Pro Gly Ala Ile Asp Lys Val Leu
            370                 375                 380

Gly Val Val Asn Gln Ile Lys Pro Glu Ile Phe Thr Val Val Glu Gln
385                 390                 395                 400

Glu Ser Asn His Asn Ser Pro Ile Phe Leu Asp Arg Phe Thr Glu Ser
                405                 410                 415

Leu His Tyr Tyr Ser Thr Leu Phe Asp Ser Leu Glu Gly Val Pro Ser
            420                 425                 430

Gly Gln Asp Lys Val Met Ser Glu Val Tyr Leu Gly Lys Gln Ile Cys
            435                 440                 445

Asn Val Val Ala Cys Asp Gly Pro Asp Arg Val Glu Arg His Glu Thr
            450                 455                 460

Leu Ser Gln Trp Arg Asn Arg Phe Gly Ser Ala Gly Phe Ala Ala Ala
465                 470                 475                 480

His Ile Gly Ser Asn Ala Phe Lys Gln Ala Ser Met Leu Leu Ala Leu
                485                 490                 495

Phe Asn Gly Gly Glu Gly Tyr Arg Val Glu Glu Ser Asp Gly Cys Leu
```

```
                500               505               510
Met Leu Gly Trp His Thr Arg Pro Leu Ile Ala Thr Ser Ala Trp Lys
            515               520               525

Leu Ser Thr Asn
    530

<210> SEQ ID NO 14
<211> LENGTH: 30
<212> TYPE: PRT
<213> ORGANISM: Triticum aestivum

<400> SEQUENCE: 14

Asp Ser Ala Thr Pro Pro Asp Ala Pro Leu Val Ala Ala Gly Leu
1               5                   10                  15

Ala Ala Asn Glu Thr Thr His Ile Lys Ile Ser Ala Asn Lys
            20                  25                  30

<210> SEQ ID NO 15
<211> LENGTH: 11
<212> TYPE: PRT
<213> ORGANISM: Triticum aestivum

<400> SEQUENCE: 15

Asp Glu Leu Leu Ala Ala Leu Gly Tyr Lys Val
1               5                   10

<210> SEQ ID NO 16
<211> LENGTH: 4501
<212> TYPE: DNA
<213> ORGANISM: Triticum aestivum

<400> SEQUENCE: 16
atgccgtcta caactactac gctgccgctc cctcgctgct ctgctcgctc tcctccctcc      60 ccacccaac catccccgtc tcctcctcct tcctcctctc cccgaccct ggatccaaat      120 cccggcccgc ccagagccg gaatcgaggc aagcaaaagc ttgagataga tagagaggcg      180
aggtagggag gcgagaggcg agatcatgaa gcgcgagtac caggacgccg agggagcgg      240 cggtggccgg ggaggcatgg gctcgtccga ggacaagata tggtgtcgg ggtcggcggc      300 ggcgggggag ggggaggagg tggacgagct gctggcggcg ctcgggtaca aggtgtgttg      360
gcgccgcctc ctcgcagcgc cgttcttctt cctctcatct tcatgaaca cacaccatgg      420 agaaactcta cacacacaca cacaaccaa gaagaacac cggctgttac tttgcacgag      480
aggcccttct ccttggtgga acaagagact acattgtgtt tttcccagcc ctcttggctc      540 actttctca ttcatcttct ccaacttaaa tagctaagta caagactgac ccaagcactt      600
gccagccgcc actctcgcag ctgctaacgc ccactaactc atgcactagg ccactaatca      660
caactaactc atgcacgcat gcaccacacc ggccactatc acatgaccgg gcgactaacc      720
cactagctac atgcatgcaa ctagataact accttatcca tgcactccag gactcggcaa      780
ctccaccgga cgccccgctc gtagcagccg cgggacttgc tgctaacgaa accacgcaca      840
tcaagattag tgctaacatt tcccccctta atcttgacac gccttgccgt cgaccgtcat      900
cttgaacgcc tgagctcgac gtcttcacac gcctccgcgc ccgctgcgac gtgccgtgcg      960
cccgcctgtc accggagttg atgcagcttg cgtcgtcgtc gtcacggccg tgacccagcc     1020
tgcggacccg acccgacgca tcgacgccgg tcacaccgcc acggaccga cctggcgcac     1080 tgacgccggt cgcaccgtgc tccctcacga ccccggcgac atacgccgag ctcctccgcc     1140
```

```
ggcgacacac gcctggcgtc cctctgcgtc ccgcacgtcc cgcacgcatc cgacgtgccc    1200
gacgagcccg accgcagcag tgcgtcccgc acgtcccgcg cgcattcgac gcgcccgacg    1260
agcccgacag caccagacgc tcaccacgtg ccgcctccgc gtccgccatg cagccacca     1320 cgccgcgcct acgtgccacg caccttccac ggtcgttgcc ccgagccgtc gcgacctatg    1380
cgccaccacg caggtccttc gcgacctcct cgtctccgcg accgccgtgc ccttcgcgca    1440
cactccccac gtccccgcgc tcccagcccg cgctcccgcc gcgcacgtac gcggtctgcg    1500
caaccaggtc cagcgcctcg acgcggtcca ctcccgcggt cccgacgcgc tcgacacgtc    1560
cagtgcgcgc cctaacacg caccggtcgc gtccggctcg ccgccgcatc ttattgccct     1620
gcaccgccgc ggcctccatg ccgccatgca gtgcctccac gccgccacac cgtgttgcac    1680
cgctgcgcca ccacgcagcg cctcggcggc ctccgcggtc gccgcacgta cgacgtcacc    1740
gcccgccgcc tccgccacgc gctcgccgcg cgccgcagcc gatgcctcca tgtcggccgc    1800
gcatgccccg tccgccgcgg acgccaccgc gcgccacggc cgcccctcga accttgtggc    1860
tctgaatacc aaatgttggc gccgcctcct cgcagcgccg ttcttcttcc tctcatctct    1920
catgaacaca caccatggag aaactctaca cacacacaca caaccaag aagaacaccg      1980 gctgttactt tgcacgagag gcccttctcc ttggtggaac aagagactac attgtgtttt    2040
tcccagccct cttggctcac ttttctcatt catcttctcc aacttaaata gctaagtaca    2100
agactgaccc aagcacttgc cagccgccac tctcgcagct gctaacgccc actaactcat    2160
gcactaggcc actaatcaca actaactcat gcacgcatgc accacaccgg ccactatcac    2220 atgacccgggc gactaaccca ctagctacat gcatgcaact agataactac cttatccatg   2280
cactccagga ctcggcaact ccaccggacg ccccgctcgt agcagccgcg ggacttgctg    2340
ctaacgaaac cacgcacatc aagattagtg ctaacaaggt gcgggcgtcc gacatggcgg    2400
acgtggcgca gaagctggag cagctggaga tggccatggg gatgggcggc gtgggcgccg    2460
gcgccgcgcc cgacgacagc ttcgccaccc acctcgccac ggacaccgtg cactacaacc    2520
ccaccgacct ctcctcctgg gtcgagagca tgctgtcgga gctcaacgcg ccgccgccgc    2580
ccctcccgcc cgccccgcag ctcaacgcct ccacctcctc caccgtcacc ggcggcgggt    2640
acttcgatct cccgccctcc gtcgactcct cctgcagcac ctacgcgctg cggccgatcc    2700
cgtcccccgc cgtcgcgccg ccgaccctct ccgccgactc cgtcgtgcgg gatcccaagc    2760
ggatgcgcac tggcggcagc agcacctcgt cgtcatcctc atcgtcctct ctcggcggtg    2820
gcggcgccag gagctctgtg gtggaggctg ccccgccggt ggccgccgcg gccggtgcgc    2880
ccgcgctgcc ggtcgtcgtg gtcgacacgc aggaggccgg gattcggctg gtgcacgcgc    2940
tgctggcgtg cgcagaggcc gtgcagcagg agaacttctc tgccgcggag gcgctggtga    3000
agcagatacc cttgctggcc gcgtcccagg gcggcgccat gcgcaaggtc gccgcctact    3060
tcggcgaggc cctcgcccgc cgcgtcttcc gcttccgccc gcagccggac agctccctcc    3120
tcgacgccgc cttcgccgac ctcctccacg cgcacttcta cgagtcctgc ccctacctca    3180
agttcgccca cttcaccgcc aaccaggcca tcctggaggc gttcgccggc tgccgccgcg    3240
tgcacgtcgt cgacttcggc atcaagcagg ggatgcagtg gccgcccctt ctccaggccc    3300
tggcgctccg tccggcggc cctccctcgt tccgcctcac cggcgtcggc ccccgcagc     3360 cggacgagac cgacgccttg cagcaggtgg gctggaagct cgcccagttc gcgcacacca    3420
tccgcgtcga cttccagtac cgcggcctcg tcgccgccac gctcgcggac ctggagccgt    3480
tcatgctgca gccggagggc gaggaggacc cgaacgagga gcccgaggta atcgccgtca    3540
```

```
actcggtctt cgagatgcac cggctgctcg cgcagcccgg cgccctggag aaggtcctgg    3600
gcaccgtgcg cgccgtgcgg ccgaggatcg tcaccgtggt ggagcaggag gcgaaccaca    3660
actccggcac attcctggac cgcttcaccg agtccctgca ctactactcc accatgttcg    3720
attctctgga gggcggcagc tccggcggcc catccgaagt ctcatctggg gcggctgctg    3780
ctcctgccgc cgccggcacg gaccaggtca tgtccgaggt gtacctcggc cggcagatct    3840
gcaacgtggt ggcctgcgag ggggcggagc gcacagagcg gcacgagacc ctggggcagt    3900
ggcggaaccg cctcggcaac gccgggttcg agaccgtcca cctgggctcc aatgcctaca    3960
agcaggcgag cacgctgctg gcgctcttcg caggcggcga cgggtacaag gtggaggaga    4020
aggagggctg cctgacgctg gggtggcaca cgcgcccgct gatcgccacc tccgcatggc    4080
gcctggccgc gccgtgaccg cgagttttga acgctgtaag tacacatcgt gagcatggag    4140
gacgacacaa ccccggcggc cgccccggct ctccggcgca cgcacgcacg cacgctcttg    4200
aagaagaaga agaagctaaa tgtcatgtca gtgaacgctg aattgcagcg gccggccacg    4260
atcgaccgtc cggcgtgaag agacggacga cgacgaactc cgagccgacc atcccaccgg    4320
catgtagtaa tgtaatccct tcttcgtccc cagttctcca ccgcctccat gatcacccgt    4380
aaaactccca agccctacta ctactactac tactactact actactatca tgtttaaatg    4440
tctattattg caatgtgtaa ttcctccaat cgctcatatc aaaataagcg cgggccggac    4500
t                                                                   4501
```

<210> SEQ ID NO 17
<211> LENGTH: 24
<212> TYPE: DNA
<213> ORGANISM: Triticum aestivum

<400> SEQUENCE: 17
ggcaagcaaa agcttgagat agat                                           24

<210> SEQ ID NO 18
<211> LENGTH: 19
<212> TYPE: DNA
<213> ORGANISM: Triticum aestivum

<400> SEQUENCE: 18
ggtgcagggc aataagatg                                                 19

<210> SEQ ID NO 19
<211> LENGTH: 19
<212> TYPE: DNA
<213> ORGANISM: Triticum aestivum

<400> SEQUENCE: 19
gacagcacca gacgctcac                                                 19

<210> SEQ ID NO 20
<211> LENGTH: 19
<212> TYPE: DNA
<213> ORGANISM: Triticum aestivum

<400> SEQUENCE: 20
gctctcgacc caggaggag                                                 19

<210> SEQ ID NO 21
<211> LENGTH: 18
<212> TYPE: DNA

```
<213> ORGANISM: Triticum aestivum

<400> SEQUENCE: 21
tggagcagct ggagatgg                                                 18

<210> SEQ ID NO 22
<211> LENGTH: 20
<212> TYPE: DNA
<213> ORGANISM: Triticum aestivum

<400> SEQUENCE: 22
taggggcagg actcgtagaa                                               20

<210> SEQ ID NO 23
<211> LENGTH: 19
<212> TYPE: DNA
<213> ORGANISM: Triticum aestivum

<400> SEQUENCE: 23
gcgctggtga agcagatac                                                19

<210> SEQ ID NO 24
<211> LENGTH: 18
<212> TYPE: DNA
<213> ORGANISM: Triticum aestivum

<400> SEQUENCE: 24
ttcaaactcg cggtcacg                                                 18

<210> SEQ ID NO 25
<211> LENGTH: 22
<212> TYPE: DNA
<213> ORGANISM: Triticum aestivum

<400> SEQUENCE: 25
tctcctccct ccccacccca ac                                            22

<210> SEQ ID NO 26
<211> LENGTH: 18
<212> TYPE: DNA
<213> ORGANISM: Triticum aestivum

<400> SEQUENCE: 26
gcgtccggtg gagttgcc                                                 18

<210> SEQ ID NO 27
<211> LENGTH: 20
<212> TYPE: DNA
<213> ORGANISM: Triticum aestivum

<400> SEQUENCE: 27 gtgttttcc cagccctctt                                                20

<210> SEQ ID NO 28
<211> LENGTH: 19
<212> TYPE: DNA
<213> ORGANISM: Triticum aestivum

<400> SEQUENCE: 28
gctctcgacc caggaggag                                                19

<210> SEQ ID NO 29
<211> LENGTH: 18
```

```
<212> TYPE: DNA
<213> ORGANISM: Triticum aestivum

<400> SEQUENCE: 29
gaggtagctc gcggatca                                                    18

<210> SEQ ID NO 30
<211> LENGTH: 18
<212> TYPE: DNA
<213> ORGANISM: Triticum aestivum

<400> SEQUENCE: 30
cgttcaaaac tcgcgaga                                                    18

<210> SEQ ID NO 31
<211> LENGTH: 620
<212> TYPE: PRT
<213> ORGANISM: Artificial Sequence
<220> FEATURE:
<223> OTHER INFORMATION: Consensus Sequence

<400> SEQUENCE: 31

Met Lys Arg Glu Tyr Gln Asp Ala Gly Gly Ser Gly Gly Gly Gly
1               5                   10                  15

Gly Met Gly Ser Ser Glu Asp Lys Met Met Val Ser Ala Ala Ala Gly
            20                  25                  30

Glu Gly Glu Glu Val Asp Glu Leu Leu Ala Ala Leu Gly Tyr Lys Val
        35                  40                  45

Arg Ala Ser Asp Met Ala Asp Val Ala Gln Lys Leu Glu Gln Leu Glu
    50                  55                  60

Met Ala Met Gly Met Gly Gly Val Gly Ala Gly Ala Ala Pro Asp Asp
65                  70                  75                  80

Ser Phe Ala Thr His Leu Ala Thr Asp Thr Val His Tyr Asn Pro Thr
                85                  90                  95

Asp Leu Ser Ser Trp Val Glu Ser Met Leu Ser Glu Leu Asn Ala Pro
            100                 105                 110

Pro Pro Pro Leu Pro Pro Ala Pro Gln Leu Asn Ala Ser Thr Ser Ser
        115                 120                 125

Thr Val Thr Gly Gly Gly Tyr Phe Asp Leu Pro Pro Ser Val Asp Ser
    130                 135                 140

Ser Cys Ser Thr Tyr Ala Leu Arg Pro Ile Pro Ser Pro Ala Gly Ala
145                 150                 155                 160

Val Ala Pro Ala Asp Leu Ser Ala Asp Ser Val Arg Asp Pro Lys Arg
                165                 170                 175

Met Arg Thr Gly Gly Ser Ser Thr Ser Ser Ser Ser Ser Ser Ser Ser
            180                 185                 190

Ser Leu Gly Gly Gly Ala Arg Ser Ser Val Val Glu Ala Ala Pro Pro
        195                 200                 205

Val Ala Ala Ala Ala Asn Ala Pro Ala Leu Pro Val Val Val Val Asp
    210                 215                 220

Thr Gln Glu Ala Gly Ile Arg Leu Val His Ala Leu Leu Ala Cys Ala
225                 230                 235                 240

Glu Ala Val Gln Gln Glu Asn Phe Ser Ala Glu Ala Leu Val Lys
                245                 250                 255

Gln Ile Pro Leu Leu Ala Ala Ser Gln Gly Gly Ala Met Arg Lys Val
            260                 265                 270

Ala Ala Tyr Phe Gly Glu Ala Leu Ala Arg Arg Val Phe Arg Phe Arg
```

```
                275                 280                 285
Pro Gln Pro Asp Ser Ser Leu Leu Asp Ala Ala Phe Ala Asp Leu Leu
        290                 295                 300
His Ala His Phe Tyr Glu Ser Cys Pro Tyr Leu Lys Phe Ala His Phe
305                 310                 315                 320
Thr Ala Asn Gln Ala Ile Leu Glu Ala Phe Ala Gly Cys Arg Arg Val
                325                 330                 335
His Val Val Asp Phe Gly Ile Lys Gln Gly Met Gln Trp Pro Ala Leu
            340                 345                 350
Leu Gln Ala Leu Ala Leu Arg Pro Gly Gly Pro Pro Ser Phe Arg Leu
            355                 360                 365
Thr Gly Val Gly Pro Pro Gln Pro Asp Glu Thr Asp Ala Leu Gln Gln
        370                 375                 380
Val Gly Trp Lys Leu Ala Gln Phe Ala His Thr Ile Arg Val Asp Phe
385                 390                 395                 400
Gln Tyr Arg Gly Leu Val Ala Ala Thr Leu Ala Asp Leu Glu Pro Phe
                405                 410                 415
Met Leu Gln Pro Glu Gly Glu Glu Asp Pro Asn Glu Glu Pro Glu Val
            420                 425                 430
Ile Ala Val Asn Ser Val Phe Glu Met His Arg Leu Leu Ala Gln Pro
            435                 440                 445
Gly Ala Leu Glu Lys Val Leu Gly Thr Val Arg Ala Val Arg Pro Arg
450                 455                 460
Ile Val Thr Val Val Glu Gln Glu Ala Asn His Asn Ser Gly Thr Phe
465                 470                 475                 480
Leu Asp Arg Phe Thr Glu Ser Leu His Tyr Tyr Ser Thr Met Phe Asp
                485                 490                 495
Ser Leu Glu Gly Gly Ser Ser Gly Pro Ser Glu Val Ser Ser Gly
            500                 505                 510
Ala Ala Ala Ala Pro Ala Ala Ala Gly Thr Asp Gln Val Met Ser Glu
            515                 520                 525
Val Tyr Leu Gly Arg Gln Ile Cys Asn Val Val Ala Cys Glu Gly Ala
        530                 535                 540
Glu Arg Thr Glu Arg His Glu Thr Leu Gly Gln Trp Arg Asn Arg Leu
545                 550                 555                 560
Gly Asn Ala Gly Phe Glu Thr Val His Leu Gly Ser Asn Ala Tyr Lys
                565                 570                 575
Gln Ala Ser Thr Leu Leu Ala Leu Phe Ala Gly Gly Asp Gly Tyr Lys
            580                 585                 590
Val Glu Glu Lys Glu Gly Cys Leu Thr Leu Gly Trp His Thr Arg Pro
            595                 600                 605
Leu Ile Ala Thr Ser Ala Trp Arg Leu Ala Ala Pro
610                 615                 620
```